(12) United States Patent
Takasu et al.

(10) Patent No.: US 9,162,990 B2
(45) Date of Patent: Oct. 20, 2015

(54) HETEROCYCLIC COMPOUND, LIGHT-EMITTING ELEMENT, LIGHT-EMITTING DEVICE, ELECTRONIC DEVICE, LIGHTING DEVICE, AND ORGANIC COMPOUND

(75) Inventors: Takako Takasu, Kanagawa (JP); Harue Osaka, Kanagawa (JP); Satoko Shitagaki, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 539 days.

(21) Appl. No.: 13/596,725

(22) Filed: Aug. 28, 2012

(65) Prior Publication Data

US 2013/0075704 A1    Mar. 28, 2013

(30) Foreign Application Priority Data

Aug. 31, 2011 (JP) ................. 2011-189086
Jul. 6, 2012 (JP) ................. 2012-152280

(51) Int. Cl.
C07D 241/38 (2006.01)
C07C 25/22 (2006.01)
(Continued)

(52) U.S. Cl.
CPC .......... *C07D 241/38* (2013.01); *C07C 25/22* (2013.01); *C07F 5/025* (2013.01); *H01L 51/0072* (2013.01); *H01L 51/006* (2013.01); *H01L 51/0074* (2013.01); *H01L 51/0085* (2013.01);
(Continued)

(58) Field of Classification Search
CPC ....... C07C 25/22; C07D 241/38; C07F 5/025; H01L 2251/308; H01L 51/006; H01L 51/0072; H01L 51/0074; H01L 51/0085; H01L 51/5072; H01L 51/50; H05B 33/14; C09K 11/06
See application file for complete search history.

(56) References Cited

U.S. PATENT DOCUMENTS 6,723,445 B2    4/2004    Li et al.
7,355,340 B2    4/2008    Shitagaki et al.
(Continued)

FOREIGN PATENT DOCUMENTS

EP    2 363 398 A1    9/2011
JP    2007-189001 A    7/2007
(Continued)

OTHER PUBLICATIONS

Yao et al., Chemistry—A European Journal, (2012), 18(9), pp. 2707-2714.*
(Continued)

*Primary Examiner* — Dawn Garrett
(74) *Attorney, Agent, or Firm* — Fish & Richardson P.C.

(57) ABSTRACT

Provided is a novel heterocyclic compound which can be used in a light-emitting layer of a light-emitting element as a host material in which a light-emitting material is dispersed, i.e., a heterocyclic compound represented by a general formula (G1). Any one of $R^1$ to $R^{10}$ represents a substituent represented by a general formula (G1-1); another one of $R^1$ to $R^{10}$ represents hydrogen, an alkyl group having 1 to 6 carbon atoms, a substituted or unsubstituted phenyl group, a substituted or unsubstituted biphenyl group, or a substituent represented by a general formula (G1-2); and the others separately represent hydrogen, an alkyl group having 1 to 6 carbon atoms, a substituted or unsubstituted phenyl group, or a substituted or unsubstituted biphenyl group.

19 Claims, 42 Drawing Sheets

(51) Int. Cl.
*C07F 5/02* (2006.01)
*H01L 51/50* (2006.01)
*H01L 51/00* (2006.01)

(52) U.S. Cl.
CPC ....... *H01L 51/5072* (2013.01); *H01L 2251/308* (2013.01)

(56) References Cited

U.S. PATENT DOCUMENTS

| | | | |
|---|---|---|---|
| 2004/0076853 A1* | 4/2004 | Jarikov | 428/690 |
| 2005/0164032 A1* | 7/2005 | Ise et al. | 428/690 |
| 2007/0145888 A1* | 6/2007 | Yabunouchi et al. | 313/504 |
| 2009/0072718 A1 | 3/2009 | Nomura et al. | |
| 2009/0140641 A1 | 6/2009 | Nomura et al. | |
| 2009/0140642 A1 | 6/2009 | Kadoma et al. | |
| 2009/0153041 A1 | 6/2009 | Kawakami et al. | |
| 2009/0184633 A1 | 7/2009 | Kadoma et al. | |
| 2009/0203704 A1 | 8/2009 | Kadoma et al. | |
| 2010/0039024 A1 | 2/2010 | Wendeborn et al. | |
| 2010/0194270 A1* | 8/2010 | Kawamura et al. | 313/504 |
| 2010/0249349 A1 | 9/2010 | Chebotareva et al. | |
| 2011/0089407 A1 | 4/2011 | Schmidhalter et al. | |
| 2011/0210316 A1 | 9/2011 | Kadoma et al. | |
| 2012/0193613 A1 | 8/2012 | Kadoma et al. | |
| 2012/0197020 A1 | 8/2012 | Osaka et al. | |
| 2013/0048971 A1 | 2/2013 | Kitano et al. | |

FOREIGN PATENT DOCUMENTS

| | | |
|---|---|---|
| JP | 2008-239613 A | 10/2008 |
| JP | 2011-201869 A | 10/2011 |
| WO | 03/058667 A1 | 7/2003 |
| WO | 2004/043937 A1 | 5/2004 |
| WO | 2007/090773 A1 | 8/2007 |
| WO | 2008/031743 A1 | 3/2008 |
| WO | 2009/100991 A1 | 8/2009 |
| WO | WO 2011081431 A2 * | 7/2011 |

OTHER PUBLICATIONS

Machine translation of WO 2011/081431 (publication date Jul. 2011).*

Christian R. Goldsmith et al.; "C—H Bond Activation by a Ferric Methoxide Complex: Modeling the Rate-Determining Step in the Mechanism of Lipoxygenase"; J. Am. Chem. Soc. (Journal of the American Chemical Society); 2002; pp. 83-96; vol. 124, No. 1.

T. Onishi et al.; "A Method of Measuring an Energy Level"; High Molecular EL Materials—Development of Light-Emitting High Molecular Compounds; Dec. 25, 2004; pp. 64-67; Kyoritsu Shuppan, with English translation.

European Search Report (European Patent Application No. 11155124.8) dated Jun. 24, 2011, 7 pages.

* cited by examiner

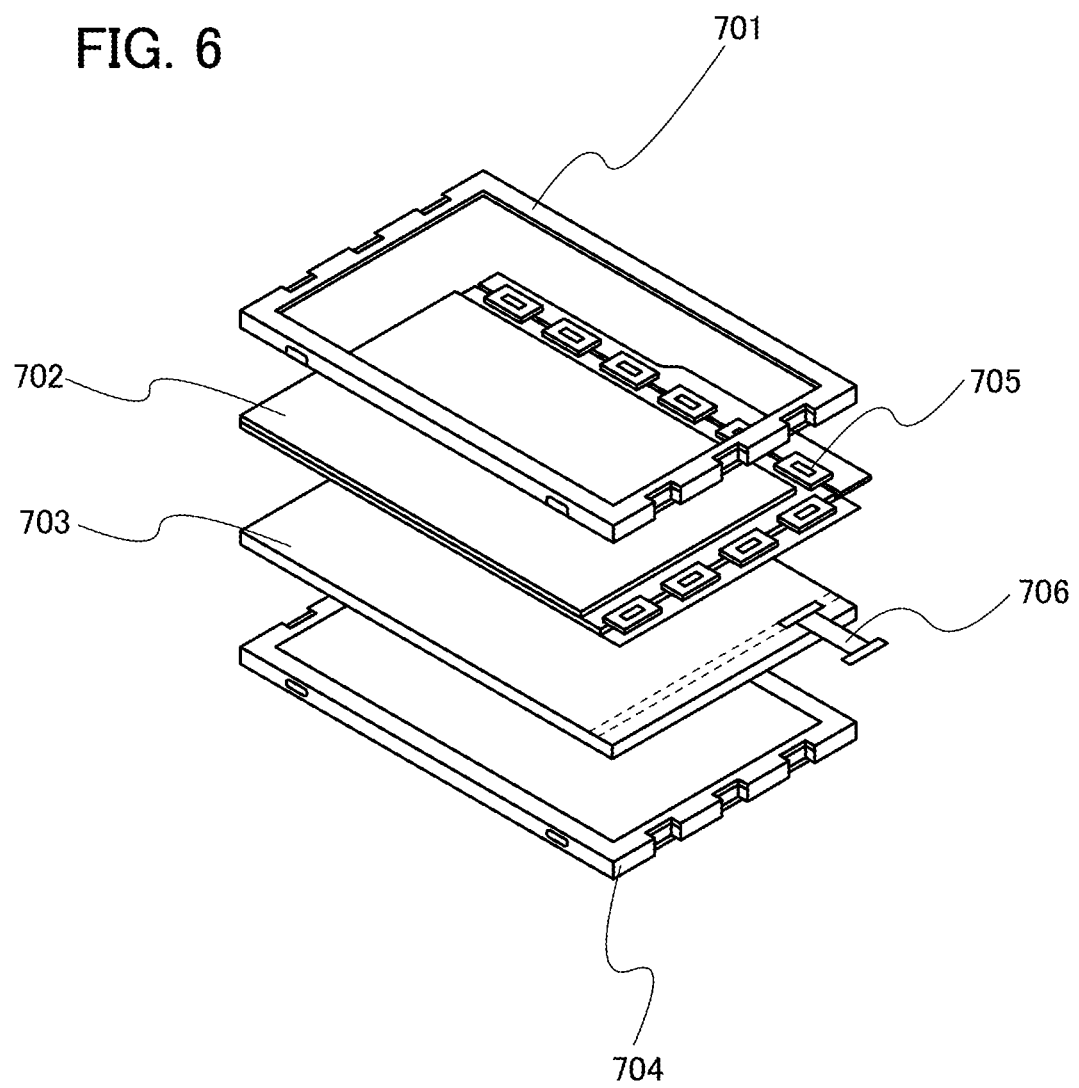

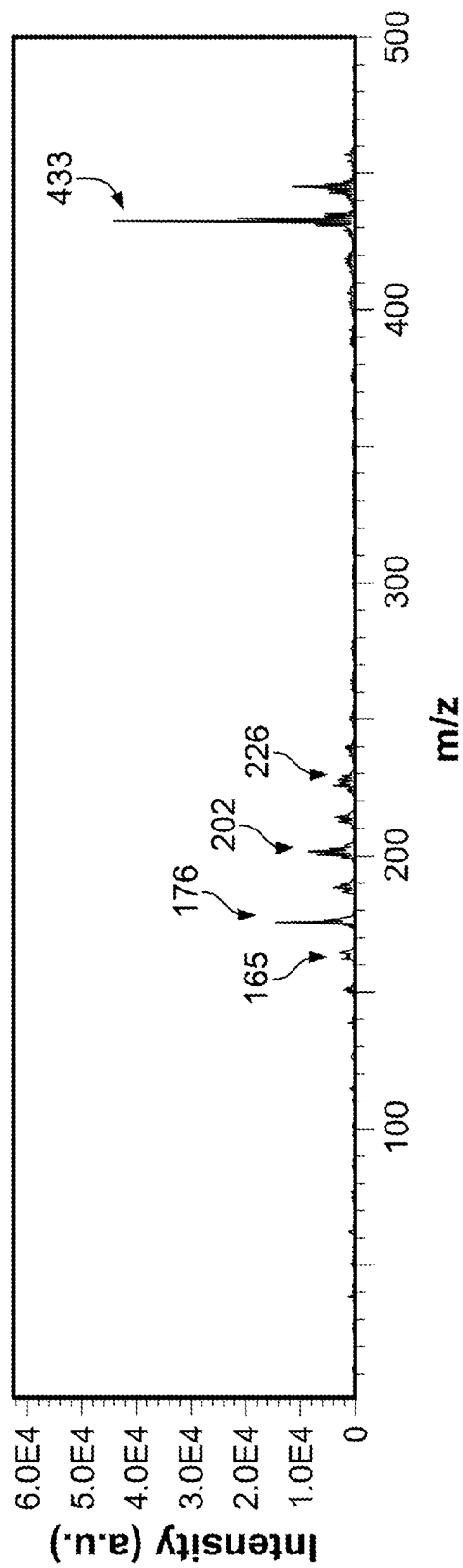
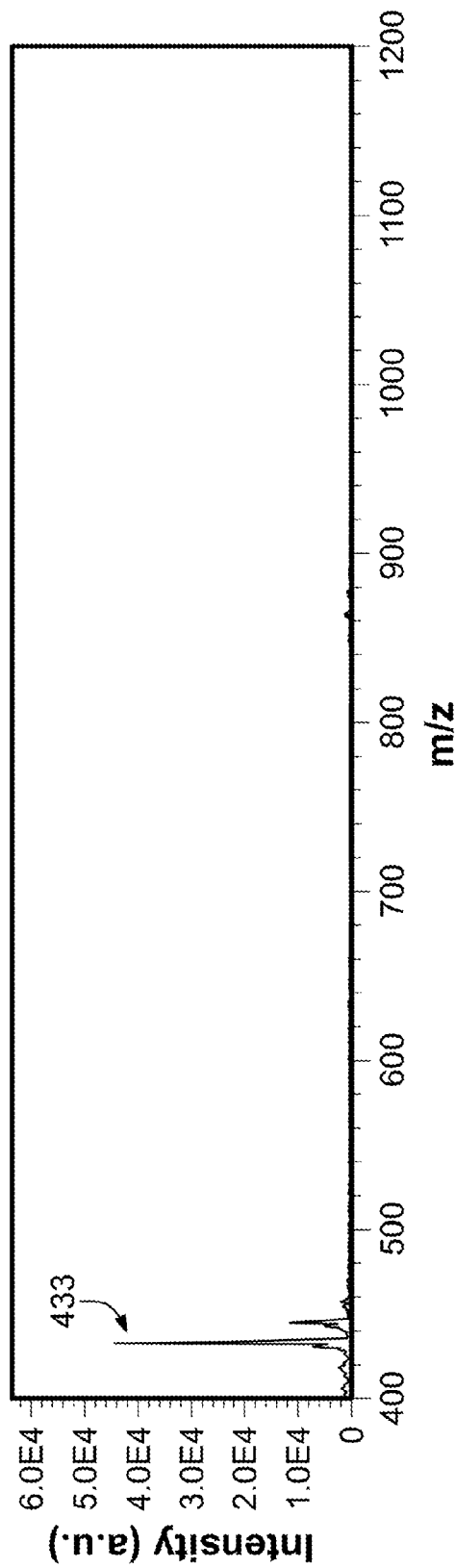
FIG. 43A
FIG. 43B

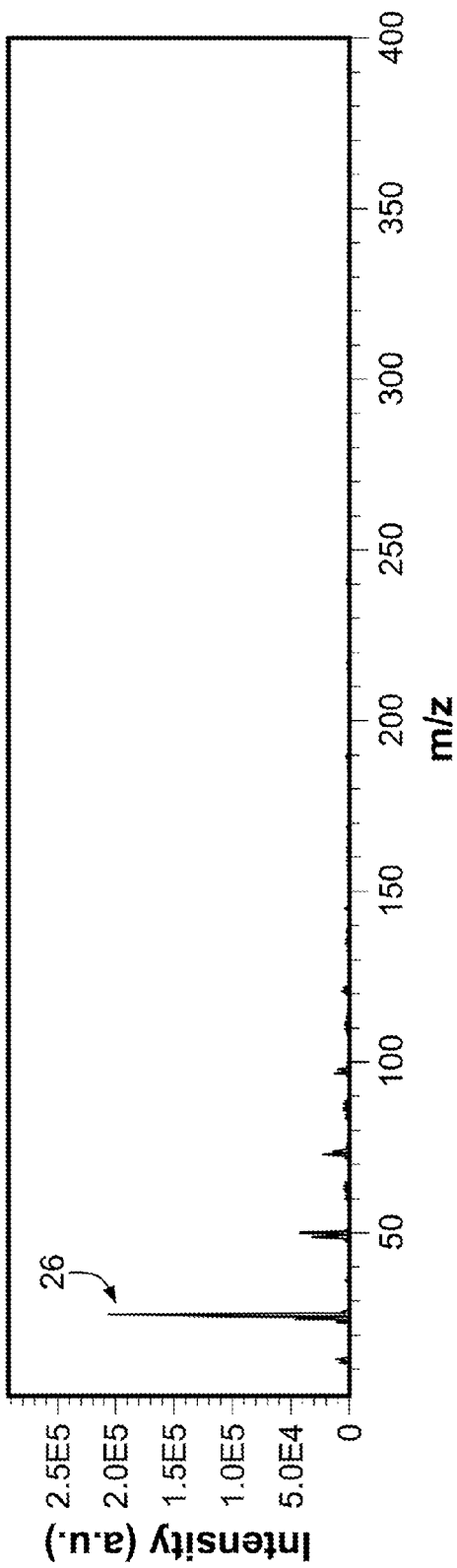
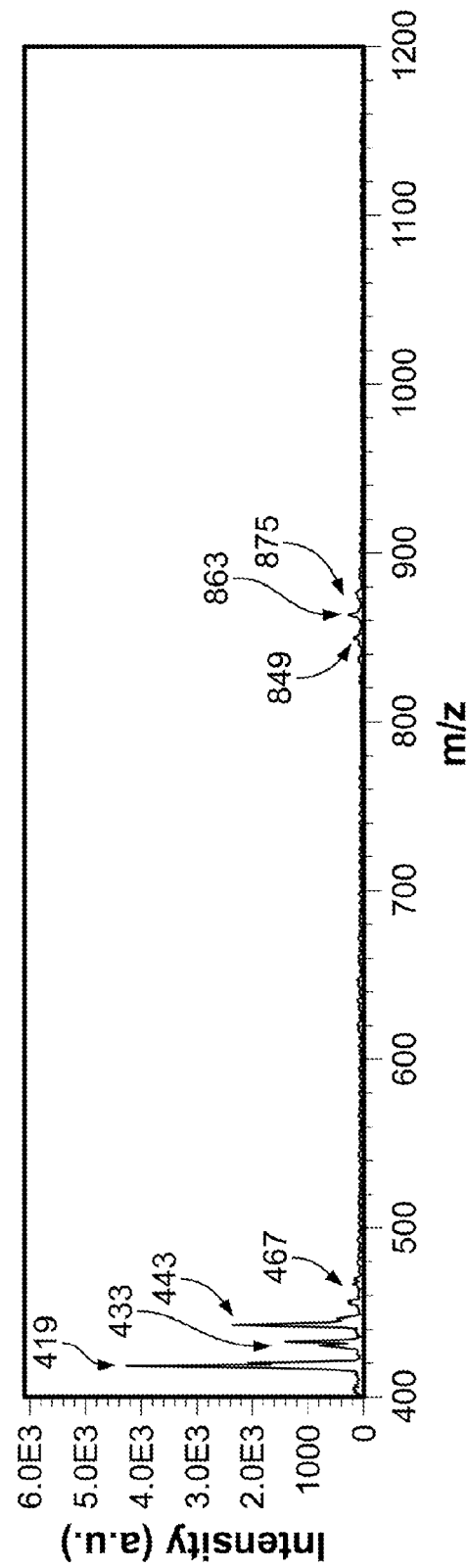

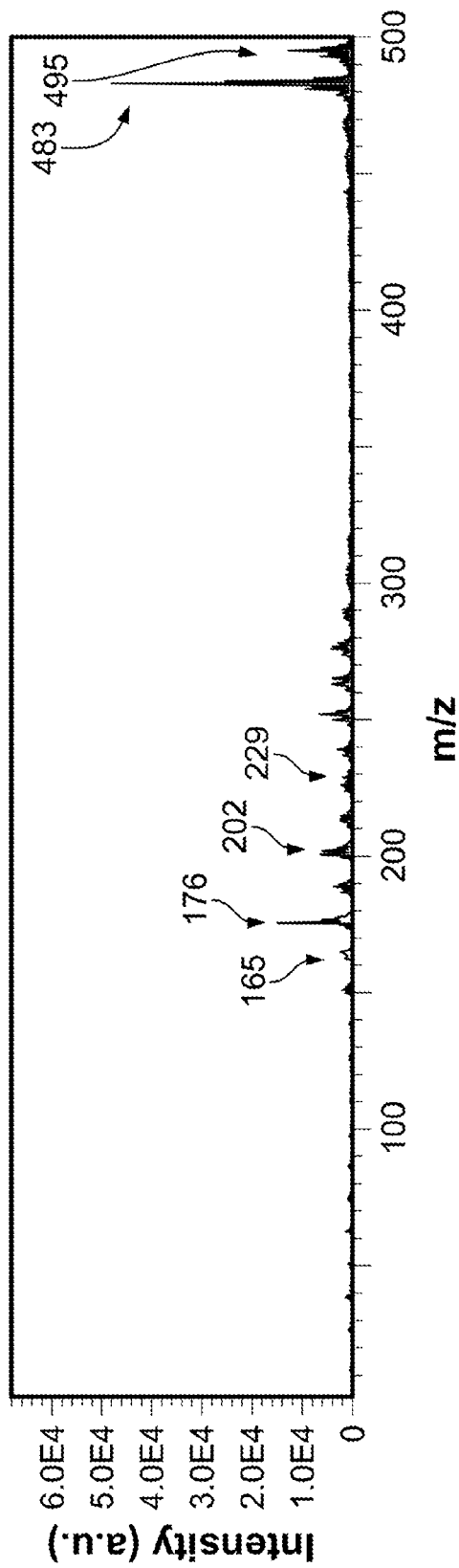
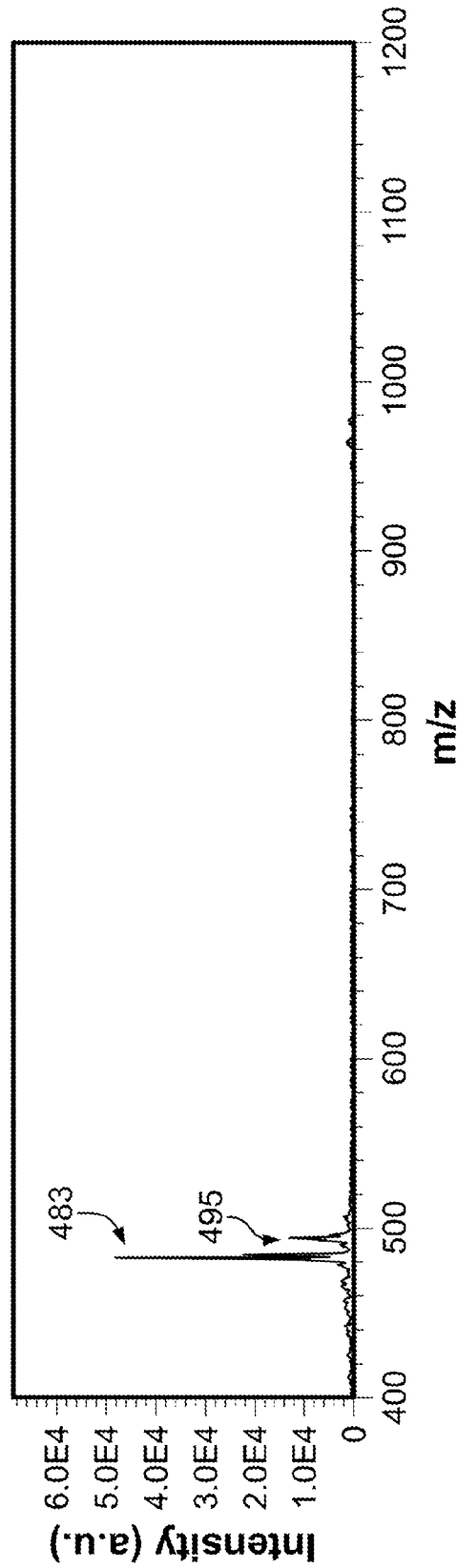
FIG. 46A
FIG. 46B

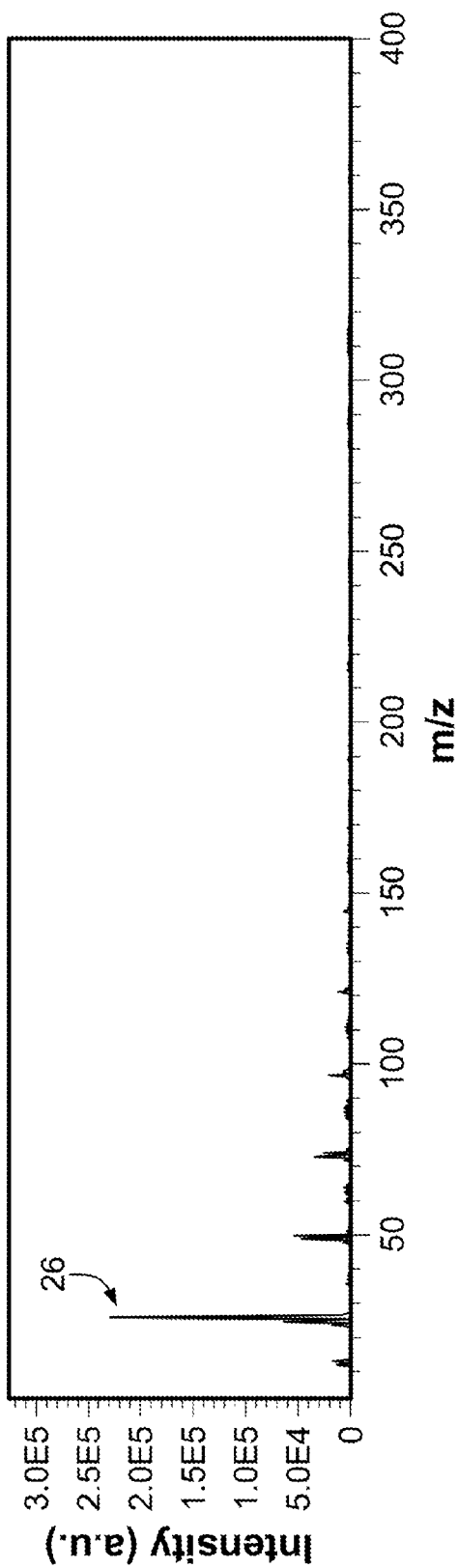

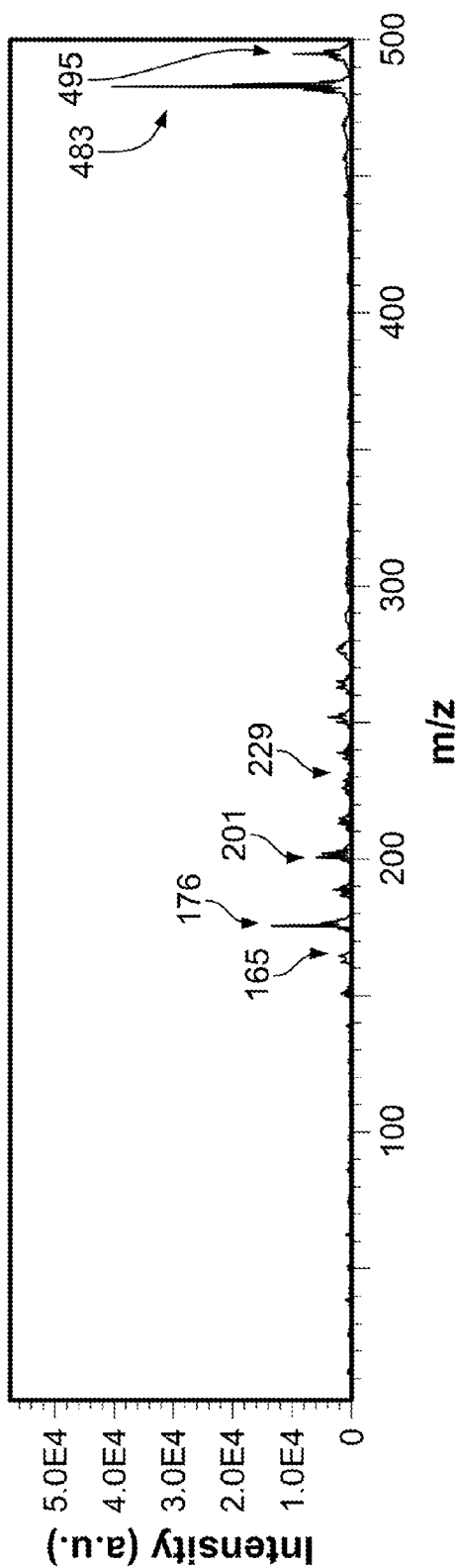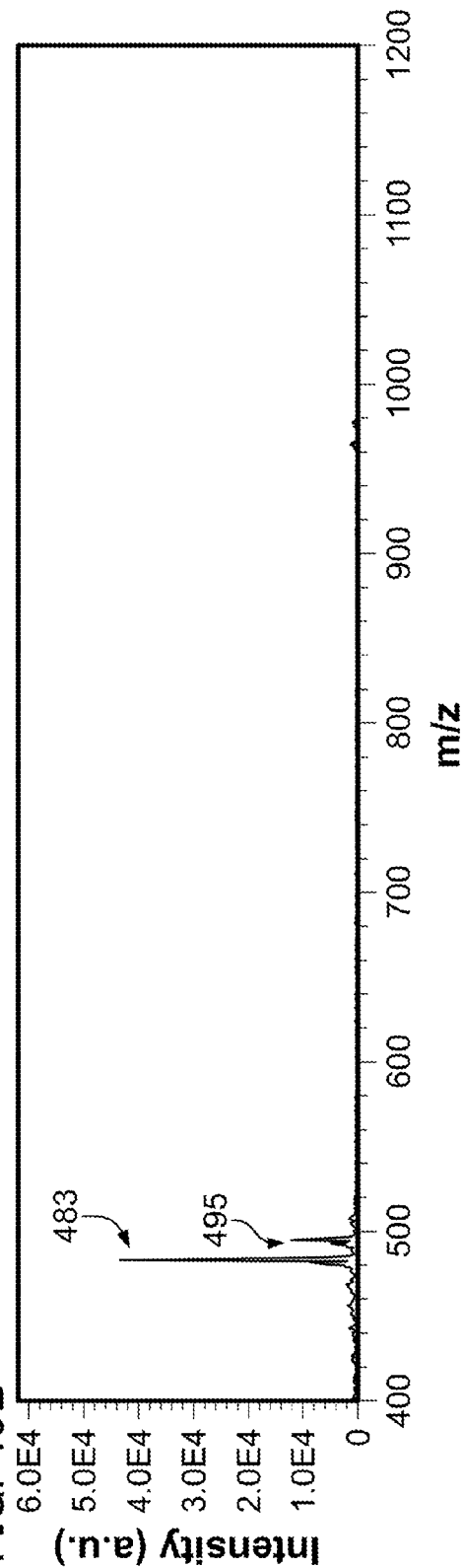
FIG. 49A
FIG. 49B

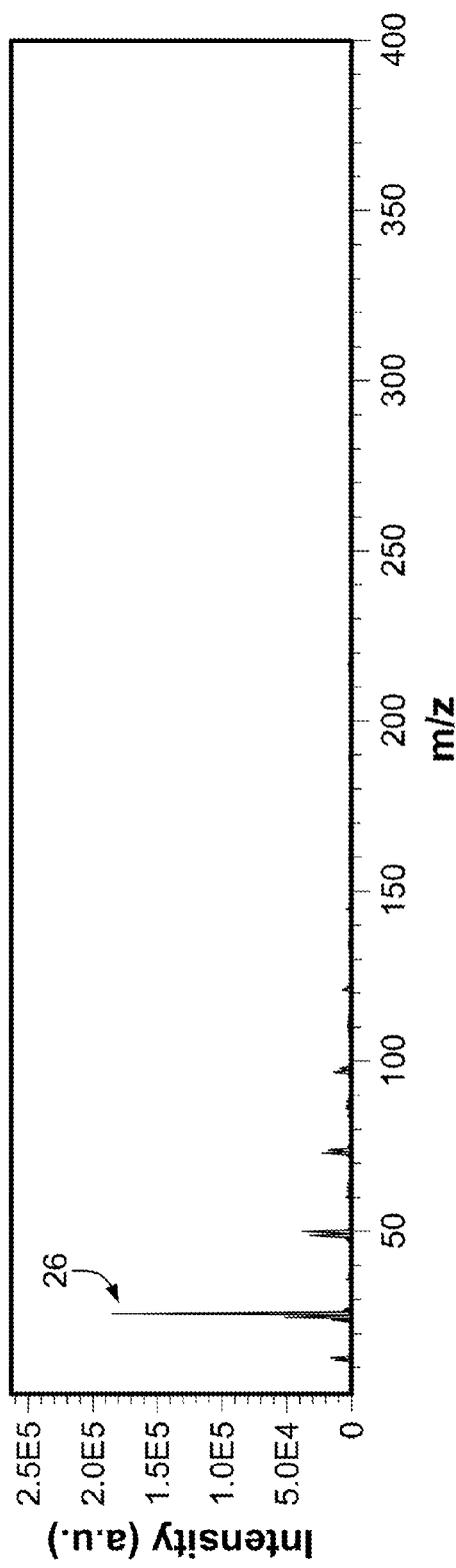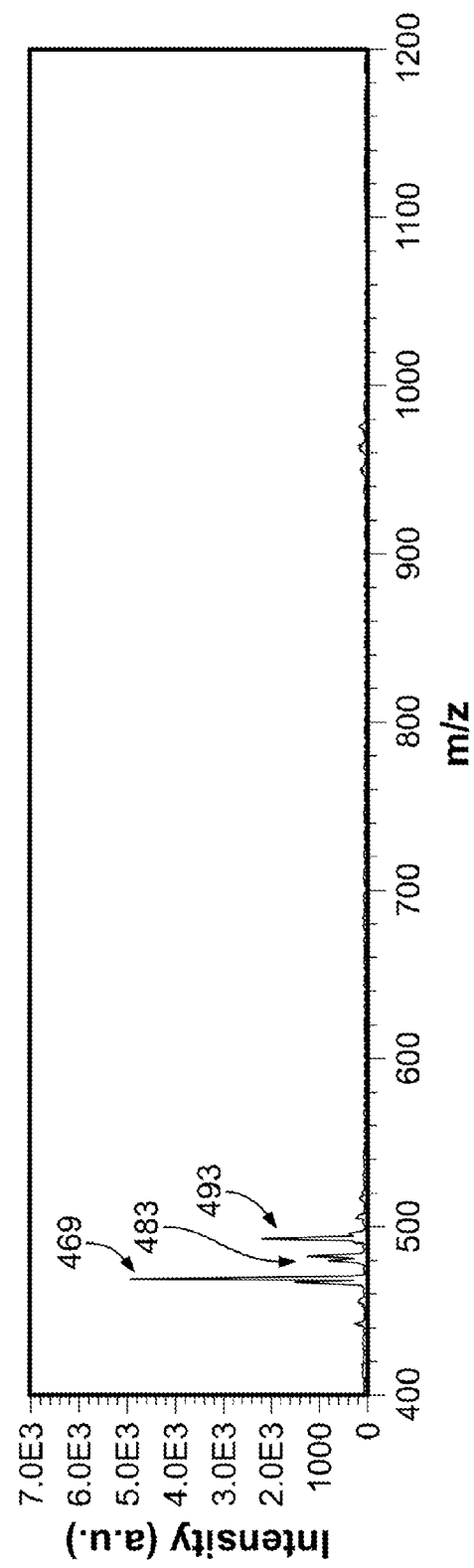

HETEROCYCLIC COMPOUND, LIGHT-EMITTING ELEMENT, LIGHT-EMITTING DEVICE, ELECTRONIC DEVICE, LIGHTING DEVICE, AND ORGANIC COMPOUND

BACKGROUND OF THE INVENTION

1. Field of the Invention

The present invention relates to a heterocyclic compound, a light-emitting element, a light-emitting device, an electronic device, and a lighting device. The invention further relates to an organic compound used in synthesis of the heterocyclic compound.

2. Description of the Related Art

In recent years, research and development have been extensively conducted on light-emitting elements using electroluminescence (EL). In a basic structure of such a light-emitting element, a layer containing a light-emitting material is interposed between a pair of electrodes. By applying voltage to this element, light emission from the light-emitting material can be obtained.

Since such a light-emitting element is of self-light-emitting type, it is considered that the light-emitting element has advantages over a liquid crystal display in that visibility of pixels is high, backlight is not required, and so on and is therefore suitable as flat panel display elements. Besides, such a light-emitting element has advantages in that it can be formed to be thin and lightweight, and has quite fast response speed.

Furthermore, such a light-emitting element can be formed in a film form, and thus can provide planar light emission. Therefore, a large-area element can be easily formed. This is a feature which is difficult to be obtained by point light sources typified by an incandescent lamp and an LED or linear light sources typified by a fluorescent lamp. Accordingly, the light-emitting element is extremely effective for use as a surface light source applicable to illumination and the like.

Light-emitting elements utilizing electroluminescence can be broadly classified according to whether a light-emitting material is an organic compound or an inorganic compound. In the case of an organic EL element in which a layer containing an organic compound used as a light-emitting material is provided between a pair of electrodes, application of voltage to the light-emitting element causes injection of electrons from a cathode and holes from an anode into the layer containing the organic compound having a light-emitting property and thus current flows. The injected electrons and holes then lead the organic compound having a light-emitting property to its excited state, whereby light emission is obtained from the excited organic compound having a light-emitting property.

Note that excited states of the organic compound include a singlet excited state and a triplet excited state. Light emission from the singlet excited state (S*) is referred to as fluorescence, and light emission from the triplet excited state (T*) is referred to as phosphorescence. In addition, the statistical generation ratio in a light-emitting element is considered to be S*:T*=1:3.

With a compound that can convert energy of a singlet excited state into light emission (hereinafter, called fluorescent compound), only light emission from the singlet excited state (fluorescence) is observed and that from the triplet excited state (phosphorescence) is not observed, at room temperature. Accordingly, the internal quantum efficiency (the ratio of generated photons to injected carriers) in a light-emitting element using a fluorescent compound is assumed to have a theoretical limit of 25%, on the basis of S*:T*=1:3.

In contrast, with a compound that can convert energy of a triplet excited state into light emission (hereinafter, called phosphorescent compound), light emission from the triplet excited state (phosphorescence) is observed. Further, since intersystem crossing (i.e., transition from a singlet excited state to a triplet excited state) easily occurs in a phosphorescent compound, the internal quantum efficiency can be theoretically increased to 100%. That is, higher emission efficiency can be achieved than using a fluorescent compound. From this reason, in order to achieve a high-efficiency light-emitting element, a light-emitting element using a phosphorescent compound has been actively developed recently.

When a light-emitting layer of a light-emitting element is formed using a phosphorescent compound described above, in order to suppress concentration quenching or quenching due to triplet-triplet annihilation of the phosphorescent compound, the light-emitting layer is often formed such that the phosphorescent compound is dispersed in a matrix of another compound. Here, the compound serving as the matrix is called host material, and the compound dispersed in the matrix, such as a phosphorescent compound, is called guest material.

When a phosphorescent compound is used as the guest material, a property required of the host material is that the host material have a greater triplet excitation energy (the difference in energy between the ground state and the triplet excited state) than that of the phosphorescent compound.

Furthermore, because the singlet excitation energy (the difference in energy between the ground state and the singlet excited state) is greater than the triplet excitation energy, a substance that has a high triplet excitation energy also has a high singlet excitation energy. Therefore, the above substance that has high triplet excitation energy is also effective in a light-emitting element using a fluorescent compound as a light-emitting material (guest material).

Studies have been conducted on compounds having dibenzo[f,h]quinoxaline rings, which are examples of the host material used when a phosphorescent compound is a guest material (e.g., see Patent Documents 1 and 2).

REFERENCE

Patent Document

[Patent Document 1] PCT International Publication No. 03/058667

[Patent Document 2] Japanese Published Patent Application No. 2007-189001

SUMMARY OF THE INVENTION

The above compounds having a dibenzo[f,h]quinoxaline ring have a planar structure, thus being easily crystallized. A light-emitting element using a compound that is easily crystallized has a short lifetime. However, if another skeleton is directly bonded to the dibenzo[f,h]quinoxaline ring so that the compound has a sterically bulky structure, the conjugated system could possibly extend to cause a decrease in triplet excitation energy.

Further, in order to achieve a light-emitting device, an electronic device, and a lighting device each having low power consumption and high reliability, a light-emitting element having a low driving voltage, a light-emitting element having high emission efficiency, or a light-emitting element having a long lifetime has been demanded.

Therefore, an object of one embodiment of the present invention is to provide a novel heterocyclic compound which can be used in a light-emitting layer of a light-emitting element as a host material in which a light-emitting material is dispersed, in particular, a novel heterocyclic compound which can be suitably used as a host material when a phosphorescent compound is used as a light-emitting material.

Another object of one embodiment of the present invention is to provide a light-emitting element having a low driving voltage. Yet another object of one embodiment of the present invention is to provide a light-emitting element having high emission efficiency. Another object of one embodiment of the present invention is to provide a light-emitting element having a long lifetime. Still another object of one embodiment of the present invention is to provide a light-emitting device, an electronic device, and a lighting device each having low power consumption by use of the above light-emitting element.

One embodiment of the present invention is a compound in which a dibenzo[f,h]quinoxaline ring and a carrier-transport skeleton are bonded to each other via an arylene groups. Further, one embodiment of the present invention is a light-emitting element containing the compound in which a dibenzo[f,h]quinoxaline ring and a carrier-transport skeleton are bonded to each other via an arylene groups.

Examples of the carrier-transport skeleton include a naphthalene skeleton, a phenanthrene skeleton, and a triphenylene skeleton A compound with a quinoxaline skeleton has a high electron-transport property, and use of such a compound for a light-emitting element enables the element to be driven at a low voltage. The compound according to one embodiment of the present invention includes a dibenzo[f,h]quinoxaline ring and a carrier-transport skeleton, thus being able to accept carriers easily. Accordingly, use of the compound as a host material in a light-emitting layer enables electrons and holes to be surely recombined in the light-emitting layer, and therefore can suppress a decrease in lifetime of a light-emitting element, allowing the element to have a long lifetime.

Moreover, in this compound, a dibenzo[f,h]quinoxaline ring and a carrier-transport skeleton are bonded to each other via an arylene group composed of a six-membered ring, such as a phenylene group or a biphenyldiyl group, so that conjugation is less likely to extend than in a compound in which a dibenzo[f,h]quinoxaline ring and a carrier-transport skeleton are directly bonded to each other. This can prevent narrowing of the band gap between the highest occupied molecular orbital level (HOMO level) and the lowest unoccupied molecular orbital level (LUMO level) or a decrease in the triplet excitation energy level (T1 level) or the singlet excitation energy level (S1 level). Accordingly, the compound according to one embodiment of the present invention can be suitably used in a light-emitting layer as a host material in which a light-emitting material is dispersed, especially as a host material in the case where a phosphorescent compound is used as a light-emitting material. In addition, by use of the heterocyclic compound, a light-emitting element having high emission efficiency can be achieved.

Furthermore, this compound tends to have a sterical structure because a dibenzo[f,h]quinoxaline ring and a carrier-transport skeleton are bonded to each other via an arylene group. The sterical structure makes a film of the compound less likely to be crystallized, thus suppressing a decrease in the T1 level or the S1 level due to stacking. This also can prevent narrowing of the band gap between the HOMO level and the LUMO level or a decrease in the T1 level or the S1 level. Accordingly, by use of the heterocyclic compound, a light-emitting element having high emission efficiency can be achieved.

A dibenzo[f,h]quinoxaline ring, a benzene skeleton included in a phenylene group or a biphenyldiyl group, and a carrier-transport skeleton such as a naphthalene skeleton, a phenanthrene skeleton, or a triphenylene skeleton are electrochemically stable. Accordingly, by use of the heterocyclic compound according to one embodiment of the present invention, which is formed using any of these skeletons, a light-emitting element having a long lifetime can be achieved.

An embodiment of the present invention is a heterocyclic compound represented by the following general formula (G1).

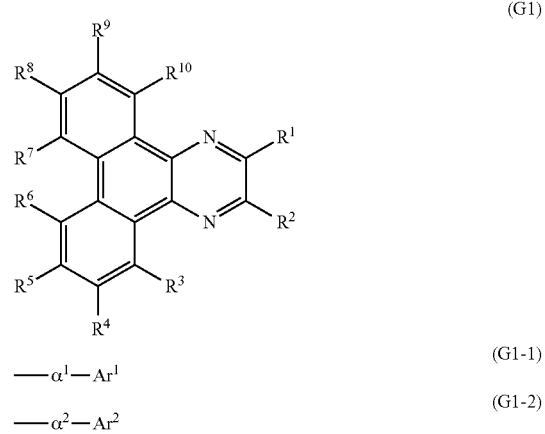

(G1)

(G1-1) —α¹—Ar¹

(G1-2) —α²—Ar²

In the general formula (G1), any one of $R^1$ to $R^{10}$ represents a substituent represented by a general formula (G1-1); another one of $R^1$ to $R^{10}$ represents hydrogen, an alkyl group having 1 to 6 carbon atoms, a substituted or unsubstituted phenyl group, a substituted or unsubstituted biphenyl group, or a substituent represented by a general formula (G1-2); and the others separately represent hydrogen, an alkyl group having 1 to 6 carbon atoms, a substituted or unsubstituted phenyl group, or a substituted or unsubstituted biphenyl group. Further, $\alpha^1$ in the general formula (G1-1) and $\alpha^2$ in the general formula (G1-2) separately represent a substituted or unsubstituted phenylene group or a substituted or unsubstituted biphenyldiyl group, and $Ar^1$ in the general formula (G1-1) and $Ar^2$ in the general formula (G1-2) separately represent a substituted or unsubstituted naphthyl group, a substituted or unsubstituted phenanthryl group, or a substituted or unsubstituted triphenylenyl group.

According to one embodiment of the present invention, in the case where any of the phenylene group and the biphenyldiyl group represented by $\alpha^1$ and $\alpha^2$ has a substituent, the substituent is an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, or a substituted or unsubstituted triphenylenyl group. In addition, in the case where any of the phenyl group, the biphenyl group, the naphthyl group, the phenanthryl group, and the triphenylenyl group has a substituent, the substituent is an alkyl group having 1 to 6 carbon atoms, a phenyl group, or a biphenyl group.

According to one embodiment of the present invention, in the case where any of the naphthyl group, the phenanthryl group, and the triphenylenyl group represented by $Ar^1$ and $Ar^2$ has a substituent, the substituent is an alkyl group having 1 to 6 carbon atoms, a phenyl group, or a biphenyl group.

In one embodiment of the present invention, in the case where any of $R^1$ to $R^{10}$ represents a phenyl group or a biphenyl group, the phenyl group or the biphenyl group may have an alkyl group having 1 to 6 carbon atoms as a substituent.

Another embodiment of the present invention is a heterocyclic compound represented by the following general formula (G2-1).

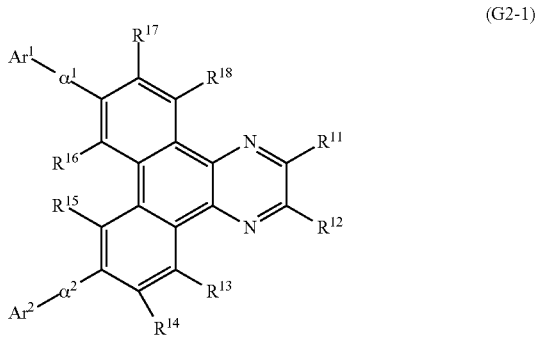

(G2-1)

In the general formula (G2-1), $R^{11}$ to $R^{18}$ separately represent hydrogen, an alkyl group having 1 to 6 carbon atoms, a substituted or unsubstituted phenyl group, or a substituted or unsubstituted biphenyl group. Further, $\alpha^1$ and $\alpha^2$ separately represent a substituted or unsubstituted phenylene group or a substituted or unsubstituted biphenyldiyl group, and $Ar^1$ and $Ar^2$ separately represent a substituted or unsubstituted naphthyl group, a substituted or unsubstituted phenanthryl group, or a substituted or unsubstituted triphenylenyl group.

In the general formula (G2-1), in the case where any of $R^{11}$ to $R^{18}$ represents a phenyl group or a biphenyl group, the phenyl group or the biphenyl group may have an alkyl group having 1 to 6 carbon atoms as a substituent.

Another embodiment of the present invention is a heterocyclic compound represented by the following general formula (G2-2).

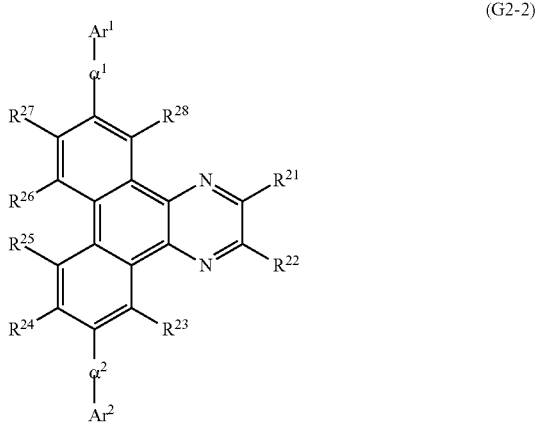

(G2-2)

In the general formula (G2-2), $R^{21}$ to $R^{28}$ separately represent hydrogen, an alkyl group having 1 to 6 carbon atoms, a substituted or unsubstituted phenyl group, or a substituted or unsubstituted biphenyl group. Further, $\alpha^1$ and $\alpha^2$ separately represent a substituted or unsubstituted phenylene group or a substituted or unsubstituted biphenyldiyl group, and $Ar^1$ and $Ar^2$ separately represent a substituted or unsubstituted naphthyl group, a substituted or unsubstituted phenanthryl group, or a substituted or unsubstituted triphenylenyl group.

In the general formula (G2-2), in the case where any of $R^{21}$ to $R^{28}$ represents a phenyl group or a biphenyl group, the phenyl group or the biphenyl group may have an alkyl group having 1 to 6 carbon atoms as a substituent.

Another embodiment of the present invention is a heterocyclic compound represented by the following general formula (G1).

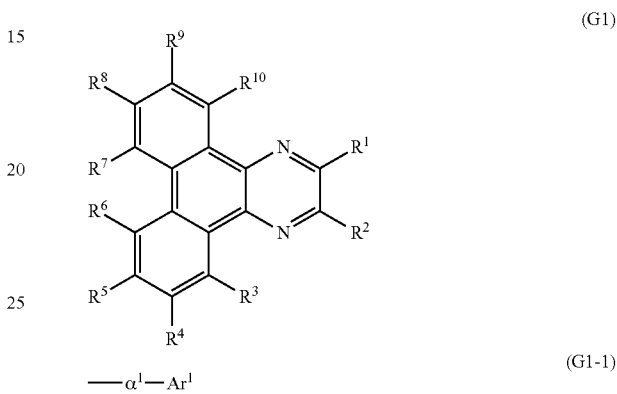

(G1)

(G1-1)

In the general formula (G1), any one of $R^1$ to $R^{10}$ represents a substituent represented by a general formula (G1-1); and the others separately represent hydrogen, an alkyl group having 1 to 6 carbon atoms, a substituted or unsubstituted phenyl group, or a substituted or unsubstituted biphenyl group. Further, in the general formula (G1-1), $\alpha^1$ represents a substituted or unsubstituted phenylene group or a substituted or unsubstituted biphenyldiyl group, and $Ar^1$ represents a substituted or unsubstituted naphthyl group, a substituted or unsubstituted phenanthryl group, or a substituted or unsubstituted triphenylenyl group.

Another embodiment of the present invention is a heterocyclic compound represented by the following general formula (G3).

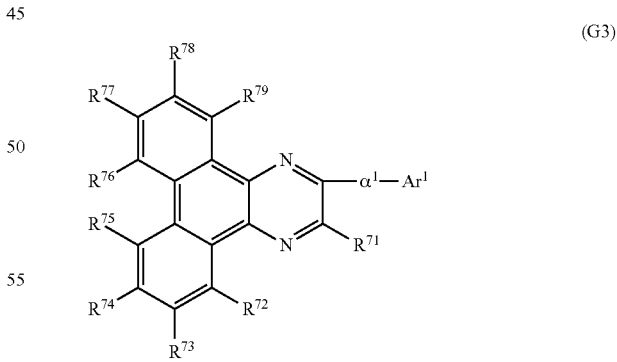

(G3)

In the general formula (G3), $R^{71}$ to $R^{79}$ separately represent hydrogen, an alkyl group having 1 to 6 carbon atoms, a substituted or unsubstituted phenyl group, or a substituted or unsubstituted biphenyl group. Further, $\alpha^1$ represents a substituted or unsubstituted phenylene group or a substituted or unsubstituted biphenyldiyl group, and $Ar^1$ represents a substituted or unsubstituted naphthyl group, a substituted or unsubstituted phenanthryl group, or a substituted or unsubstituted triphenylenyl group.

In the general formula (G3), in the case where any of $R^{71}$ to $R^{79}$ represents a phenyl group or a biphenyl group, the phenyl group or the biphenyl group may have an alkyl group having 1 to 6 carbon atoms as a substituent.

It is preferable that $\alpha^1$ in the general formula (G1-1), $\alpha^2$ in the general formula (G1-2), $\alpha^1$ and $\alpha^2$ in the general formulas (G2-1) and (G2-2), and $\alpha^1$ in the general formula (G3) be separately represented by a general formula ($\alpha$-1) or a general formula ($\alpha$-2).

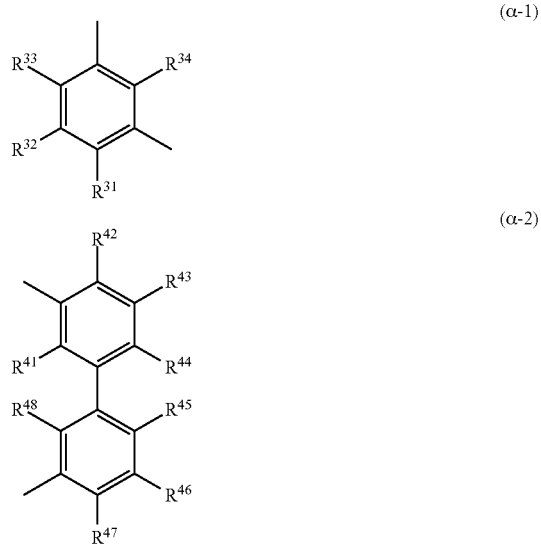

Note that $R^{31}$ to $R^{34}$ in the general formula ($\alpha$-1) and $R^{41}$ to $R^{48}$ in the general formula ($\alpha$-2) separately represent hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, or a substituted or unsubstituted triphenylenyl group.

In the case where any of $R^{31}$ to $R^{34}$ in the general formula ($\alpha$-1) and $R^{41}$ to $R^{48}$ in the general formula ($\alpha$-2) represents a phenyl group, a biphenyl group, a naphthyl group, a phenanthryl group, or a triphenylenyl group, the phenyl group, the biphenyl group, the naphthyl group, the phenanthryl group, or the triphenylenyl group may have an alkyl group having 1 to 6 carbon atoms, a phenyl group, or a biphenyl group as a substituent.

It is preferable that $Ar^1$ in the general formula (G1-1), $Ar^2$ in the general formula (G1-2), $Ar^1$ and $Ar^2$ in the general formulas (G2-1) and (G2-2), and $Ar^1$ in the general formula (G3) be represented by a general formula (Ar-1).

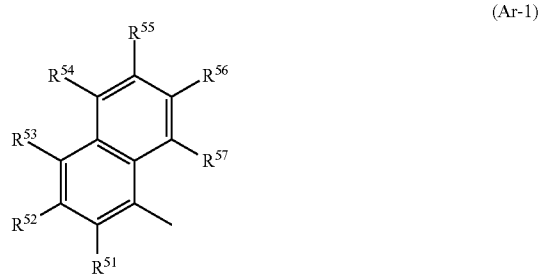

In the general formula (Ar-1), $R^{51}$ to $R^{57}$ separately represent hydrogen, an alkyl group having 1 to 6 carbon atoms, a substituted or unsubstituted phenyl group, or a substituted or unsubstituted biphenyl group.

Further, in the general formula (Ar-1), in the case where any of $R^{51}$ to $R^{57}$ represents a phenyl group or a biphenyl group, the phenyl group or the biphenyl group may have an alkyl group having 1 to 6 carbon atoms as a substituent.

Alternatively, it is preferable that $Ar^1$ in the general formula (G1-1), $Ar^2$ in the general formula (G1-2), $Ar^1$ and $Ar^2$ in the general formulas (G2-1) and (G2-2), and $Ar^1$ in the general formula (G3) be represented by a general formula (Ar-2).

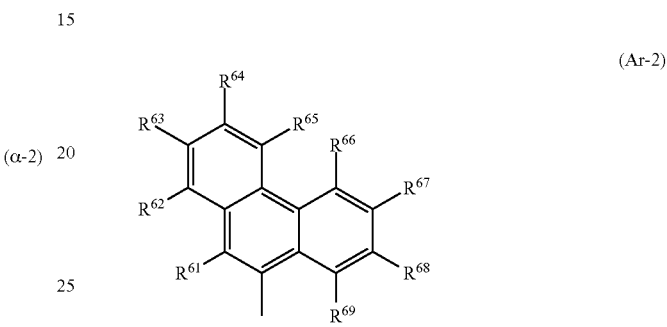

In the general formula (Ar-2), $R^{61}$ to $R^{69}$ separately represent hydrogen, an alkyl group having 1 to 6 carbon atoms, a substituted or unsubstituted phenyl group, or a substituted or unsubstituted biphenyl group.

Further, in the general formula (Ar-2), in the case where any of $R^{61}$ to $R^{69}$ represents a phenyl group or a biphenyl group, the phenyl group or the biphenyl group may have an alkyl group having 1 to 6 carbon atoms as a substituent.

Another embodiment of the present invention is a light-emitting element containing the above-described heterocyclic compound. Particularly preferred is a light-emitting element including a light-emitting layer between an anode and a cathode, in which the light-emitting layer contains a light-emitting material and the heterocyclic compound according to one embodiment of the present invention.

Further preferred is a light-emitting element including a light-emitting layer between an anode and a cathode, in which the light-emitting layer contains a light-emitting material, an electron-transport compound, and a hole-transport compound. The electron-transport compound is the heterocyclic compound according to one embodiment of the present invention. The hole-transport compound has a higher hole-transport property than the electron-transport compound and includes a carbazole skeleton, a triarylamine skeleton, a dibenzothiophene skeleton, or a dibenzofuran skeleton.

Here, a layer in contact with the light-emitting layer on the anode side preferably contains the same hole-transport compound as the light-emitting layer.

In the above light-emitting element, a layer in contact with the light-emitting layer on the cathode side preferably contains the heterocyclic compound according to one embodiment of the present invention.

Another embodiment of the present invention is a light-emitting device including the above-described light-emitting element in a light-emitting portion. Another embodiment of the present invention is an electronic device including the light-emitting device in a display portion. Another embodiment of the present invention is a lighting device including the light-emitting device in a light-emitting portion.

A light-emitting element containing the heterocyclic compound according to one embodiment of the present invention has a low driving voltage, high emission efficiency, or a long lifetime, and thus can provide a light-emitting device with low power consumption. For a similar reason, an electronic device and a lighting device with low power consumption can be provided by employing one embodiment of the present invention.

The light-emitting device in this specification covers an image display device using a light-emitting element and also the following devices: a module including a light-emitting element to which a connector such as an anisotropic conductive film, a TAB (tape automated bonding) tape, or a TCP (tape carrier package) is attached; a module in which the top of a TAB tape or a TCP is provided with a printed wiring board; a module in which an IC (integrated circuit) is directly mounted on a light-emitting element by a COG (chip on glass) technique; and further a light-emitting device used for a lighting device and the like.

An organic compound represented by a structural formula (900), which is used in synthesis of the heterocyclic compound according to one embodiment of the present invention, is also one embodiment of the present invention.

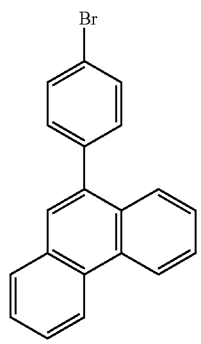

(900)

An organic compound represented by a structural formula (901), which is used in synthesis of the heterocyclic compound according to one embodiment of the present invention, is also one embodiment of the present invention.

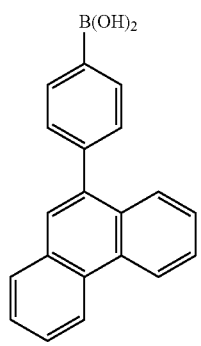

(901)

One embodiment of the present invention can provide a heterocyclic compound which can be used in a light-emitting layer of a light-emitting element as a host material in which a light-emitting material is dispersed. Another embodiment of the present invention can provide a light-emitting element having a low driving voltage. Yet another embodiment of the present invention can provide a light-emitting element having high emission efficiency. Still another embodiment of the present invention can provide a light-emitting element having a long lifetime. Still another embodiment of the present invention can provide a light-emitting device, an electronic device, and a lighting device each having low power consumption by use of the above light-emitting element.

BRIEF DESCRIPTION OF THE DRAWINGS

FIG. 6 illustrates a liquid crystal display device according to one embodiment of the present invention.

FIGS. 43A and 43B show results of TOF-SIMS measurement of NPDBq.

FIGS. 44A and 44B show results of TOF-SIMS measurement of NPDBq.

FIGS. 46A and 46B show results of TOF-SIMS measurement of mPnPDBq.

FIGS. 47A and 47B show results of TOF-SIMS measurement of mPnPDBq.

FIGS. 49A and 49B show results of TOF-SIMS measurement of DBqPPn.

FIGS. 50A and 50B show results of TOF-SIMS measurement of DBqPPn.

DETAILED DESCRIPTION OF THE INVENTION

Figure 1A:
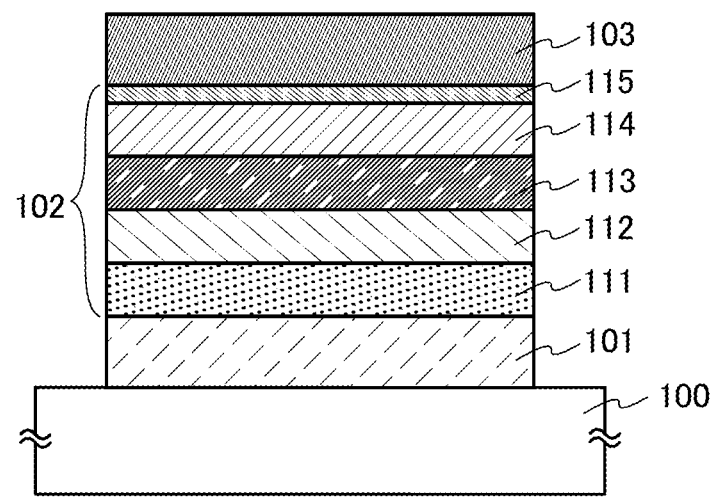
FIGS. 1A and 1B illustrate a light-emitting element according to one embodiment of the present invention.

Hereinafter, embodiments and examples of the present invention are described with reference to the drawings. Note that the invention is not limited to the following description, and it will be easily understood by those skilled in the art that various changes and modifications can be made without departing from the spirit and scope of the invention. Therefore, the invention should not be construed as being limited to the description in the following embodiments and examples.

(Embodiment 1)

Embodiment 1 shows a heterocyclic compound according to one embodiment of the present invention.

One embodiment of the present invention is a heterocyclic compound represented by a general formula (G1).

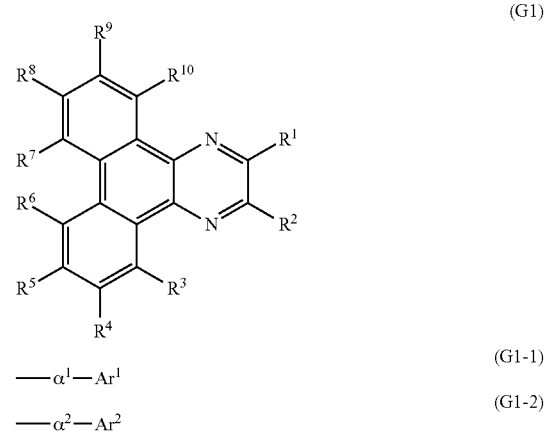

(G1)

(G1-1)
—$\alpha^1$—$Ar^1$ (G1-2)
—$\alpha^2$—$Ar^2$

In the general formula (G1), any one of $R^1$ to $R^{10}$ represents a substituent represented by a general formula (G1-1); another one of $R^1$ to $R^{10}$ represents hydrogen, an alkyl group having 1 to 6 carbon atoms, a substituted or unsubstituted phenyl group, a substituted or unsubstituted biphenyl group, or a substituent represented by a general formula (G1-2); and the others separately represent hydrogen, an alkyl group having 1 to 6 carbon atoms, a substituted or unsubstituted phenyl group, or a substituted or unsubstituted biphenyl group. Further, $\alpha^1$ in the general formula (G1-1) and $\alpha^2$ in the general formula (G1-2) separately represent a substituted or unsubstituted phenylene group or a substituted or unsubstituted biphenyldiyl group, and $Ar^1$ in the general formula (G1-1) and $Ar^2$ in the general formula (G1-2) separately represent a substituted or unsubstituted naphthyl group, a substituted or unsubstituted phenanthryl group, or a substituted or unsubstituted triphenylenyl group.

In the case where any of the phenylene group and the biphenyldiyl group represented by $\alpha^1$ in the general formula (G1-1) and $\alpha^2$ in the general formula (G1-2) has a substituent, the substituent is an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, or a substituted or unsubstituted triphenylenyl group. In addition, in the case where any of the phenyl group, the biphenyl group, the naphthyl group, the phenanthryl group, and the triphenylenyl group has a substituent, the substituent is an alkyl group having 1 to 6 carbon atoms, a phenyl group, or a biphenyl group.

In the case where any of the naphthyl group, the phenanthryl group, and the triphenylenyl group represented by $Ar^1$ in the general formula (G1-1) and $Ar^2$ in the general formula (G1-2) has a substituent, the substituent is an alkyl group having 1 to 6 carbon atoms, a phenyl group, or a biphenyl group.

In the case where any of $R^1$ to $R^{10}$ in the general formula (G1) represents a phenyl group or a biphenyl group, the phenyl group or the biphenyl group may have an alkyl group having 1 to 6 carbon atoms as a substituent.

In the general formula (G1), any one of $R^1$ to $R^{10}$ preferably represents a substituent represented by the general formula (G1-1) and another one of $R^1$ to $R^{10}$ preferably represents a substituent represented by the general formula (G1-2), because in that case the heterocyclic compound has a large molecular weight, high amorphousness, and high heat resistance.

Thus, another embodiment of the present invention is a heterocyclic compound represented by the general formula (G2-1). As in the heterocyclic compound represented by the general formula (G2-1), substituents (specifically, substituents represented by the above general formulas (G1-1) and (G1-2)) are preferably bonded to the 7- and 10-positions of the dibenzo[f,h]quinoxaline ring, because in that case the compound becomes sterical to be more highly amorphous.

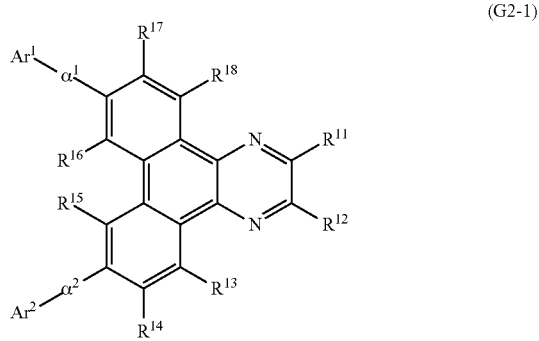

(G2-1)

In the general formula (G2-1), $R^{11}$ to $R^{18}$ separately represent hydrogen, an alkyl group having 1 to 6 carbon atoms, a substituted or unsubstituted phenyl group, or a substituted or unsubstituted biphenyl group. Further, $\alpha^1$ and $\alpha^2$ separately represent a substituted or unsubstituted phenylene group or a substituted or unsubstituted biphenyldiyl group, and $Ar^1$ and $Ar^2$ separately represent a substituted or unsubstituted naphthyl group, a substituted or unsubstituted phenanthryl group, or a substituted or unsubstituted triphenylenyl group.

In the general formula (G2-1), in the case where any of $R^{11}$ to $R^{18}$ represents a phenyl group or a biphenyl group, the phenyl group or the biphenyl group may have an alkyl group having 1 to 6 carbon atoms as a substituent.

Another embodiment of the present invention is a heterocyclic compound represented by a general formula (G2-2).

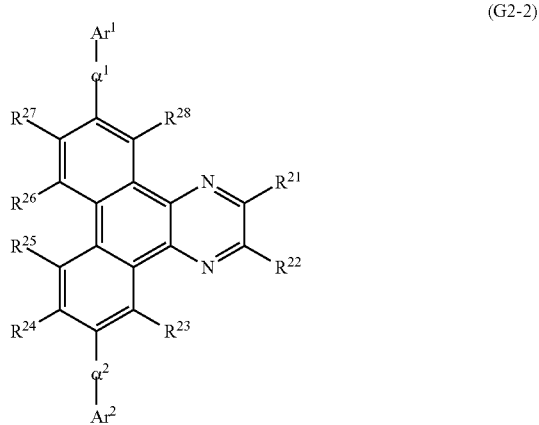

(G2-2)

In the general formula (G2-2), $R^{21}$ to $R^{28}$ separately represent hydrogen, an alkyl group having 1 to 6 carbon atoms, a substituted or unsubstituted phenyl group, or a substituted or unsubstituted biphenyl group. Further, $\alpha^1$ and $\alpha^2$ separately represent a substituted or unsubstituted phenylene group or a substituted or unsubstituted biphenyldiyl group, and $Ar^1$ and $Ar^2$ separately represent a substituted or unsubstituted naphthyl group, a substituted or unsubstituted phenanthryl group, or a substituted or unsubstituted triphenylenyl group.

In the general formula (G2-2), in the case where any of $R^{21}$ to $R^{28}$ represents a phenyl group or a biphenyl group, the phenyl group or the biphenyl group may have an alkyl group having 1 to 6 carbon atoms as a substituent.

Further, it is preferable that none of $R^1$ to $R^{10}$ in the general formula (G1) represent a substituent represented by the general formula (G1-2), because in that case the heterocyclic compound has a small molecular weight and conjugation is less likely to extend.

Thus, another embodiment of the present invention is a heterocyclic compound represented by the following general formula (G1).

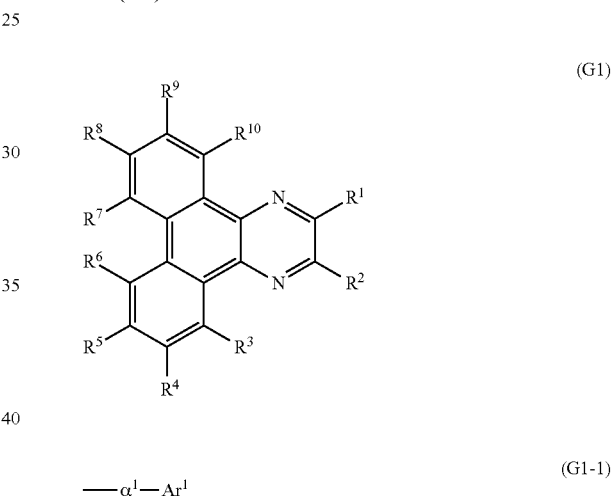

(G1)

(G1-1)

In the general formula (G1), any one of $R^1$ to $R^{10}$ represents a substituent represented by the general formula (G1-1); and the others separately represent hydrogen, an alkyl group having 1 to 6 carbon atoms, a substituted or unsubstituted phenyl group, or a substituted or unsubstituted biphenyl group. Further, in the general formula (G1-1), $\alpha^1$ represents a substituted or unsubstituted phenylene group or a substituted or unsubstituted biphenyldiyl group, and $Ar^1$ represents a substituted or unsubstituted naphthyl group, a substituted or unsubstituted phenanthryl group, or a substituted or unsubstituted triphenylenyl group.

Another embodiment of the present invention is a heterocyclic compound represented by a general formula (G3). As in the heterocyclic compound represented by the general formula (G3), a substituent (specifically, a substituent represented by the above general formulas (G1-1)) is preferably bonded to the 2-position of the dibenzo[f,h]quinoxaline ring, because in that case the carrier-transport property is improved.

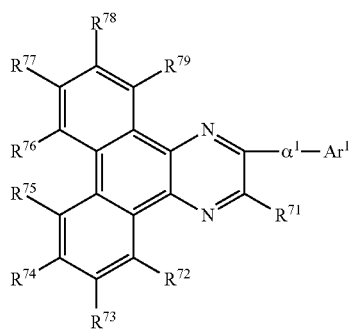

(G3)

In the general formula (G3), $R^{71}$ to $R^{79}$ separately represent hydrogen, an alkyl group having 1 to 6 carbon atoms, a substituted or unsubstituted phenyl group, or a substituted or unsubstituted biphenyl group. Further, $\alpha^1$ represents a substituted or unsubstituted phenylene group or a substituted or unsubstituted biphenyldiyl group, and $Ar^1$ represents a substituted or unsubstituted naphthyl group, a substituted or unsubstituted phenanthryl group, or a substituted or unsubstituted triphenylenyl group.

In the general formula (G3), in the case where any of $R^{71}$ to $R^{79}$ represents a phenyl group or a biphenyl group, the phenyl group or the biphenyl group may have an alkyl group having 1 to 6 carbon atoms as a substituent.

The heterocyclic compound represented by any of the general formulas (G1) to (G3) may have a substituent other than the substituents represented by the general formulas (G1-1) and (G1-2). For easy synthesis, the heterocyclic compound preferably does not have a substituent other than the substituents represented by the general formulas (G1-1) and (G1-2); for less likeliness of crystallization, the heterocyclic compound preferably has a substituent other than the substituents represented by the general formulas (G1-1) and (G1-2), because in that case the heterocyclic compound becomes more sterical. The heterocyclic compound preferably has an alkyl group as a substituent, because in that case the solubility in a solvent is increased. The heterocyclic compound preferably has an aryl group as a substituent, because in that case the carrier-transport property is improved.

In each of $\alpha^1$ in the general formula (G1-1), $\alpha^2$ in the general formula (G1-2), $\alpha^1$ and $\alpha^2$ in the general formulas (G2-1) and (G2-2), and $\alpha^1$ in the general formula (G3), the benzene skeleton is preferably para-substituted, because in that case the carrier-transport property is improved.

Alternatively, in each of $\alpha^1$ in the general formula (G1-1), $\alpha^2$ in the general formula (G1-2), $\alpha^1$ and $\alpha^2$ in the general formulas (G2-1) and (G2-2), and $\alpha^1$ in the general formula (G3), the benzene skeleton is preferably meta-substituted, because in that case conjugation is less likely to extend between substituents linked by the benzene skeleton (the dibenzo[f,h]quinoxaline ring and the carrier-transport skeleton), which results in a high T1 level, a high S1 level, or a wide bandgap between the HOMO level and the LUMO level.

Therefore, it is preferable that $\alpha^1$ in the general formula (G1-1), $\alpha^2$ in the general formula (G1-2), $\alpha^1$ and $\alpha^2$ in the general formulas (G2-1) and (G2-2), and $\alpha^1$ in the general formula (G3) be separately represented by a general formula ($\alpha$-1) or a general formula ($\alpha$-2).

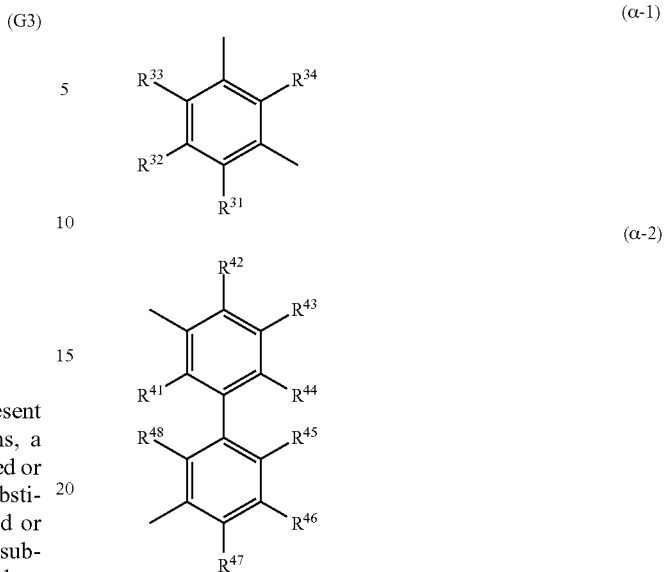

($\alpha$-1)

($\alpha$-2)

Note that $R^{31}$ to $R^{34}$ in the general formula ($\alpha$-1) and $R^{41}$ to $R^{48}$ in the general formula ($\alpha$-2) separately represent hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, or a substituted or unsubstituted triphenylenyl group.

In the case where any of $R^{31}$ to $R^{34}$ in the general formula ($\alpha$-1) and $R^{41}$ to $R^{48}$ in the general formula ($\alpha$-2) represents a phenyl group, a biphenyl group, a naphthyl group, a phenanthryl group, or a triphenylenyl group, the phenyl group, the biphenyl group, the naphthyl group, the phenanthryl group, or the triphenylenyl group may have an alkyl group having 1 to 6 carbon atoms, a phenyl group, or a biphenyl group as a substituent.

A naphthalene skeleton is a condensed ring and thus has a high carrier-transport property. In particular, the naphthalene skeleton that is a bicyclic condensed ring has a small conjugation and thus has a wide band gap, a high T1 level, and a high S1 level. Therefore, $Ar^1$ in the general formula (G1-1), $Ar^2$ in the general formula (G1-2), $Ar^1$ and $Ar^2$ in the general formulas (G2-1) and (G2-2), and $Ar^1$ in the general formula (G3) are each preferably a substituted or unsubstituted naphthyl group, specifically, a group represented by a general formula (Ar-1). In such a case, a heterocyclic compound with a high T1 level can be obtained.

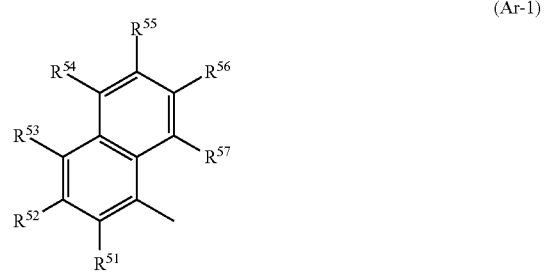

(Ar-1)

In the general formula (Ar-1), $R^{51}$ to $R^{57}$ separately represent hydrogen, an alkyl group having 1 to 6 carbon atoms, a substituted or unsubstituted phenyl group, or a substituted or unsubstituted biphenyl group.

Further, in the general formula (Ar-1), in the case where any of $R^{51}$ to $R^{57}$ represents a phenyl group or a biphenyl group, the phenyl group or the biphenyl group may have an alkyl group having 1 to 6 carbon atoms as a substituent.

As in the general formula (Ar-1), $Ar^1$ and $Ar^2$ are each preferably a substituted or unsubstituted naphthalen-1-yl group, because in that case the compound is sterical and less likely to crystallize.

A phenanthrene skeleton is a condensed ring and thus has a high carrier-transport property. Further, the heterocyclic compound has a large molecular weight, and thus has an excellent thermophysical property. In particular, the phenanthrene skeleton has a helicene structure and thus has a wide band gap, a high T1 level, and a high S1 level. Therefore, $Ar^1$ in the general formula (G1-1), $Ar^2$ in the general formula (G1-2), $Ar^1$ and $Ar^2$ in the general formulas (G2-1) and (G2-2), and $Ar^1$ in the general formula (G3) are each preferably a substituted or unsubstituted phenanthryl group, specifically, a group represented by a general formula (Ar-2). In such a case, a heterocyclic compound with a high T1 level can be obtained.

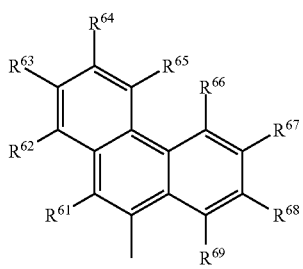

(Ar-2)

In the general formula (Ar-2), $R^{61}$ to $R^{69}$ separately represent hydrogen, an alkyl group having 1 to 6 carbon atoms, a substituted or unsubstituted phenyl group, or a substituted or unsubstituted biphenyl group.

Further, in the general formula (Ar-2), in the case where any of $R^{61}$ to $R^{69}$ represents a phenyl group or a biphenyl group, the phenyl group or the biphenyl group may have an alkyl group having 1 to 6 carbon atoms as a substituent.

Further, a triphenylene skeleton is a condensed ring and thus has a high carrier-transport property. Further, the heterocyclic compound has a large molecular weight, and thus has an excellent thermophysical property. Despite being a condensed ring with a large molecular weight, the triphenylene skeleton is preferable because it is a skeleton with a combination of helicene structures (twisted condensed ring), and thus has a wide band gap, a high T1 level, and a high S1 level. Therefore, $Ar^1$ in the general formula (G1-1), $Ar^2$ in the general formula (G1-2), $Ar^1$ and $Ar^2$ in the general formulas (G2-1) and (G2-2), and $Ar^1$ in the general formula (G3) are each preferably a substituted or unsubstituted triphenylenyl group. In such a case, a heterocyclic compound with a high T1 level can be obtained.

In each of the above-described general formulas, $\alpha^1$ and $\alpha^2$ separately represent a substituted or unsubstituted phenylene group or a substituted or unsubstituted biphenyldiyl group. The phenylene group or the biphenyldiyl group may have an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, or a substituted or unsubstituted triphenylenyl group as a substituent.

All the phenylene groups included in $\alpha^1$ and $\alpha^2$ are preferably meta-substituted, because in that case the heterocyclic compound according to one embodiment of the present invention has a high T1 level. Alternatively, all the phenylene groups included in $\alpha^1$ and $\alpha^2$ are preferably para-substituted, because in that case a light-emitting element containing the heterocyclic compound according to one embodiment of the present invention can be driven at a low voltage.

Examples of specific structures of $\alpha^1$ and $\alpha^2$ are represented by structural formulas (1-1) to (1-9).

(1-1)

(1-2)

(1-3)

(1-4)

(1-5)

(1-6)

(1-7)

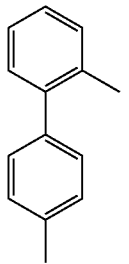

(1-8)

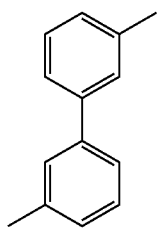

(1-9)

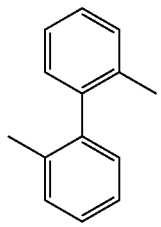

All the phenylene skeletons are preferably meta-substituted as shown in the structural formulas (1-2), (1-6), and (1-8), or all the phenylene skeletons are preferably ortho-substituted as shown in the structural formulas (1-3), (1-7), and (1-9), because in that case conjugation is unlikely to extend, so that the S1 level or T1 level can be kept high or the band gap between the HOMO level and the LUMO level can be kept wide. Further, the structure is sterical and the film quality is improved. The bonding position is particularly preferably at a meta position, because in that case the heterocyclic compound can be synthesized easily. Further, all the phenylene skeletons are preferably para-substituted as shown in the structural formulas (1-1), (1-4), and (1-5), because in that case the carrier-transport property is improved, so that the light-emitting element can be driven at a low voltage.

In the general formulas given above, $R^1$ to $R^{18}$, $R^{21}$ to $R^{28}$, $R^{51}$ to $R^{57}$, $R^{61}$ to $R^{69}$, and $R^{71}$ to $R^{79}$ separately represent hydrogen, an alkyl group having 1 to 6 carbon atoms, a substituted or unsubstituted phenyl group, or a substituted or unsubstituted biphenyl group. Examples of specific structures of $R^1$ to $R^{18}$, $R^{21}$ to $R^{28}$, $R^{51}$ to $R^{57}$, $R^{61}$ to $R^{69}$, and $R^{71}$ to $R^{79}$ include substituents represented by structural formulas (2-1) to (2-17).

(2-1)

(2-2)

(2-3)

(2-4)

(2-5)

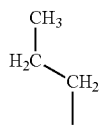

(2-6)

(2-7)

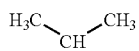

(2-8)

(2-9)

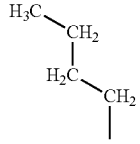

(2-10)

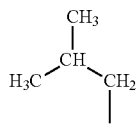

(2-11)

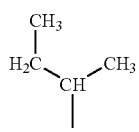

(2-12)

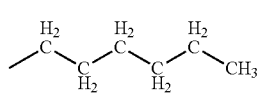

(2-13)

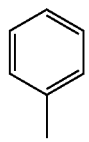

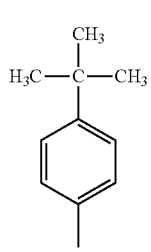

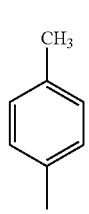

-continued

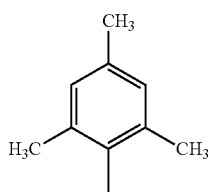 (2-14)

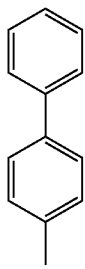 (2-15)

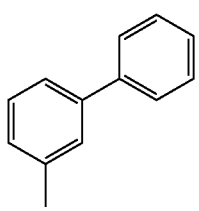 (2-16)

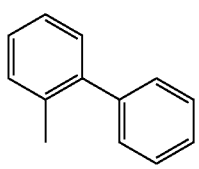 (2-17)

In the general formulas given above, $R^{31}$ to $R^{34}$ and $R^{41}$ to $R^{48}$ separately represent hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, or a substituted or unsubstituted triphenylenyl group. Examples of specific structures of $R^{31}$ to $R^{34}$ and $R^{41}$ to $R^{48}$ include substituents represented by the structural formulas (2-1) to (2-17) and structural formulas (2-18) to (2-21).

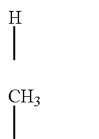 (2-1)

 (2-2)

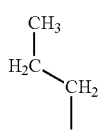 (2-3)

(2-4)

 (2-5)

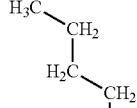 (2-6)

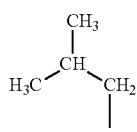 (2-7)

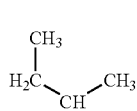 (2-8)

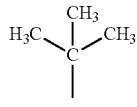 (2-9)

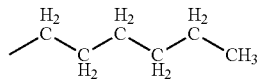 (2-10)

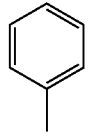 (2-11)

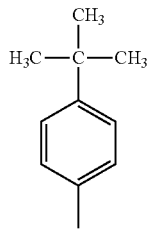 (2-12)

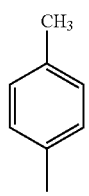 (2-13)

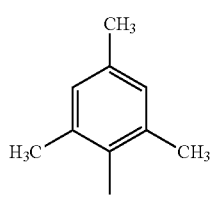 (2-14)

(2-15)
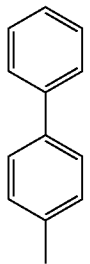
(2-16)
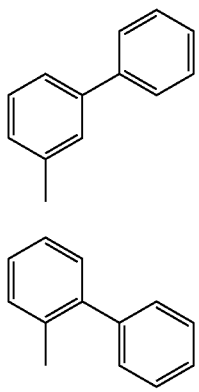
(2-17)
(2-18)
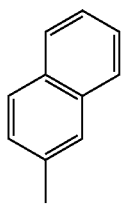
(2-19)
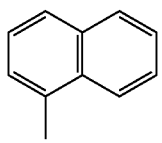
(2-20)
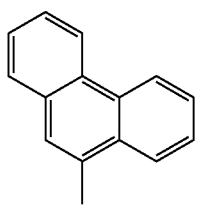
(2-21)
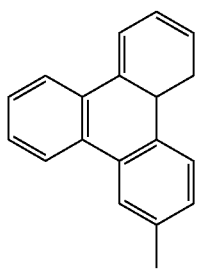
Specific examples of the heterocyclic compound represented by the general formula (G1) include, but are not limited to, heterocyclic compounds represented by structural formulas (100) to (110), (120) to (133), and (140) to (153). However, the present invention is not limited to these examples.
(100)
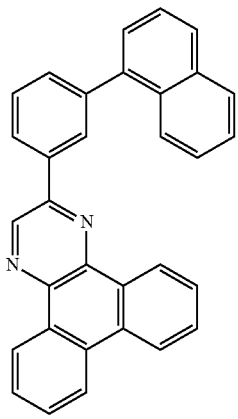
(101)
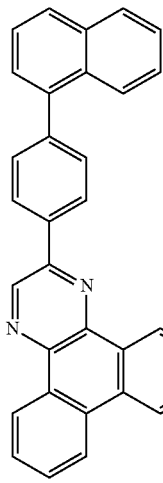
(102)
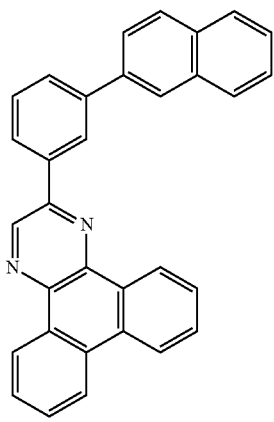

-continued
(103)
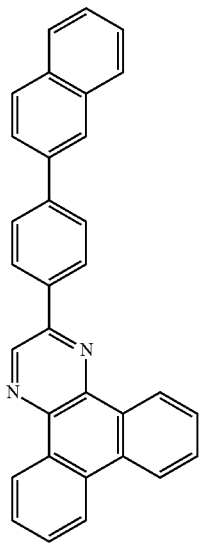
(104)
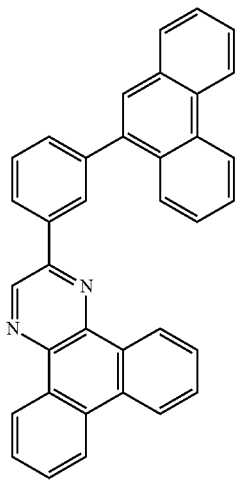
(105)
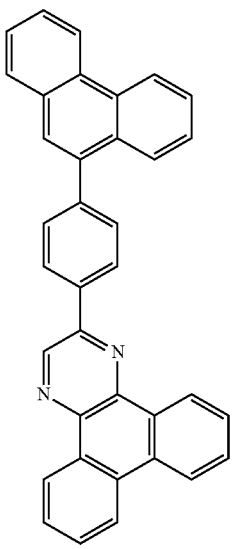
-continued
(106)
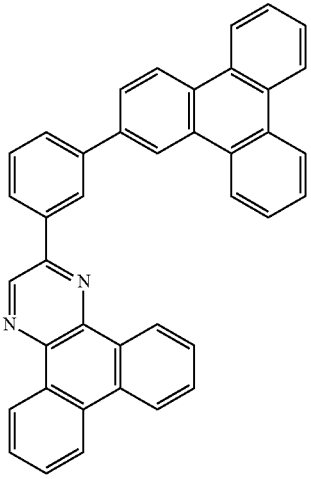
(107)
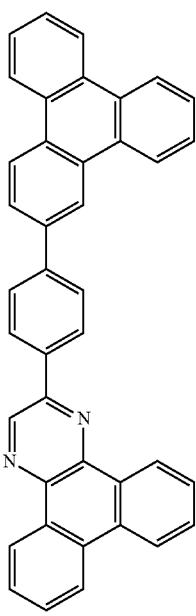
(108)
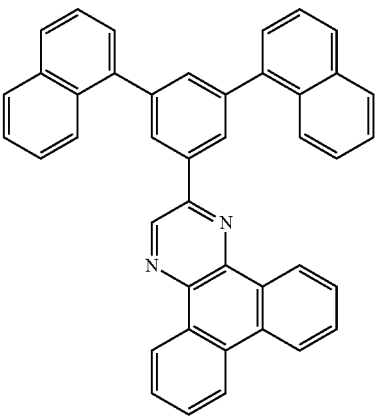

(109) 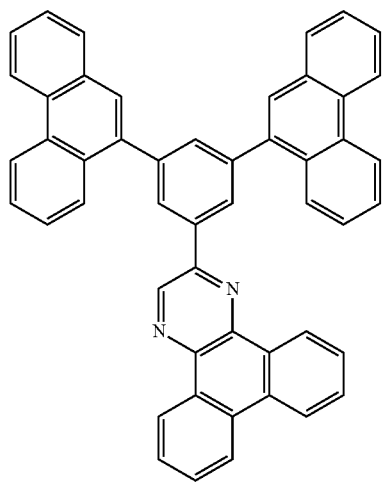
(121) 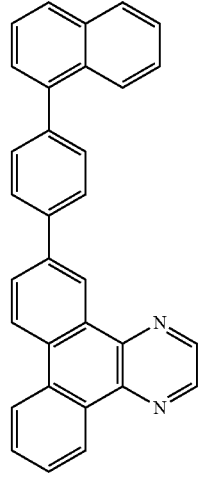
(110) 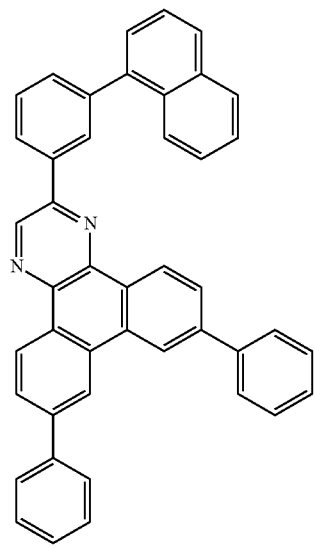
(122) 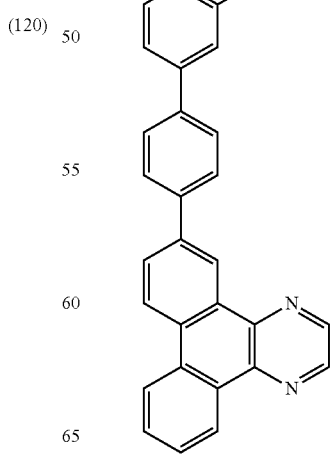
(120) 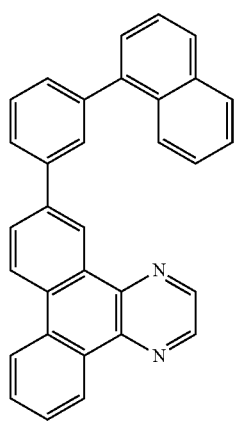
(123) 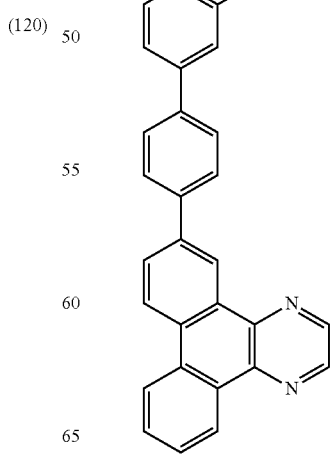

(124)
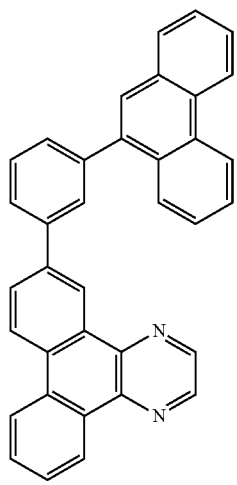
(125)
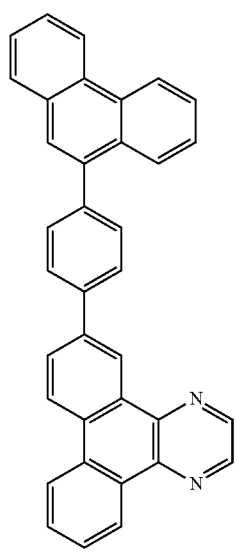
(126)
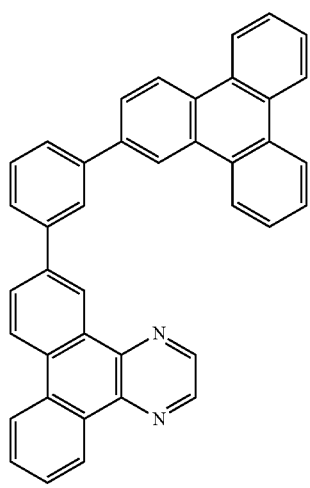
(127)
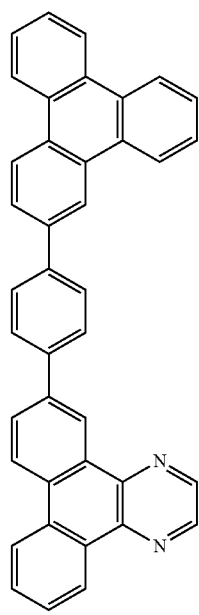
(128)
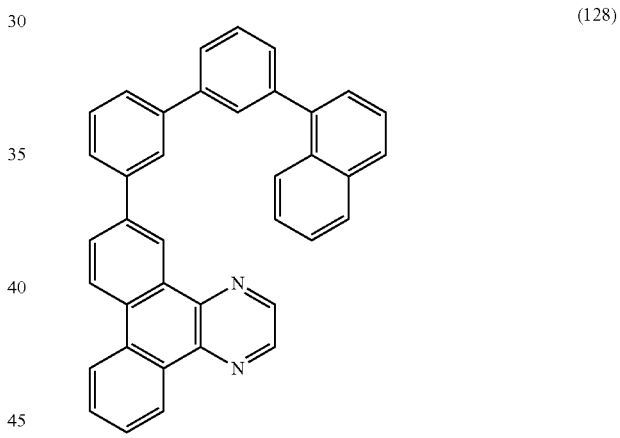
(129)
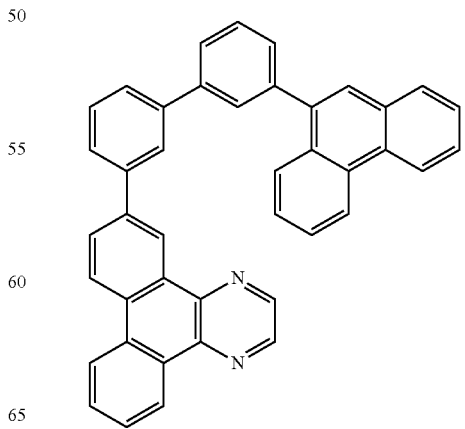

(130)
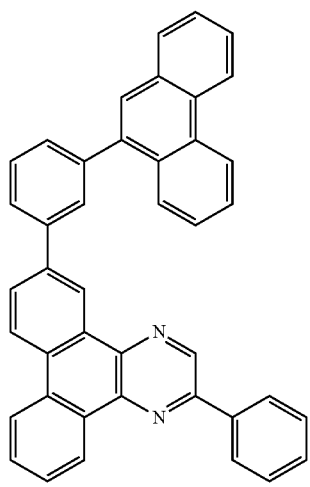
(131)
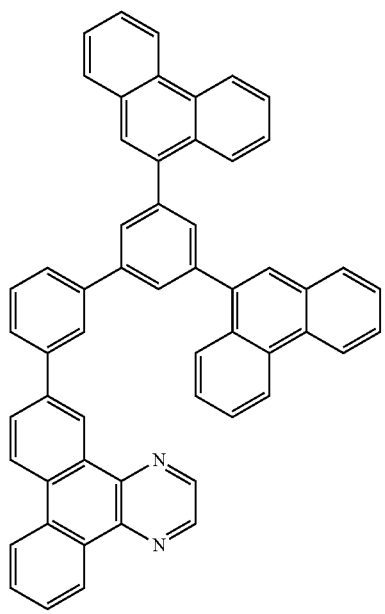
(132)
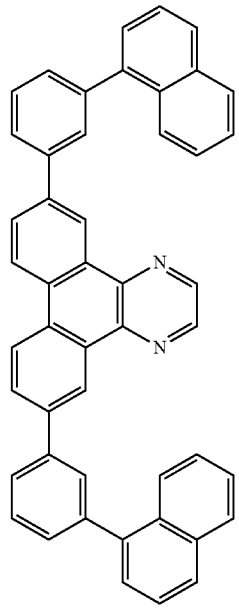
(133)
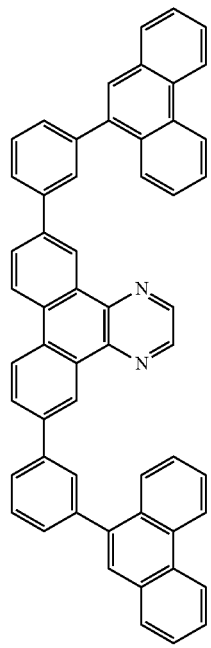

(140) 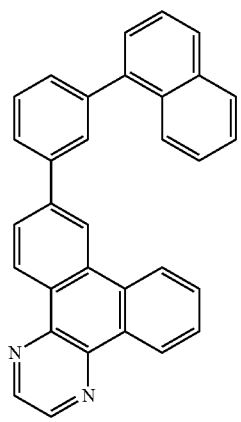
(141) 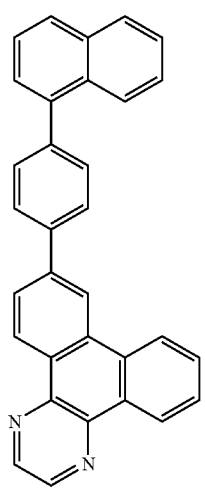
(142) 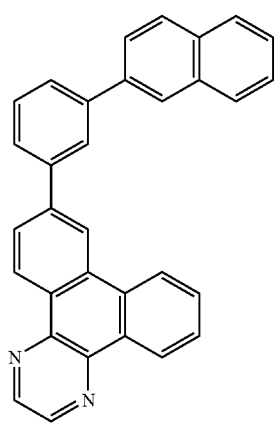
(143) 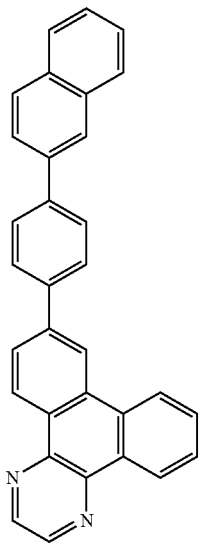
(144) 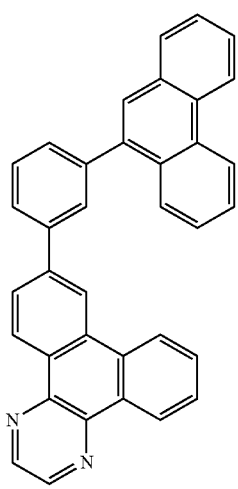
(145) 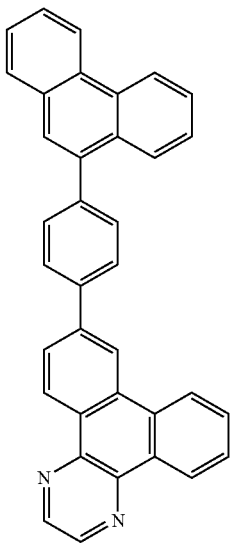

(146)
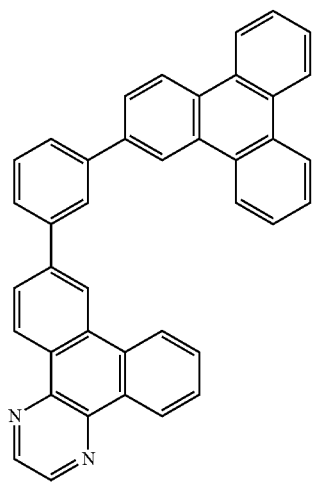
(147)
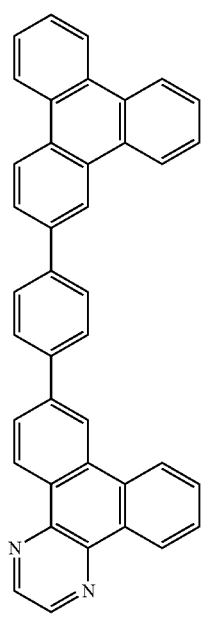
(148)
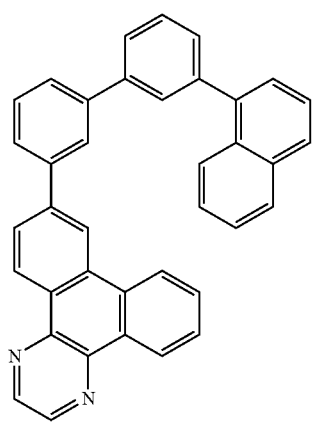
(149)
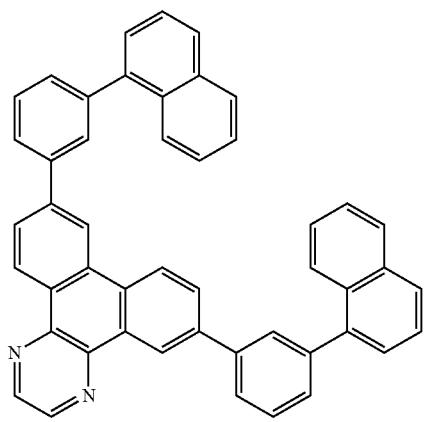
(150)
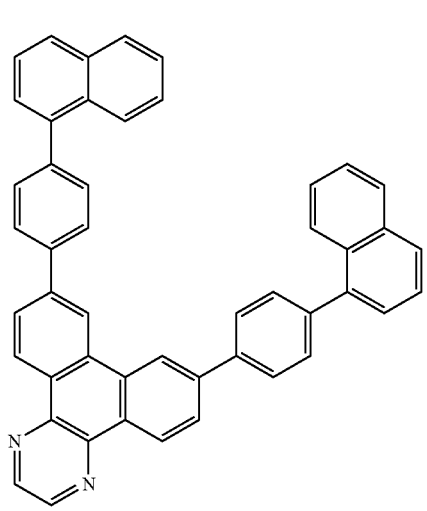
(151)
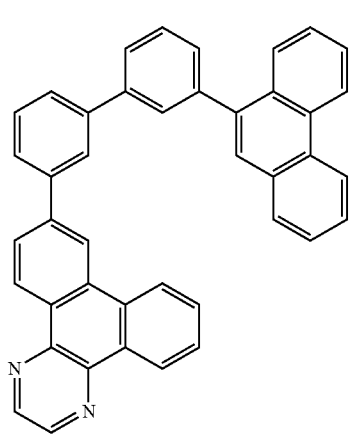

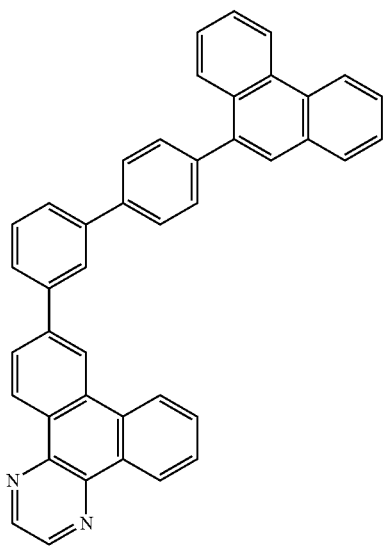

(152)

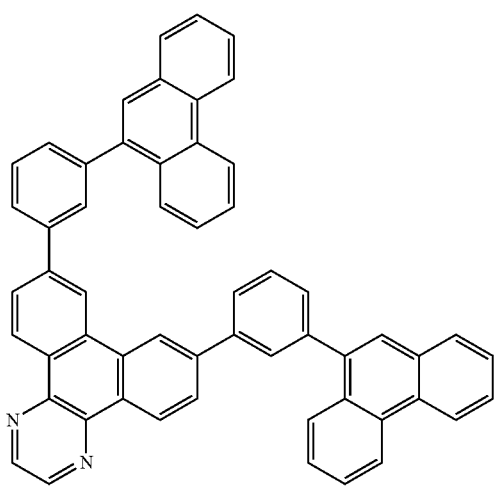

(153)

A variety of reactions can be applied to a method of synthesizing the heterocyclic compound according to one embodiment of the present invention. For example, synthesis reactions described below enable the synthesis of the heterocyclic compound according to one embodiment of the present invention represented by the general formula (G1). Note that the methods of synthesizing the heterocyclic compound according to one embodiment of the present invention are not limited to the synthesis methods below.

(Synthesis Method 1 of the Heterocyclic Compound Represented by the General Formula (G1))

As illustrated in a synthesis scheme (A-1), a halogenated dibenzoquinoxaline compound (a1) and an arylboron compound (a2) are coupled, so that the heterocyclic compound represented by the general formula (G1) can be synthesized. In particular, in the case where any one of $R^1$ to $R^{10}$ in the heterocyclic compound represented by the general formula (G1) represents a substituent represented by the general formula (G1-2), an arylboron compound (a3) shown in parenthesis in the synthesis scheme (A-1) is further used, and the halogenated dibenzoquinoxaline compound (a1), the arylboron compound (a2), and the arylboron compound (a3) are coupled, so that the heterocyclic compound represented by the general formula (G1) can be synthesized. The synthesis scheme (A-1) is illustrated below.

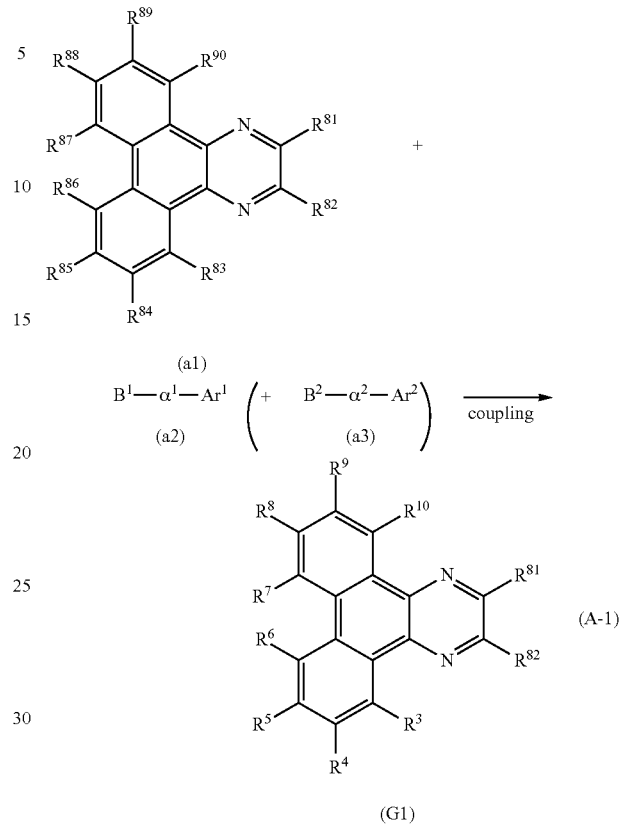

In the synthesis scheme (A-1), $\alpha^1$ and $\alpha^2$ separately represent a substituted or unsubstituted phenylene group or a substituted or unsubstituted biphenyldiyl group, and $Ar^1$ and $Ar^2$ separately represent a substituted or unsubstituted naphthyl group, a substituted or unsubstituted phenanthryl group, or a substituted or unsubstituted triphenylenyl group. Further, $B^1$ and $B^2$ separately represent a boronic acid or dialkoxyborane.

In the synthesis scheme (A-1), any one of $R^1$ to $R^{10}$ represents a substituent represented by the general formula (G1-1); another one of $R^1$ to $R^{10}$ represents hydrogen, an alkyl group having 1 to 6 carbon atoms, a substituted or unsubstituted phenyl group, a substituted or unsubstituted biphenyl group, or a substituent represented by the general formula (G1-2); and the others separately represent hydrogen, an alkyl group having 1 to 6 carbon atoms, a substituted or unsubstituted phenyl group, or a substituted or unsubstituted biphenyl group.

In the synthesis scheme (A-1), any one of $R^{81}$ to $R^{90}$ represents a substituent represented by a general formula ($\alpha$1-1); another one of $R^{81}$ to $R^{90}$ represents hydrogen, an alkyl group having 1 to 6 carbon atoms, a substituted or unsubstituted phenyl group, a substituted or unsubstituted biphenyl group, or a substituent represented by a general formula (a1-2); and the others separately represent hydrogen, an alkyl group having 1 to 6 carbon atoms, a substituted or unsubstituted phenyl group, or a substituted or unsubstituted biphenyl group.

—$X^1$ (a1-1)

—$X^2$ (a1-2)

-$\alpha^1$-$Ar^1$ (G1-1)

-$\alpha^2$-$Ar^2$ (G1-2)

$X^1$ in the general formula (a1-1) and $X^2$ in the general formula (a1-2) separately represent chlorine, bromine, or iodine. $X^1$ and $X^2$ preferably represent bromine or iodine, which has high reactivity, more preferably iodine. Further, $\alpha^1$ in the general formula (G1-1) and $\alpha^2$ in the general formula (G1-2) separately represent a substituted or unsubstituted phenylene group or a substituted or unsubstituted biphenyldiyl group, and $Ar^1$ in the general formula (G1-1) and $Ar^2$ in the general formula (G1-2) separately represent a substituted or unsubstituted naphthyl group, a substituted or unsubstituted phenanthryl group, or a substituted or unsubstituted triphenylenyl group.

In the synthesis scheme (A-1), $\alpha^1$ is bonded to a position where $X^1$ has been bonded, and $\alpha^2$ is bonded to a position where $X^2$ has been bonded.

Note that there are a variety of reaction conditions for the coupling reaction in the synthesis scheme (A-1). As an example, a synthesis method using a metal catalyst in the presence of a base can be employed.

The case where a Suzuki-Miyaura reaction is performed in the synthesis scheme (A-1) is described.

A palladium catalyst can be used as the metal catalyst, and a mixture of a palladium complex and a ligand thereof can be used as the palladium catalyst. As the palladium complex, palladium(II) acetate, tetrakis(triphenylphosphine)palladium (0), bis(triphenylphosphine)palladium(II)dichloride, and the like are given. As the ligand of the palladium complex, tri (ortho-tolyl)phosphine, triphenylphosphine, tricyclohexylphosphine, and the like are given.

In addition, as the above base, an organic base such as sodium tert-butoxide, an inorganic base such as sodium carbonate, potassium carbonate, and the like can be given.

The reaction is preferably performed in a solution. Examples of a solvent which can be used include a mixed solvent of acetonitrile and water; a mixed solvent of a thinner such as toluene or xylene and water; a ternary mixed solvent of toluene or xylene, an alcohol such as ethanol, and water; a mixed solvent of 1,3-dimethyl-3,4,5,6-tetrahydro-2(1H)-pyrimidinone (DMPU) and water; a mixed solvent of an ether such as ethylene glycol dimethyl ether and water; and the like.

However, the catalyst, ligand, base, and solvent which can be used are not limited to the above examples.

In the synthesis scheme (A-1), instead of the arylboron compound (a2), an aryl aluminum, an aryl zirconium, an aryl zinc, an aryl tin, or the like may be used. In addition, the reaction is preferably performed under an inert atmosphere of nitrogen, argon, or the like. Further, heating may be performed with electromagnetic waves.

In particular, in the case where $\alpha^1$ and $\alpha^2$ are the same and $Ar^1$ and $Ar^2$ are the same, or the case where the heterocyclic compound represented by the general formula (G1) does not have a substituent represented by the general formula (G1-2), the synthesis scheme (A-1) is preferred because the heterocyclic compound represented by the general formula (G1) can be synthesized with high purity and high yield In other words, this synthesis method is convenient when $\alpha^1$ and $\alpha^2$ are the same and $Ar^1$ and $Ar^2$ are the same, because 2 equivalents of one of the compound (a2) and the compound (a3) can be added to and reacted with the compound (a1). Further, in the case where the heterocyclic compound represented by the general formula (G1) does not have a substituent represented by the general formula (G1-2), the heterocyclic compound can be synthesized easily by adding only the compound (a2) to the compound (a1) to cause a reaction.

In the above manner, the heterocyclic compound of this embodiment can be synthesized.

(Synthesis Method 2 of the Heterocyclic Compound Represented by the General Formula (G1))

Another method of synthesizing the heterocyclic compound represented by the general formula (G1) is described below. Specifically, an example of a method of synthesizing a heterocyclic compound that is represented by the general formula (G1) and has the substituent represented by the general formula (G1-2) is described. As illustrated in a synthesis scheme (B-1), a halogenated dibenzoquinoxaline compound (a4) and the arylboron compound (a2) are coupled, so that the heterocyclic compound represented by the general formula (G1) can be synthesized. The synthesis scheme (B-1) is illustrated below.

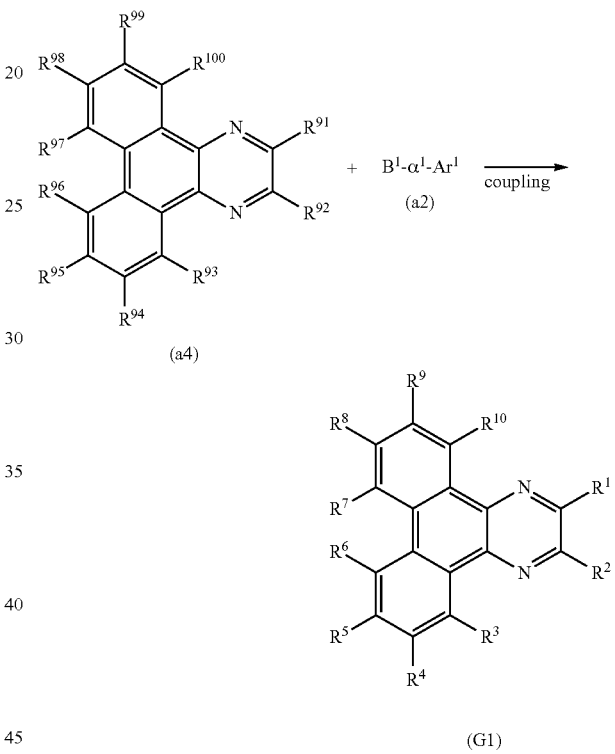

In the synthesis scheme (B-1), $\alpha^1$ represents a substituted or unsubstituted phenylene group or a substituted or unsubstituted biphenyldiyl group, and $Ar^1$ represents a substituted or unsubstituted naphthyl group, a substituted or unsubstituted phenanthryl group, or a substituted or unsubstituted triphenylenyl group. Further, $B^1$ represents a boronic acid or dialkoxyborane.

In the synthesis scheme (B-1), any one of $R^{91}$ to $R^{100}$ represents a substituent represented by the following general formula (a4-1); another one of $R^{91}$ to $R^{100}$ represents a substituent represented by the following general formula (a4-2); and the others separately represent hydrogen, an alkyl group having 1 to 6 carbon atoms, a substituted or unsubstituted phenyl group, or a substituted or unsubstituted biphenyl group.

In the synthesis scheme (B-1), any one of $R^1$ to $R^{10}$ represents a substituent represented by the following general formula (G1-1); another one of $R^1$ to $R^{10}$ represents a substituent represented by the following general formula (G1-2); and the others separately represent hydrogen, an alkyl group having 1 to 6 carbon atoms, a substituted or unsubstituted phenyl group, or a substituted or unsubstituted biphenyl group.

$$-X^1 \quad (a4\text{-}1)$$

$$-\alpha^2\text{-}A^2 \quad (a4\text{-}2)$$

$$-\alpha^1\text{-}A^1 \quad (G1\text{-}1)$$

$$-\alpha^2\text{-}A^2 \quad (G1\text{-}2)$$

Note that in the general formula (a4-1), $X^1$ represents chlorine, bromine, or iodine. $X^1$ preferably represents bromine or iodine, which has high reactivity, more preferably iodine. In the general formula (G1-1), $\alpha^1$ represents a substituted or unsubstituted phenylene group or a substituted or unsubstituted biphenyldiyl group, and $Ar^1$ represents a substituted or unsubstituted naphthyl group, a substituted or unsubstituted phenanthryl group, or a substituted or unsubstituted triphenylenyl group. In the general formulas (a4-2) and (G1-2), $\alpha^2$ represents a substituted or unsubstituted phenylene group or a substituted or unsubstituted biphenyldiyl group, and $Ar^2$ represents a substituted or unsubstituted naphthyl group, a substituted or unsubstituted phenanthryl group, or a substituted or unsubstituted triphenylenyl group.

In the synthesis scheme (B-1), $\alpha^1$ is bonded to a position where $X^1$ has been bonded.

Note that there are a variety of reaction conditions for the coupling reaction in the synthesis scheme (B-1). As an example, a synthesis method using a metal catalyst in the presence of a base can be employed.

In the synthesis scheme (B-1), a Suzuki-Miyaura reaction can be employed. Details are omitted because the above synthesis scheme (A-1) can be referred to.

In the above manner, the heterocyclic compound of this embodiment can be synthesized.

Since the heterocyclic compound of this embodiment has a wide band gap, high emission efficiency can be obtained by using the heterocyclic compound in a light-emitting layer of a light-emitting element as a host material in which a light-emitting material is dispersed. In particular, the heterocyclic compound of this embodiment is suitably used as a host material in which a phosphorescent compound is dispersed. Further, owing to a high electron-transport property, the heterocyclic compound of this embodiment can be suitably used as a material of an electron-transport layer in a light-emitting element. By use of the heterocyclic compound of this embodiment, a light-emitting element that can be driven at a low voltage, a light-emitting element having high emission efficiency, or a light-emitting element having a long lifetime can be achieved. Furthermore, by use of this light-emitting element, a light-emitting device, an electronic device, and a lighting device each having low power consumption can be obtained.

Further, the heterocyclic compound of this embodiment can be used for an organic thin-film solar cell. Specifically, the heterocyclic compound according to one embodiment of the present invention can be used for a carrier-transport layer or a carrier-injection layer owing to its carrier-transport property. Furthermore, the heterocyclic compound according to one embodiment of the present invention can be photoexcited and hence can be used for a power generation layer.

(Embodiment 2)

In this embodiment, as one embodiment of the present invention, a light-emitting element in which any of the heterocyclic compounds described in Embodiment 1 is used is described with reference to FIGS. 1A and 1B. This embodiment shows a light-emitting element in which the heterocyclic compound is used for a light-emitting layer.

In the light-emitting element of this embodiment, an EL layer having at least a light-emitting layer is interposed between a pair of electrodes. The EL layer may also have a plurality of layers in addition to the light-emitting layer. The plurality of layers is a combination of layers containing a substance with a high carrier-injection property and a substance with a high carrier-transport property, which are stacked so that a light-emitting region is formed in a region away from the electrodes, that is, so that the carriers are recombined in an area away from the electrodes. In this specification, the layer containing a substance with a high carrier-injection property or a substance with a high carrier-transport property is also called functional layer which functions, for instance, to inject or transport carriers. As the functional layer, a hole-injection layer, a hole-transport layer, an electron-injection layer, an electron-transport layer, or the like can be used.

In the light-emitting element of this embodiment illustrated in FIG. 1A, an EL layer 102 having a light-emitting layer 113 is provided between a pair of electrodes, a first electrode 101 and a second electrode 103. The EL layer 102 includes a hole-injection layer 111, a hole-transport layer 112, the light-emitting layer 113, an electron-transport layer 114, and an electron-injection layer 115. The light-emitting element in FIG. 1A includes the first electrode 101 formed over a substrate 100; the hole-injection layer 111, the hole-transport layer 112, the light-emitting layer 113, the electron-transport layer 114, and the electron-injection layer 115 which are stacked over the first electrode 101 in this order; and the second electrode 103 provided over the electron-injection layer 115. Note that, in the light-emitting element described in this embodiment, the first electrode 101 functions as an anode and the second electrode 103 functions as a cathode.

The substrate 100 is used as a support of the light-emitting element. For example, glass, quartz, plastic, or the like can be used for the substrate 100. Furthermore, a flexible substrate may be used. The flexible substrate is a substrate that can be bent (is flexible), such as a plastic substrate made of polycarbonate, polyarylate, or poly(ether sulfone). Alternatively, a film (made of polypropylene, a polyester, poly(vinyl fluoride), poly(vinyl chloride), or the like), an inorganic film formed by evaporation, or the like can be used. Note that materials other than the above materials can be used as long as they can function as a support of a light-emitting element.

For the first electrode 101, a metal, an alloy, an electrically conductive compound, a mixture thereof, or the like which has a high work function (specifically, a work function of 4.0 eV or more) is preferably used. Specific examples are indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide (IWZO), and the like. Films of these conductive metal oxides are usually formed by sputtering; however, a sol-gel method or the like may also be used. For example, a film of indium oxide-zinc oxide can be formed by a sputtering method using a target in which 1 wt % to 20 wt % zinc oxide is added to indium oxide. A film of indium oxide containing tungsten oxide and zinc oxide (IWZO) can be formed by a sputtering method using a target in which tungsten oxide and zinc oxide are mixed at 0.5 wt % to 5 wt % and 0.1 wt % to 1 wt %, respectively, with indium oxide. Further, gold, platinum, nickel, tungsten, chromium, molybdenum, iron, cobalt, copper, palladium, nitrides of metal materials (e.g., titanium nitride), and the like can be used.

Note that, in the EL layer 102, when a layer in contact with the first electrode 101 is formed using a composite material of an organic compound and an electron acceptor (acceptor) described later, the first electrode 101 can be formed using any of a variety of metals, alloys, and electrically conductive compounds, a mixture thereof, and the like regardless of the work function. For example, aluminum, silver, an alloy containing aluminum (e.g., Al—Si), or the like can be used.

The EL layer 102 formed over the first electrode 101 includes at least the light-emitting layer 113, and part of the EL layer 102 is formed using the heterocyclic compound which is one embodiment of the present invention. For the part of the EL layer 102, a known substance can be used, and either a low molecular compound or a high molecular compound can be used. Note that the substance used for forming the EL layer 102 may have not only a structure formed of only an organic compound but also a structure in which an inorganic compound is partially contained.

Figure 1B:
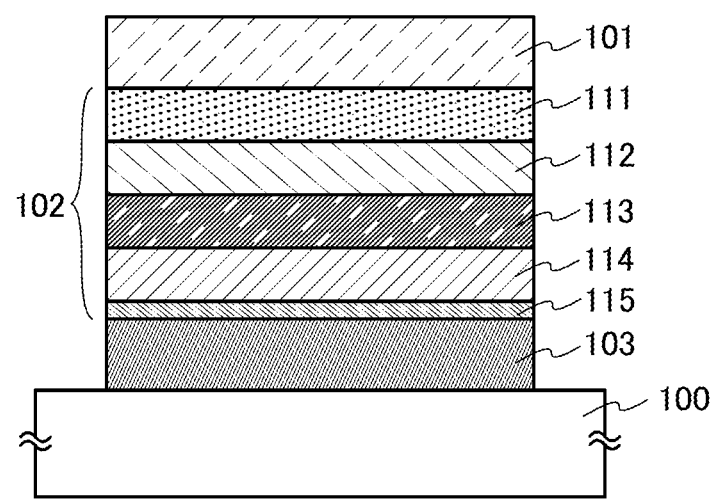

As illustrated in FIGS. 1A and 1B, the EL layer 102 is formed by stacking as appropriate the hole-injection layer 111, the hole-transport layer 112, the electron-transport layer 114, the electron-injection layer 115, and the like in combination, in addition to the light-emitting layer 113.

The hole-injection layer 111 is a layer containing a substance with a high hole-injection property. As the substance with a high hole-injection property, for example, metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide can be used. A phthalocyanine-based compound such as phthalocyanine (abbreviation: $H_2Pc$), or copper(II) phthalocyanine (abbreviation: CuPc) can also be used.

Alternatively, any of the following aromatic amine compounds which are low molecular organic compounds can be used: 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Further alternatively, any of high molecular compounds (e.g., oligomers, dendrimers, or polymers) can be used. For example, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine (abbreviation: poly-TPD) can be used. Further, a high molecular compound to which acid is added, such as poly(3,4-ethylenedioxythiophene)/poly(styrenesulfonic acid) (PEDOT/PSS) or polyaniline/poly(styrenesulfonic acid) (PAni/PSS), can be used.

A composite material in which an organic compound and an electron acceptor (acceptor) are mixed may be used for the hole-injection layer 111. Such a composite material has an excellent hole-injection and hole-transport properties because holes are generated in the organic compound by the electron acceptor.

As the organic compound for the composite material, various compounds such as an aromatic amine compound, a carbazole derivative, aromatic hydrocarbon, and a high molecular compound (such as oligomer, dendrimer, or polymer) can be used. The organic compound used for the composite material is preferably an organic compound with a high hole-transport property. Specifically, a substance having a hole mobility of $10^{-6}$ cm$^2$/V·s or higher is preferably used. However, substances other than the above substances may be used as long as they are substances with a hole-transport property higher than an electron-transport property. The organic compounds which can be used for the composite material are specifically shown below.

Examples of the organic compounds that can be used for the composite material include aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BPAFLP); and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl]-2,3,5,6-tetraphenylbenzene.

Alternatively, it is possible to use an aromatic hydrocarbon compound such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, or 2,3,6,7-tetramethyl-9,10-di(1-naphthyl)anthracene.

Further alternatively, it is possible to use an aromatic hydrocarbon compound such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), or 9,10-bis[4-(2,2-diphenylvinyl)phenyl]anthracene (abbreviation: DPVPA).

As the electron acceptor, organic compounds such as 7,7,8,8-tetracyano-2,3,5,6-tetrafluoroquinodimethane (abbreviation: $F_4$-TCNQ) and chloranil; and transition metal oxides can be used. Alternatively, oxides of metals belonging to Groups 4 to 8 in the periodic table can be used. Specifically, vanadium oxide, niobium oxide, tantalum oxide, chromium oxide, molybdenum oxide, tungsten oxide, manganese oxide, and rhenium oxide are preferable because their electron-accepting property is high. Among these, molybdenum oxide is especially preferable because it is stable in the air, has a low hygroscopic property, and is easily treated.

Note that the hole-injection layer 111 may be formed using a composite material of the above-described high molecular compound, such as PVK, PVTPA, PTPDMA, or Poly-TPD, and the above-described electron acceptor.

The hole-transport layer 112 is a layer that contains a substance with a high hole-transport property. Examples of the substance with a high hole-transport property include a substance having a carbazole skeleton, a substance having a triarylamine skeleton, a substance having a dibenzothiophene skeleton, and a substance having a dibenzofuran skeleton. Specifically, for example, it is possible to use an aromatic amine compound such as NPB, TPD, BPAFLP, 4,4'-bis[N-(9, 9-dimethylfluoren-2-yl)-N-phenylamino]biphenyl (abbreviation: DFLDPBi), or 4,4'-bis[N-(spiro-9,9'-bifluoren-2-yl)-N-phenylamino]biphenyl (abbreviation: BSPB). The substances mentioned here are mainly ones that have a hole mobility of $10^{-6}$ cm$^2$/V·s or higher. However, substances other than the above substances may be used as long as they are substances with a hole-transport property higher than an electron-transport property. The layer containing a substance with a high hole-transport property is not limited to a single layer, and two or more layers containing the above substances may be stacked.

For the hole-transport layer 112, a carbazole derivative such as CBP, CzPA, or PCzPA or an anthracene derivative such as t-BuDNA, DNA, or DPAnth may also be used.

For the hole-transport layer 112, a high molecular compound such as PVK, PVTPA, PTPDMA, or Poly-TPD can also be used.

The light-emitting layer 113 is a layer that contains a light-emitting material. In this embodiment, the light-emitting layer contains the heterocyclic compound described in Embodiment 1.

The heterocyclic compound of one embodiment of the present invention is a light-emitting organic compound, and thus can be used as the light-emitting material.

In the light-emitting layer in which a light-emitting material (guest material) is dispersed in another material (host material), the heterocyclic compound can be used as the host material. The guest material which is a light-emitting material is dispersed in the heterocyclic compound, so that light emission from the guest material can be obtained. In this manner, the heterocyclic compound according to one embodiment of the present invention is effectively used as the host material in the light-emitting layer.

In addition, plural types of substances (host materials) can be used as substances in which the light-emitting material (guest material) is dispersed.

The light-emitting layer may contain a different material in addition to the heterocyclic compound according to one embodiment of the present invention and the guest material.

As the light-emitting material, for example, a fluorescent compound which emits fluorescence or a phosphorescent compound which emits phosphorescence can be used. Examples of the fluorescent compound that can be used for the light-emitting layer 113 include the following. Examples of a material that emits blue light include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA), and the like. Examples of a material that emits green light include N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. Examples of a material that emits yellow light include rubrene, 5,12-bis(1,1'-biphenyl-4-yl)-6,11-diphenyltetracene (abbreviation: BPT), and the like. Examples of a material that emits red light include N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), and the like.

Examples of the phosphorescent compound that can be used for the light-emitting layer 113 include the following. Examples of a material that emits green light include tris(2-phenylpyridinato-N,C$^{2'}$)iridium(III) (abbreviation: [Ir(ppy)$_3$]), bis(2-phenylpyridinato-N,C$^{2'}$)iridium(III)acetylacetonate (abbreviation: [Ir(ppy)$_2$(acac)]), bis(1,2-diphenyl-1H-benzimidazolato)iridium(III)acetylacetonate (abbreviation: [Ir(pbi)$_2$(acac)]), bis(benzo[h]quinolinato)iridium(III)acetylacetonate (abbreviation: [Ir(bzq)$_2$(acac)]), tris(benzo[h]quinolinato)iridium(III) (abbreviation: [Ir(bzq)$_3$]), and the like. Examples of a material that emits yellow light include bis(2,4-diphenyl-1,3-oxazolato-N,C$^{2'}$)iridium(III)acetylacetonate (abbreviation: [Ir(dpo)$_2$(acac)]), bis[2-(4'-(perfluorophenylphenyl)pyridinato]iridium(III)acetylacetonate (abbreviation: [Ir(p-PF-ph)$_2$(acac)]), bis(2-phenylbenzothiazolato-N,C$^{2'}$)iridium(III)acetylacetonate (abbreviation: [Ir(bt)$_2$(acac)]), (acetylacetonato)bis[2,3-bis(4-fluorophenyl)-5-methylpyrazinato] iridium(III) (abbreviation: [Ir(Fdppr-Me)$_2$(acac)]), (acetylacetonato)bis[2-(4-methoxyphenyl)-3,5-dimethylpyrazinato] iridium(III) (abbreviation: [Ir(dmmoppr)$_2$(acac)]), and the like. Examples of a material that emits orange light include tris(2-phenylquinolinato-N,C$^{2'}$)iridium(III) (abbreviation: [Ir(pq)$_3$]), bis(2-phenylquinolinato-N,C$^{2'}$)iridium(III)acetylacetonate (abbreviation: [Ir(pq)$_2$(acac)]), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), and the like. Examples of a material that emits red light include organometallic complexes such as bis[2-(2'-benzo[4,5-a]thienyl)pyridinato-N,C$^{3'}$)iridium(III) acetylacetonate (abbreviation: [Ir(btp)$_2$(acac)]), bis(1-phenylisoquinolinato-N,C$^{2'}$)iridium(III)acetylacetonate (abbreviation: [Ir(piq)$_2$(acac)]), (acetylacetonato)bis[2,3-bis(4-fluorophenyl)quinoxalinato]iridium(III) (abbreviation: [Ir(Fdpq)$_2$(acac)]), (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and 2,3,7,8,12,13,17,18-octaethyl-21H,23H-porphyrin platinum(II) (abbreviation: PtOEP). In addition, a rare earth metal complex such as tris(acetylacetonato)(monophenanthroline)terbium(III) (abbreviation: [Tb(acac)$_3$(Phen)]), tris(1,3-diphenyl-1,3-propanedionato)(monophenanthroline)europium(III) (abbreviation: [Eu(DBM)$_3$(Phen)]), or tris[1-(2-thenoyl)-3,3,3-trifluoroacetonato](monophenanthroline)europium(III) (abbreviation: [Eu(TTA)$_3$(Phen)]) exhibits light emission from a rare earth metal ion (electron transition between different multiplicities); therefore, such a rare earth metal complex can be used as a phosphorescent compound.

Note that the dibenzo[f,h]quinoxaline skeleton is considered to predominantly determine the LUMO level of the heterocyclic compound according to one embodiment of the present invention. Further, the compound has a deep LUMO level of at least −2.8 eV or less, specifically −2.9 eV or less, on the basis of cyclic voltammetry (CV) measurements. For example, according to Example 3, the LUMO level of DBqPPn (abbreviation) based on CV measurements is −2.95 eV. Further, the LUMO level of the above-described phosphorescent compound having a pyrazine skeleton, such as [Ir(mppr-Me)$_2$(acac)], [Ir(mppr-iPr)$_2$(acac)], [Ir(tppr)$_2$(acac)], or [Ir(tppr)$_2$(dpm)], is substantially equally deep. Accordingly, in a light-emitting layer where the heterocyclic compound according to one embodiment of the present invention is used as the host material and the phosphorescent compound having a pyrazine skeleton is used as the guest material, electron traps in the light-emitting layer can be reduced as much as possible, so that the light-emitting element can be driven at an extremely low voltage.

Note that the host material preferably has a deeper HOMO level and a shallower LUMO level than the guest material (light-emitting material). Such a structure allows carriers injected to the host material to be efficiently injected to the guest material. The heterocyclic compound according to one embodiment of the present invention has a relatively deep HOMO level (the value thereof is relatively small), and thus is preferable as the host material. Hence, the HOMO level of the guest material is preferably higher than or equal to −6.0 eV and lower than or equal to −5.0 eV, and the LUMO level of the guest material is preferably higher than or equal to −3.5 eV and lower than or equal to −2.5 eV.

As the light-emitting material, a high molecular compound can also be used. Specifically, as a material that emits blue light, poly(9,9-dioctylfluorene-2,7-diyl) (abbreviation: PFO), poly[(9,9-dioctylfluorene-2,7-diyl)-co-(2,5-dimethoxybenzene-1,4-diyl)](abbreviation: PF-DMOP), poly{(9,9-dioctylfluorene-2,7-diyl)-co-[N,N'-di-(p-butylphenyl)-1,4-diaminobenzene]}(abbreviation: TAB-PFH), or the like can be used. As a material that emits green light, poly(p-phenylenevinylene) (abbreviation: PPV), poly[(9,9-dihexylfluorene-2,7-diyl)-alt-co-(benzo[2,1,3]thiadiazole-4,7-diyl)](abbreviation: PFBT), poly[(9,9-dioctyl-2,7-divinylenefluorenylene)-alt-co-(2-methoxy-5-(2-ethylhexyloxy)-1,4-phenylene)], or the like can be used. As a material that emits orange to red light, poly[2-methoxy-5-(2'-ethylhexoxy)-1,4-phenylenevinylene](abbreviation: MEH-PPV), poly(3-butylthiophene-2,5-diyl) (abbreviation: R4-PAT), poly{[9,9-d]hexyl-2,7-bis(1-cyanovinylene)fluorenylene]-alt-co-[2,5-bis(N,N'-diphenyl amino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]}(abbreviation: CN-PPV-DPD), or the like can be used.

The following shows another embodiment of the light-emitting layer 113 described in this embodiment. The light-emitting layer 113 can contain a phosphorescent compound, a first organic compound, and a second organic compound. The phosphorescent compound is the guest material (light-emitting material) in the light-emitting layer 113. One of the first organic compound and the second organic compound, the content of which is higher than that of the other in the light-emitting layer 113, is the host material in the light-emitting layer 113. The heterocyclic compound according to one embodiment of the present invention can be used as the first organic compound or the second organic compound.

By dispersing the guest material in the host material in the light-emitting layer 113, crystallization of the light-emitting layer can be suppressed. Further, it is possible to suppress concentration quenching due to high concentration of the guest material, and thus the light-emitting element can have higher emission efficiency.

It is preferable that the T1 level of each of the first and second organic compounds be higher than that of the phosphorescent compound. This is because, when the T1 level of the first organic compound (or the second organic compound) is lower than that of the phosphorescent compound, the triplet excitation energy of the phosphorescent compound, which is to contribute to light emission, is quenched by the first organic compound (or the second organic compound) and accordingly the emission efficiency is decreased.

As the phosphorescent compound, a phosphorescent organometallic iridium complex or the like can be used. As the first and second organic compounds, a compound which easily accepts electrons (electron-transport compound) and a compound which easily accepts holes (hole-transport compound) are preferably combined.

The heterocyclic compound according to one embodiment of the present invention can be used as an electron-transport compound.

As a hole-transport compound, a compound with a higher hole-transport property than the heterocyclic compound according to one embodiment of the present invention, which is used as the electron-transport compound, is used. For example, it is possible to use any of the compounds given above as compounds that can be used for the hole-transport layer 112, such as a substance having a carbazole skeleton, a substance having a triarylamine skeleton, a substance having a dibenzothiophene skeleton, and a substance having a dibenzofuran skeleton. Note that a compound having a higher T1 level than a phosphorescent compound to be used is selected from these compounds. Further, the difference between the HOMO level of the hole-transport compound and the HOMO level of the phosphorescent compound is preferably within 0.2 eV in which case the phosphorescent compound does not strongly trap holes so that the light-emitting region expands. Specifically, for example, it is possible to use any of the following: 4-phenyl-4'-(9-phenyl-9H-carbazol-3-yl)triphenylamine (abbreviation: PCBA1BP), PCzPCN1, 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-N',N'-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), TPD, DPAB, N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), PCzPCA1, 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), DNTPD, 3,6-bis[N-(4-diphenylaminophenyl)-N-(1-naphthyl)amino]-9-phenylcarbazole (abbreviation: PCzTPN2), and PCzPCA2.

Note that in the case where a compound which easily accepts electrons and a compound which easily accepts holes are used as the first organic compound and the second organic compound, carrier balance can be controlled by the mixture ratio of the compounds. Specifically, the ratio of the first organic compound to the second organic compound is preferably 1:9 to 9:1.

The electron-transport layer 114 is a layer containing a substance with a high electron-transport property. For example, as the substance with a high electron-transport property, a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq), can be used. Alternatively, a metal complex or the like including an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances mentioned here are mainly ones that have an electron mobility of $10^{-6}$ cm$^2$/V·s or higher. Furthermore, the electron-transport layer is not limited to a single layer, and two or more layers made of the above substances may be stacked.

The electron-injection layer 115 is a layer containing a substance with a high electron-injection property. For the electron-injection layer 115, an alkali metal, an alkaline earth metal, or a compound thereof, such as lithium, cesium, calcium, lithium fluoride, cesium fluoride, calcium fluoride, or lithium oxide, can be used. Alternatively, a rare earth metal compound such as erbium fluoride can be used. Further alternatively, the above substances for forming the electron-transport layer 114 can be used.

Further alternatively, a composite material in which an organic compound and an electron donor (donor) are mixed may be used for the electron-injection layer 115. Such a composite material has an excellent electron-injection and electron-transport properties because electrons are generated in the organic compound by the electron donor. In this case, the organic compound is preferably a material excellent in transporting the generated electrons. Specifically, the above substances for forming the electron-transport layer 114 (e.g., a metal complex or a heteroaromatic compound) can be used, for example. As the electron donor, a substance exhibiting an electron-donating property to the organic compound may be used. Specifically, it is preferable to use an alkali metal, an alkaline earth metal, or a rare earth metal, such as lithium, cesium, magnesium, calcium, erbium, or ytterbium. Further, an alkali metal oxide or an alkaline earth metal oxide is preferable, such as lithium oxide, calcium oxide, or barium oxide. Alternatively, Lewis base such as magnesium oxide can be used. Further alternatively, an organic compound such as tetrathiafulvalene (abbreviation: TTF) can be used.

Note that each of the above-described hole-injection layer 111, hole-transport layer 112, light-emitting layer 113, electron-transport layer 114, and electron-injection layer 115 can be formed by a method such as an evaporation method (e.g., a vacuum evaporation method), an inkjet method, or a coating method.

When the second electrode 103 functions as a cathode, it is preferably formed using a metal, an alloy, an electrically conductive compound, a mixture thereof, or the like having a low work function (preferably, a work function of 3.8 eV or less). Specifically, any of the following can be used: aluminum or silver; an element belonging to Group 1 or 2 of the periodic table, that is, an alkali metal such as lithium or cesium or an alkaline earth metal such as calcium or strontium; magnesium (Mg); an alloy thereof (e.g., Mg—Ag or Al—Li); a rare earth metal such as europium or ytterbium; an alloy thereof; and the like.

However, when a layer which is in contact with the second electrode 103 and included in the EL layer 102 is formed using a composite material containing an organic compound and an electron donor (donor) described above, a variety of conductive materials such as aluminum, silver, ITO, and indium oxide-tin oxide containing silicon or silicon oxide can be used regardless of work function.

Note that the second electrode 103 can be formed by a vacuum evaporation method or a sputtering method. Alternatively, in the case of using a silver paste or the like, a coating method, an inkjet method, or the like can be used.

In the above-described light-emitting element, current flows due to a potential difference generated between the first electrode 101 and the second electrode 103, and holes and electrons recombine in the EL layer 102, whereby light is emitted. Then, this emitted light is extracted out through one or both of the first electrode 101 and the second electrode 103. Therefore, one or both of the first electrode 101 and the second electrode 103 is/are an electrode with a property of transmitting visible light.

Further, the structure of a layer provided between the first electrode 101 and the second electrode 103 is not limited to the above-described structure. A structure other than the above may alternatively be employed as long as a light-emitting region in which holes and electrons recombine is provided in a portion away from the first electrode 101 and the second electrode 103 in order to prevent quenching due to proximity of the light-emitting region to a metal.

In other words, the stacked structure of the layers may be freely formed by, without particular limitation, combining a layer containing a substance with a high electron-transport property, a substance with a high hole-transport property, a substance with a high electron-injection property, a substance with a high hole-injection property, a bipolar substance (substance with a high electron-transport property and a high hole-transport property), a hole-blocking material, or the like and a light-emitting layer containing the heterocyclic compound according to one embodiment of the present invention as a host material.

The heterocyclic compound according to one embodiment of the present invention is a substance with a high electron-transport property, and thus can be used for the electron-transport layer.

By use of the heterocyclic compound according to one embodiment of the present invention for both the light-emitting layer (particularly as the host material in the light-emitting layer) and the electron-transport layer, materials having close LUMO levels are in contact with each other, so that electrons can be easily injected to the light-emitting layer from the electron-transport layer. Accordingly, the light-emitting element can be driven at an extremely low voltage.

In a light-emitting element illustrated in FIG. 1B, the EL layer 102 is provided between the pair of electrodes, the first electrode 101 and the second electrode 103, over the substrate 100. The EL layer 102 includes the hole-injection layer 111, the hole-transport layer 112, the light-emitting layer 113, the electron-transport layer 114, and the electron-injection layer 115. The light-emitting element in FIG. 1B includes the second electrode 103 functioning as a cathode over the substrate 100; the electron-injection layer 115, the electron-transport layer 114, the light-emitting layer 113, the hole-transport layer 112, and the hole-injection layer 111 which are stacked over the second electrode 103 in this order; and the first electrode 101 functioning as an anode over the hole-injection layer 111.

The following shows a specific formation method of the light emitting element.

The light-emitting element of Embodiment 2 has a structure in which the EL layer is interposed between the pair of electrodes. The EL layer has at least the light-emitting layer, and the light-emitting layer is formed using the heterocyclic compound according to one embodiment of the present invention as a host material. Further, the EL layer may include a functional layer (e.g., a hole-injection layer, a hole-transport layer, an electron-transport layer, or an electron-injection layer) in addition to the light-emitting layer. Each electrode (the first electrode or the second electrode), the light-emitting layer, and each functional layer may be formed by any of the wet processes such as a droplet discharging method (inkjet method), a spin coating method, or a printing method, or by a dry process such as a vacuum evaporation method, a CVD method, or a sputtering method. The use of a wet process enables the formation at atmospheric pressure using a simple device and process, thereby having the effects of simplifying the process and improving the productivity. In contrast, in a dry process, dissolution of a material is not needed, and thus, a material that has low solubility in a solution can be used to expand the range of material choices.

All the thin films included in the light-emitting element may be formed by a wet method. In this case, the light-emitting element can be manufactured with only facilities needed for a wet process. Alternatively, formation of the stacked layers up to formation of the light-emitting layer may be performed by a wet process whereas the functional layer, the first electrode, and the like which are stacked over the light-emitting layer may be formed by a dry process. Further alternatively, the second electrode and the functional layer may be formed by a dry process before the formation of the light-emitting layer whereas the light-emitting layer, the functional layer stacked thereover, and the first electrode may be formed by a wet process. Needless to say, this embodiment is not limited to this, and the light-emitting element can be formed by appropriate selection from a wet method and a dry method depending on a material to be used, necessary film thickness, and the interface state.

In this embodiment, the light-emitting element is formed over a substrate made of glass, plastic, or the like. A plurality of such light-emitting elements is formed over one substrate, thereby forming a passive matrix light-emitting device. In addition, for example, a thin film transistor (TFT) may be formed over a substrate formed of glass, plastic, or the like, and a light-emitting element may be manufactured over an electrode electrically connected to the TFT. In this manner, an active matrix light-emitting device in which the TFT controls the drive of the light-emitting element can be manufactured. Note that there is no particular limitation on the structure of the TFT. Either a staggered TFT or an inverted staggered TFT may be employed. In addition, there is no particular limitation on crystallinity of a semiconductor used for the TFT; an amorphous semiconductor or a crystalline semiconductor may be used. In addition, a driver circuit formed over a TFT substrate may be constructed from both n-channel and p-channel TFTs or from one of n-channel and p-channel TFTs.

Thus, a light-emitting element can be manufactured using the heterocyclic compound according to one embodiment of the present invention. By use of the heterocyclic compound according to one embodiment of the present invention for a light-emitting element, a light-emitting element that is driven at a low voltage can be obtained. Alternatively, a light-emitting element with high emission efficiency can be obtained. Further alternatively, a light-emitting element with a long lifetime can be obtained.

Furthermore, a light-emitting device (such as an image display device) using this light-emitting element according to one embodiment of the present invention, which is obtained as above, can have low power consumption.

Note that by use of the light-emitting element described in this embodiment, a passive matrix light-emitting device or an active matrix light-emitting device in which the drive of the light-emitting element is controlled by a thin film transistor (TFT) can be manufactured.

This embodiment can be implemented in appropriate combination with the other embodiments.

(Embodiment 3)

In Embodiment 3, a mode of a light-emitting element having a structure in which a plurality of light-emitting units is stacked (hereinafter, referred to as stacked-type element) is described with reference to FIGS. 2A and 2B. This light-emitting element includes the plurality of light-emitting units between a first electrode and a second electrode.

Figure 2A:
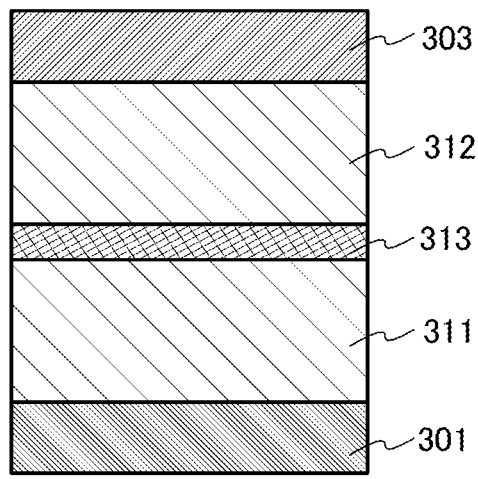
FIGS. 2A and 2B illustrate light-emitting elements according to embodiments of the present invention.

In FIG. 2A, a first light-emitting unit 311 and a second light-emitting unit 312 are stacked between a first electrode 301 and a second electrode 303. In this embodiment, the first electrode 301 functions as an anode and the second electrode 303 functions as a cathode. The first electrode 301 and the second electrode 303 can be the same as those in Embodiment 2. Further, the first light-emitting unit 311 and the second light-emitting unit 312 may have the same or different structures. The first light-emitting unit 311 and the second light-emitting unit 312 may be the same as those in Embodiment 2, or either of the units may be the same as that in Embodiment 2.

Further, a charge generation layer 313 is provided between the first light-emitting unit 311 and the second light-emitting unit 312. The charge generation layer 313 functions so that electrons are injected into one light-emitting unit and holes are injected into the other light-emitting unit by application of voltage between the first electrode 301 and the second electrode 303. In this embodiment, when voltage is applied to the first electrode 301 so that the potential thereof is higher than that of the second electrode 303, the charge generation layer 313 injects electrons into the first light-emitting unit 311 and injects holes into the second light-emitting unit 312.

Note that the charge generation layer 313 preferably has the property of transmitting visible light in terms of light extraction efficiency. Further, the charge generation layer 313 functions even when it has lower conductivity than the first electrode 301 or the second electrode 303.

The charge generation layer 313 may have either a structure containing an organic compound with a high hole-transport property and an electron acceptor (acceptor) or a structure containing an organic compound with a high electron-transport property and an electron donor (donor). Alternatively, these structures may be stacked.

In the case of the structure in which an electron acceptor is added to an organic compound with a high hole-transport property, any of the following substances can be used as the organic compound with a high hole-transport property, for example: the heterocyclic compounds of embodiments of the present invention; aromatic amine compounds such as NPB, TPD, TDATA, MTDATA, and 4,4'-bis[N-(spiro-9,9'-bifluoren-2-yl)-N-phenylamino]biphenyl (abbreviation: BSPB); and the like. The substances mentioned here are mainly ones that have a hole mobility of $10^{-6}$ cm$^2$/V·s or higher. However, substances other than the above substances may be used as long as they are organic compounds with a hole-transport property higher than an electron-transport property.

Further, as the electron acceptor, 7,7,8,8-tetracyano-2,3,5, 6-tetrafluoroquinodimethane (abbreviation: $F_4$-TCNQ), chloranil, and the like can be given. In addition, a transition metal oxide can be given. In addition, an oxide of metals that belong to Groups 4 to 8 of the periodic table can be given. Specifically, vanadium oxide, niobium oxide, tantalum oxide, chromium oxide, molybdenum oxide, tungsten oxide, manganese oxide, and rhenium oxide are preferable because their electron-accepting property is high. Among these, molybdenum oxide is especially preferable because it is stable in the air, has a low hygroscopic property, and is easily treated.

In contrast, in the case of the structure in which an electron donor is added to an organic compound with a high electron-transport property, as the organic compound with a high electron-transport property, a metal complex having a quinoline skeleton or a benzoquinoline skeleton, such as Alq, Almq$_3$, BeBq$_2$, or BAlq, or the like can be used, for example. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, BPhen, BCP, or the like can be used. The substances mentioned here are mainly ones that have an electron mobility of $10^{-6}$ cm$^2$/V·s or higher. Note that substances other than the above substances may be used as long as they are organic compounds with an electron-transport property higher than a hole-transport property.

Further, as the electron donor, an alkali metal, an alkaline earth metal, a rare earth metal, a metal belonging to Group 13 of the periodic table, or an oxide or carbonate thereof can be used. Specifically, lithium, cesium, magnesium, calcium, ytterbium, indium, lithium oxide, cesium carbonate, or the like is preferably used. Alternatively, an organic compound such as tetrathianaphthacene may be used as the electron donor.

Note that by formation of the charge generation layer 313 with the use of any of the above materials, it is possible to suppress the increase in drive voltage caused when the light-emitting units are stacked.

Figure 2B:
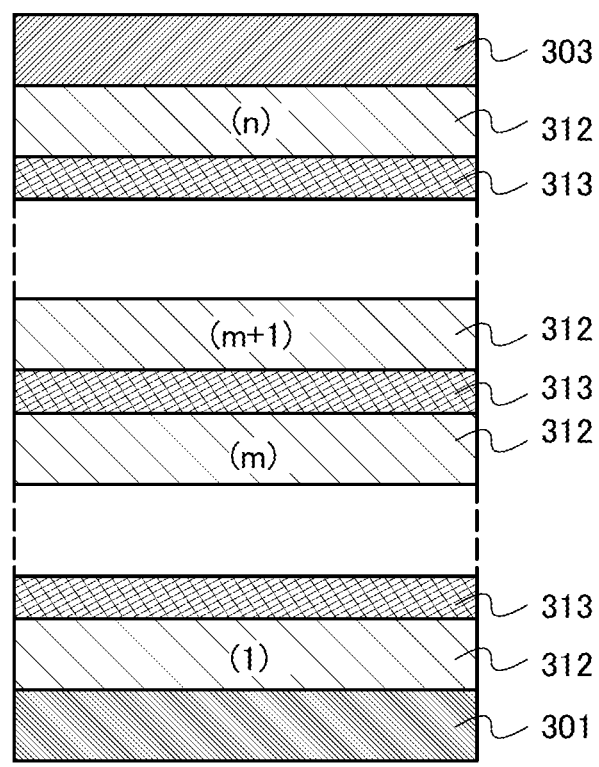

In this embodiment, the light-emitting element having two light-emitting units is described, and one embodiment of the present invention can be similarly applied to a light-emitting element having a stack of three or more light-emitting units as illustrated in FIG. 2B. A plurality of light-emitting units which is partitioned by a charge generation layer is arranged between a pair of electrodes, as in the light-emitting element according to this embodiment, whereby it is possible to achieve an element which has a long lifetime and can emit light with a high luminance while current density is kept low.

The light-emitting units emit light having different colors from each other, thereby obtaining light emission of a desired color in the whole light-emitting element. For example, in a light-emitting element having two light-emitting units, the emission colors of the first light-emitting unit and the second light-emitting unit are made complementary, so that the light-emitting element which emits white light as the whole element can be obtained. Note that the word "complementary" means color relationship in which an achromatic color is obtained when colors are mixed. That is, when complementary colored light emitted from substances is mixed, white light emission can be obtained. Further, the same can be applied to a light-emitting element having three light-emitting units. For example, when a first light-emitting unit emits red light, a second light-emitting unit emits green light, and a third light-emitting unit emits blue light, white light can be emitted from the whole light-emitting element.

This embodiment can be implemented in appropriate combination with the other embodiments.

(Embodiment 4)

Figure 3A:
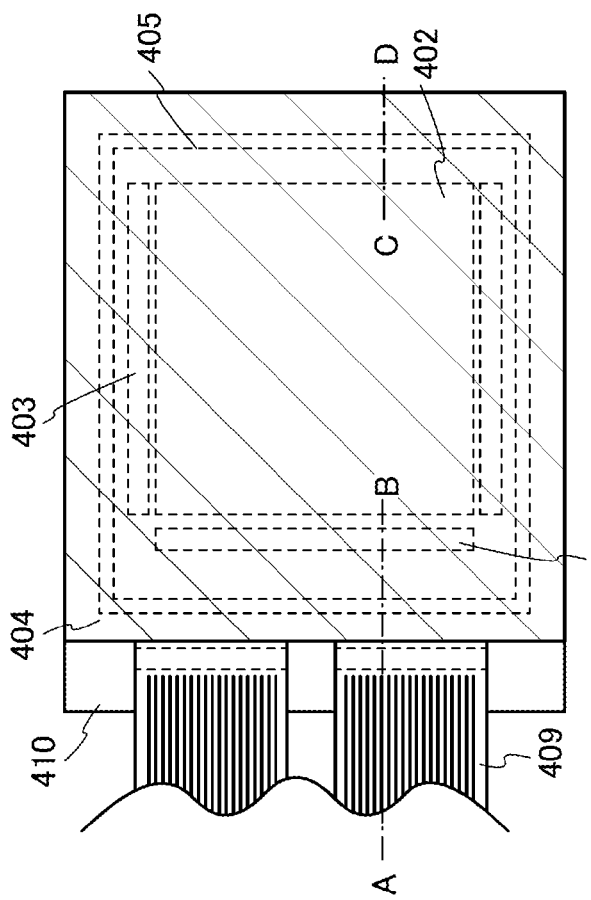
FIGS. 3A and 3B illustrate a light-emitting device according to one embodiment of the present invention.
Figure 3B:
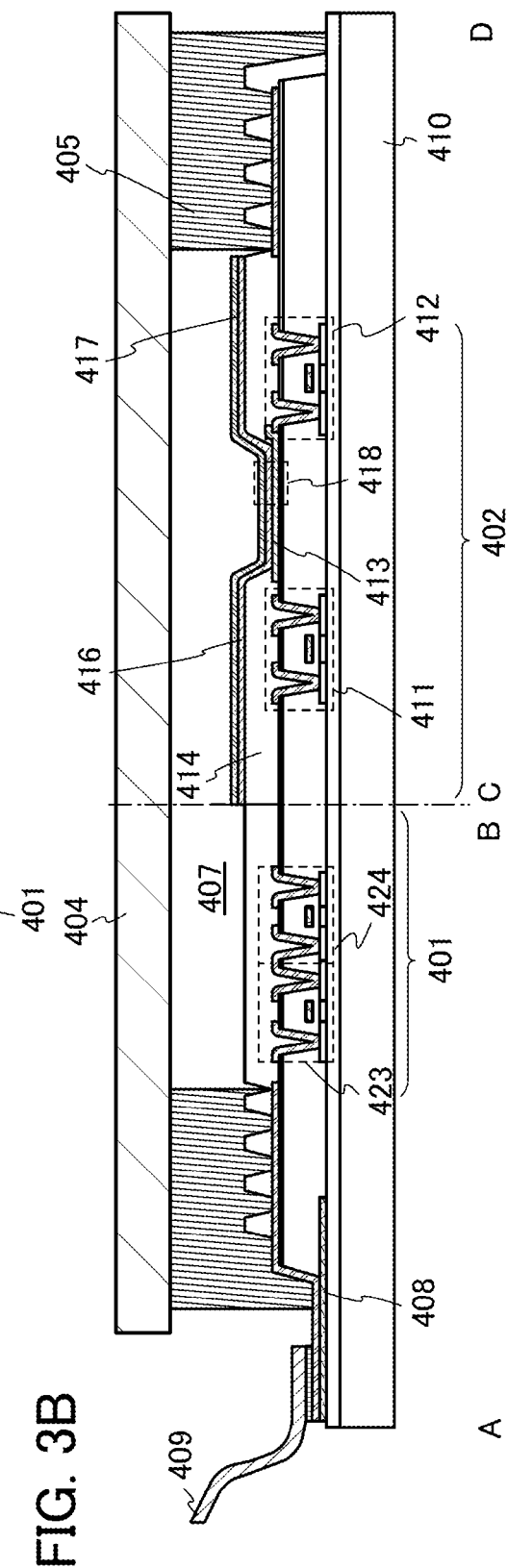

In Embodiment 4, a light-emitting device including a light-emitting element of one embodiment of the present invention is described with reference to FIGS. 3A and 3B. FIG. 3A is a top view illustrating the light-emitting device while FIG. 3B is a cross-sectional view taken along lines A-B and C-D of FIG. 3A.

The light-emitting device of this embodiment includes a source side driver circuit 401 and a gate side driver circuit 403 which are driver circuit portions, a pixel portion 402, a sealing substrate 404, a sealant 405, a flexible printed circuit (FPC) 409, and an element substrate 410. A portion enclosed by the sealant 405 is a space 407.

Note that a lead wiring 408 is a wiring for transmitting signals that are to be input to the source side driver circuit 401 and the gate side driver circuit 403, and receives a video signal, a clock signal, a start signal, a reset signal, and the like from the flexible printed circuit (FPC) 409 which serves as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

The driver circuit portion and the pixel portion are formed over the element substrate 410 illustrated in FIG. 3A. In FIG. 3B, the source side driver circuit 401 which is the driver circuit portion and one pixel in the pixel portion 402 are illustrated.

Note that as the source side driver circuit 401, a CMOS circuit which is obtained by combining an n-channel TFT 423 and a p-channel TFT 424 is formed. The driver circuit may be any of a variety of circuits formed with TFTs, such as a CMOS circuit, a PMOS circuit, or an NMOS circuit. Although this embodiment illustrates a driver-integrated type where the driver circuit is formed over the substrate, the present invention is not limited to this, and the driver circuit may be formed outside the substrate, not over the substrate.

The pixel portion 402 includes a plurality of pixels having a switching TFT 411, a current control TFT 412, and a first electrode 413 electrically connected to a drain of the current control TFT 412. An insulator 414 is formed to cover an end portion of the first electrode 413. Here, the insulator 414 is formed using a positive type photosensitive acrylic resin film.

In order to improve the coverage, the insulator 414 is provided such that either an upper end portion or a lower end portion of the insulator 414 has a curved surface with a curvature. For example, when positive type photosensitive acrylic resin is used as a material for the insulator 414, the insulator 414 preferably has a curved surface with a curvature radius (0.2 μm to 3 μm) only at the upper end. The insulator 414 can be formed using either a negative photosensitive resin or a positive photosensitive resin.

A light-emitting layer 416 and a second electrode 417 are formed over the first electrode 413. Here, as a material for forming the first electrode 413 functioning as the anode, it is preferable to use a material having a high work function. For example, it is possible to use a single layer of an ITO film, an indium tin oxide film containing silicon, an indium oxide film containing 2 wt % to 20 wt % of zinc oxide, a titanium nitride film, a chromium film, a tungsten film, a Zn film, a Pt film, or the like, a stacked layer of a titanium nitride film and a film that mainly contains aluminum, a three-layer structure of a titanium nitride film, a film that mainly contains aluminum, and a titanium nitride film, or the like. Note that, when a stacked structure is employed, resistance of a wiring is low and a favorable ohmic contact is obtained.

In addition, the light-emitting layer 416 is formed by any of various methods such as an evaporation method using an evaporation mask, a droplet discharging method like an inkjet method, a printing method, and a spin coating method. The light-emitting layer 416 includes the heterocyclic compound described in Embodiment 1. Further, the light-emitting layer 416 may contain another material such as a low molecular material, an oligomer, a dendrimer, or a high molecular material.

As a material used for the second electrode 417 which is formed over the light-emitting layer 416 and functions as a cathode, it is preferable to use a material having a low work function (e.g., Al, Mg, Li, Ca, or an alloy or compound thereof such as Mg—Ag, Mg—In, or Al—Li). In order that light generated in the light-emitting layer 416 be transmitted through the second electrode 417, a stack of a thin metal film having a reduced thickness and a transparent conductive film (e.g., ITO, indium oxide containing 2 wt % to 20 wt % of zinc oxide, indium oxide-tin oxide containing silicon or silicon oxide, or zinc oxide) is preferably used for the second electrode 417.

The sealing substrate 404 is attached to the element substrate 410 with the sealant 405; thus, a light-emitting element 418 is provided in the space 407 enclosed by the element substrate 410, the sealing substrate 404, and the sealant 405. Note that the space 407 is filled with a filler such as an inert gas (e.g., nitrogen or argon) or the sealant 405.

Note that as the sealant 405, an epoxy-based resin is preferably used. A material used for these is desirably a material which does not transmit moisture or oxygen as much as possible. As a material for the sealing substrate 404, a glass substrate, a quartz substrate, or a plastic substrate including fiberglass-reinforced plastics (FRP), poly(vinyl fluoride) (PVF), a polyester, an acrylic resin, or the like can be used.

As described above, the active matrix light-emitting device having the light-emitting element of one embodiment of the present invention can be obtained.

Figure 4A:
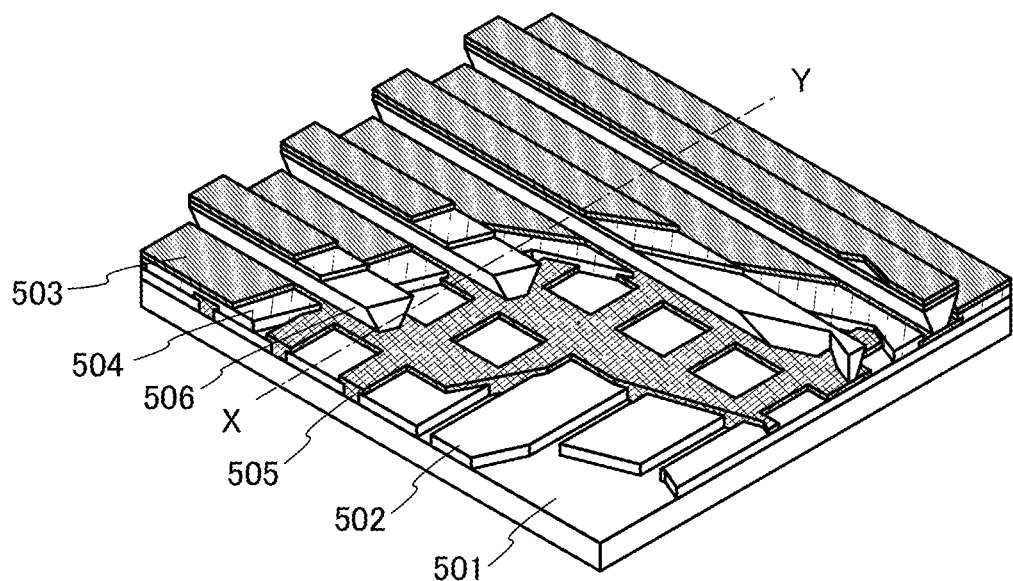
FIGS. 4A and 4B illustrate a light-emitting device according to one embodiment of the present invention.
Figure 4B:
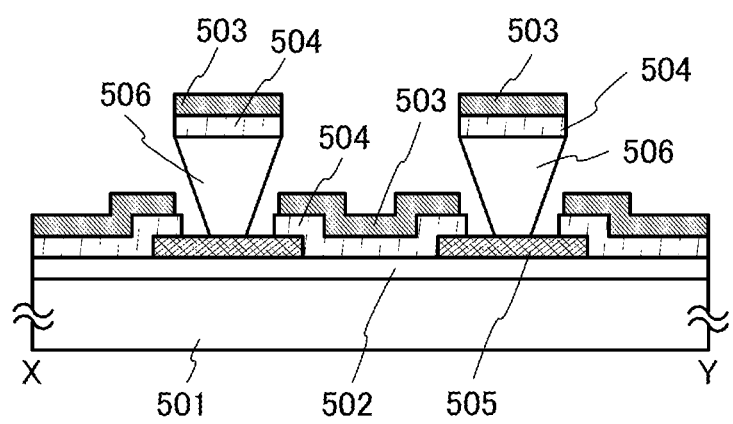

Further, the light-emitting element of one embodiment of the present invention can be used for a passive matrix light-emitting device instead of the above active matrix light-emitting device. FIGS. 4A and 4B illustrate a perspective view and a cross-sectional view of a passive matrix light-emitting device using the light-emitting element of one embodiment of the present invention. FIG. 4A is the perspective view of the light-emitting device, and FIG. 4B is the cross-sectional view taken along line X-Y in FIG. 4A.

In FIGS. 4A and 4B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that the distance between one sidewall and the other sidewall gradually decreases toward the surface of the substrate. In other words, a cross section taken along the direction of the short side of the partition layer 506 is trapezoidal, and the lower side (a side in contact with the insulating layer 505 which is one of a pair of parallel sides of the trapezoidal cross section) is shorter than the upper side (a side not in contact with the insulating layer 505 which is the other of the pair of parallel sides). By providing the partition layer 506 in such a manner, a defect of the light-emitting element due to crosstalk or the like can be prevented.

Thus, the passive matrix light-emitting device having the light-emitting element of one embodiment of the present invention can be obtained.

The light-emitting devices described in this embodiment (the active matrix light-emitting device and the passive matrix light-emitting device) are both formed using the light-emitting element of one embodiment of the present invention, thereby having low power consumption.

This embodiment can be implemented in appropriate combination with the other embodiments.

(Embodiment 5)

In this embodiment, electronic devices and lighting devices including the light-emitting device described in Embodiment 4, which is one embodiment of the present invention, are described with reference to FIGS. 5A to 5D, FIG. 6, FIG. 7, FIG. 8, and FIGS. 9A to 9C.

Examples of the electronic devices include cameras such as video cameras and digital cameras, goggle type displays, navigation systems, audio reproducing devices (e.g., car audio systems and audio systems), computers, game machines, portable information terminals (e.g., mobile computers, cellular phones, portable game machines, and electronic book readers), image reproducing devices in which a recording medium is provided (specifically, devices that are capable of reproducing recording media such as digital versatile discs (DVDs) and provided with a display device that can display an image), and the like.

Figure 5A:
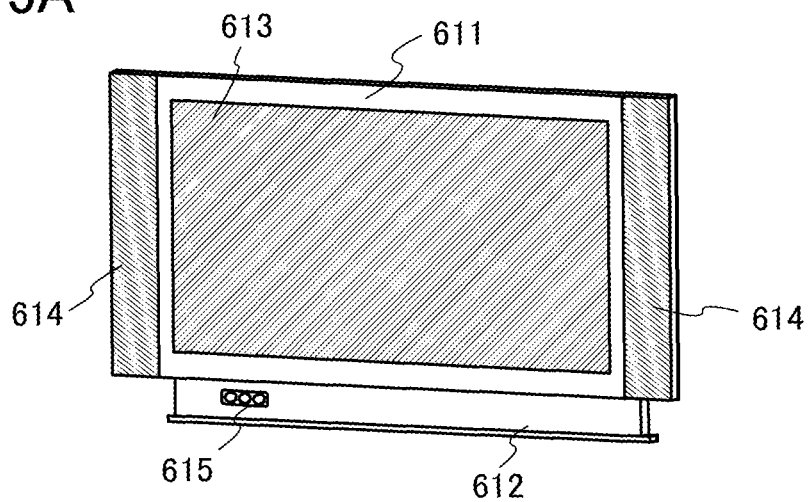
FIGS. 5A to 5D each illustrate an electronic device according to one embodiment of the present invention.

FIG. 5A illustrates a television set according to one embodiment of the present invention, which includes a housing 611, a supporting base 612, a display portion 613, speaker portions 614, video input terminals 615, and the like. In this television set, the light-emitting device of one embodiment of the present invention can be applied to the display portion 613. Since the light-emitting device of one embodiment of the present invention has a low driving voltage, high emission efficiency, and a long lifetime, by the application of the light-emitting device of one embodiment of the present invention, a television set having high reliability and low power consumption can be obtained.

Figure 5B:
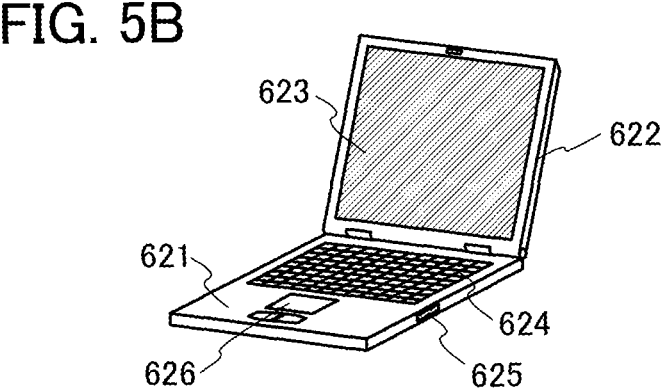

FIG. 5B illustrates a computer according to one embodiment of the present invention, which includes a main body 621, a housing 622, a display portion 623, a keyboard 624, an external connection port 625, a pointing device 626, and the like. In this computer, the light-emitting device of one embodiment of the present invention can be applied to the display portion 623. Since the light-emitting device of one embodiment of the present invention has a low driving voltage, high emission efficiency, and a long lifetime, by the application of the light-emitting device of one embodiment of the present invention, a computer having high reliability and low power consumption can be obtained.

Figure 5C:
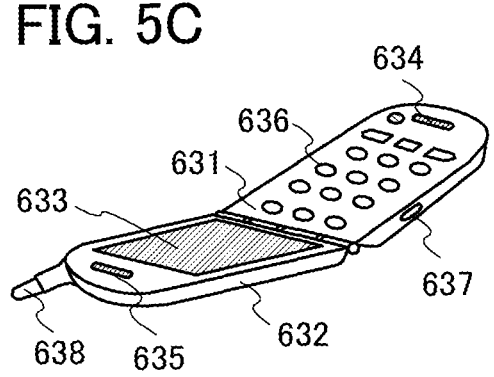

FIG. 5C illustrates a cellular phone according to one embodiment of the present invention, which includes a main body 631, a housing 632, a display portion 633, an audio input portion 634, an audio output portion 635, operation keys 636, an external connection port 637, an antenna 638, and the like. In this cellular phone, the light-emitting device of one embodiment of the present invention can be applied to the display portion 633. Since a light-emitting device of one embodiment of the present invention has a low driving voltage, high emission efficiency, and a long lifetime, by the application of the light-emitting device of one embodiment of the present invention, a cellular phone having high reliability and low power consumption can be obtained.

Figure 5D:
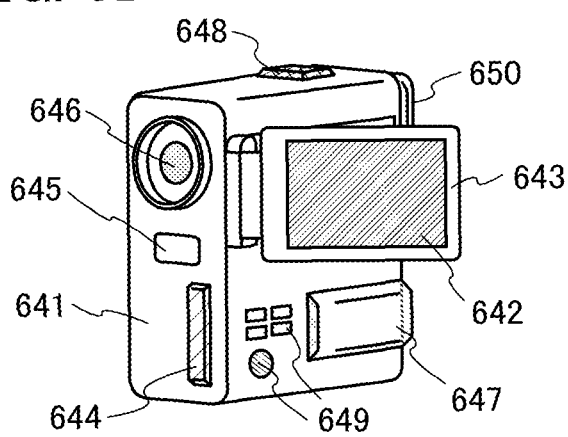

FIG. 5D illustrates a camera according to one embodiment of the present invention, which includes a main body 641, a display portion 642, a housing 643, an external connection port 644, a remote control receiving portion 645, an image receiving portion 646, a battery 647, an audio input portion 648, operation keys 649, an eyepiece portion 650, and the like. In this camera, the light-emitting device of one embodiment of the present invention can be applied to the display portion 642. Since the light-emitting device of one embodiment of the present invention has a low driving voltage, high emission efficiency, and a long lifetime, by the application of the light-emitting device of one embodiment of the present invention, a camera having high reliability and low power consumption can be obtained.

As described above, the applicable range of the light-emitting device of one embodiment of the present invention is so wide that the light-emitting device can be applied to electronic devices in a variety of fields. With use of a light-emitting device of one embodiment of the present invention, an electronic device having high reliability and low power consumption can be obtained.

The light-emitting device of one embodiment of the present invention can also be used as a lighting device. FIG. 6 illustrates an example of a liquid crystal display device using the light-emitting device of one embodiment of the present invention as a backlight. The liquid crystal display device illustrated in FIG. 6 includes a housing 701, a liquid crystal layer 702, a backlight 703, and a housing 704. The liquid crystal layer 702 is connected to a driver IC 705. The light-emitting device of one embodiment of the present invention is used as the backlight 703, and current is supplied through a terminal 706.

By use of the light-emitting device according to one embodiment of the present invention as a backlight of a liquid crystal display device as described above, a backlight having low power consumption can be obtained. Moreover, since the light-emitting device of one embodiment of the present invention is a lighting device for surface light emission and the enlargement of the light-emitting device is possible, the backlight can be made larger. Accordingly, a larger-area liquid crystal display device having low power consumption can be obtained.

Figure 7:
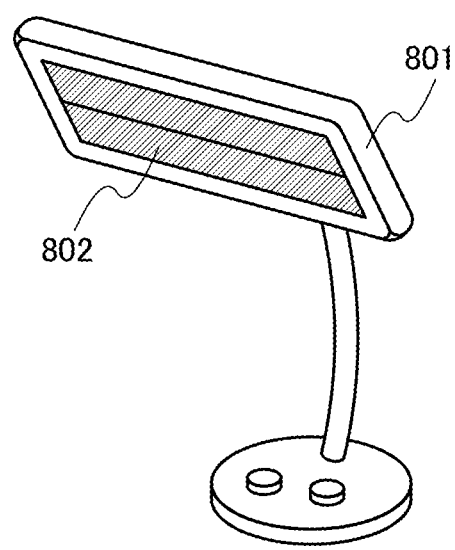
FIG. 7 illustrates a lighting device according to one embodiment of the present invention.

FIG. 7 illustrates an example in which the light-emitting device of one embodiment of the present invention is used for a desk lamp which is a lighting device. The desk lamp in FIG. 7 has a housing 801 and a light source 802, and the light-emitting device of one embodiment of the present invention is used as the light source 802. Since the light-emitting device of one embodiment of the present invention has a low driving voltage, high emission efficiency, and a long lifetime, by the application of the light-emitting device of one embodiment of the present invention, a desk lamp having high reliability and low power consumption can be obtained.

Figure 8:
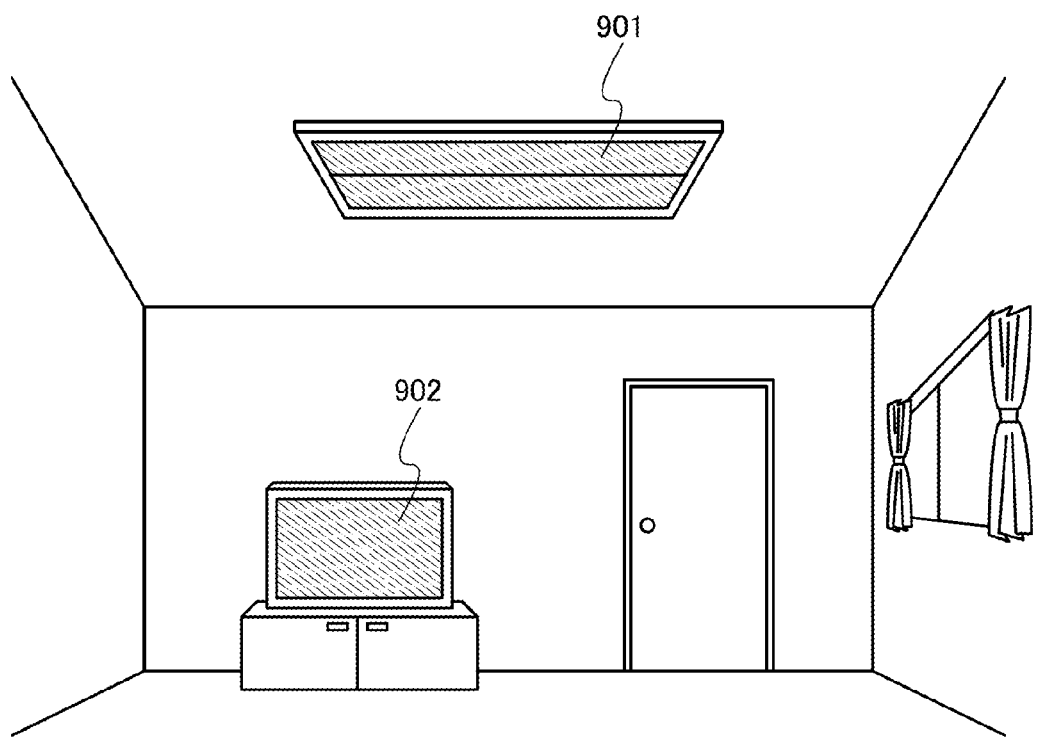
FIG. 8 illustrates a lighting device according to one embodiment of the present invention.

FIG. 8 illustrates an example in which the light-emitting device of one embodiment of the present invention is used for an indoor lighting device 901. Since the light-emitting device of one embodiment of the present invention can also have a larger area, the light-emitting device of one embodiment of the present invention can be used as a lighting system having a large area. Further, since the light-emitting device of one embodiment of the present invention has a low driving voltage, high emission efficiency, and a long lifetime, by the application of the light-emitting device of one embodiment of the present invention, a lighting device having high reliability and low power consumption can be obtained. In a room where the light-emitting device of one embodiment of the present invention is used as the indoor lighting device 901 as above, a television set 902 of one embodiment of the present invention as described referring to FIG. 5A can be installed so that public broadcasting and movies can be watched.

Figure 9A:
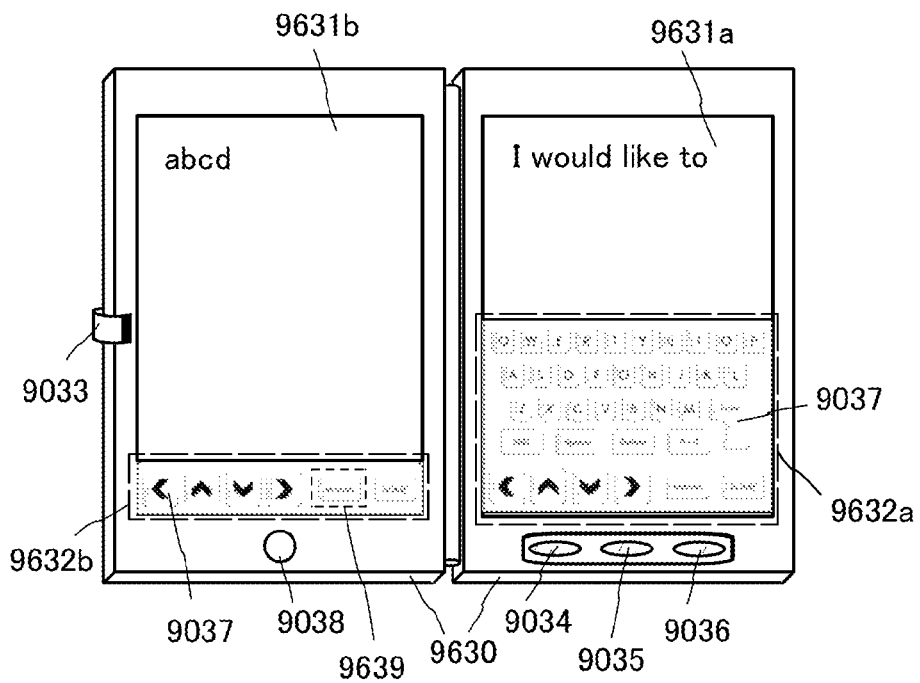
FIGS. 9A to 9C illustrate an electronic device according to one embodiment of the present invention.
Figure 9B:
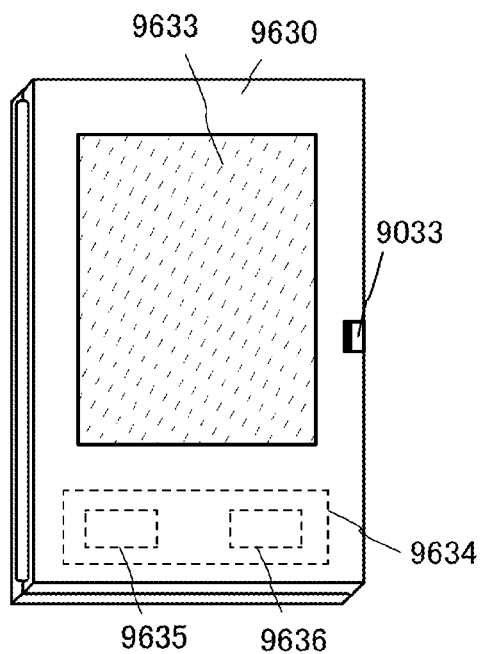

FIGS. 9A and 9B illustrate a tablet terminal that can be folded. In FIG. 9A, the tablet terminal is opened, and includes a housing 9630, a display portion 9631a, a display portion 9631b, a display-mode switching button 9034, a power button 9035, a power-saving-mode switching button 9036, a clip 9033, and an operation button 9038.

The tablet terminal is manufactured using the light-emitting device of one embodiment of the present invention for one or both of the display portion 9631a and the display portion 9631b.

A touch panel area 9632a can be provided in part of the display portion 9631a, in which area, data can be input by touching displayed operation keys 9037. Note that half of the display portion 9631a has only a display function and the other half has a touch panel function. However, one embodiment of the present invention is not limited to this structure, and the entire display portion 9631a may have a touch panel function. For example, a keyboard can be displayed on the entire display portion 9631a to be used as a touch panel, and the display portion 9631b can be used as a display screen.

A touch panel area 9632b can be provided in part of the display portion 9631b like in the display portion 9631a. When a keyboard display switching button 9639 displayed on the touch panel is touched with a finger, a stylus, or the like, a keyboard can be displayed on the display portion 9631b.

The touch panel area 9632a and the touch panel area 9632b can be controlled by touch input at the same time.

The display-mode switching button 9034 allows switching between a landscape mode and a portrait mode, color display and black-and-white display, and the like. The power-saving-mode switching button 9036 allows optimizing the display luminance in accordance with the amount of external light in use, which is detected by an optical sensor incorporated in the tablet terminal. In addition to the optical sensor, other detecting devices such as sensors for detecting inclination, like a gyroscope sensor or an acceleration sensor, may be incorporated in the tablet terminal.

Although the display portion 9631a and the display portion 9631b have the same display area in FIG. 9A, one embodiment of the present invention is not limited to this example. The display portion 9631a and the display portion 9631b may have different areas or different display quality. For example, higher definition images may be displayed on one of the display portions 9631a and 9631b.

FIG. 9B illustrates the tablet terminal folded, which includes the housing 9630, a solar battery 9633, a charge and discharge control circuit 9634, a battery 9635, and a DCDC converter 9636. Note that FIG. 9B shows an example in which the charge and discharge control circuit 9634 includes the battery 9635 and the DCDC converter 9636.

Since the tablet terminal can be folded, the housing 9630 can be closed when not in use. Thus, the display portions 96311a and 9631b can be protected, which makes it possible to provide a tablet terminal with high durability and improved reliability for long-term use.

The tablet terminal illustrated in FIGS. 9A and 9B can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs).

The solar battery 9633, which is attached on the surface of the tablet terminal, supplies electric power to a touch panel, a display portion, an image signal processor, and the like. Note that a structure in which the solar battery 9633 is provided on one or both surfaces of the housing 9630 is preferable because the battery 9635 can be charged efficiently. The use of a lithium ion battery as the battery 9635 is advantageous in downsizing or the like.

Figure 9C:
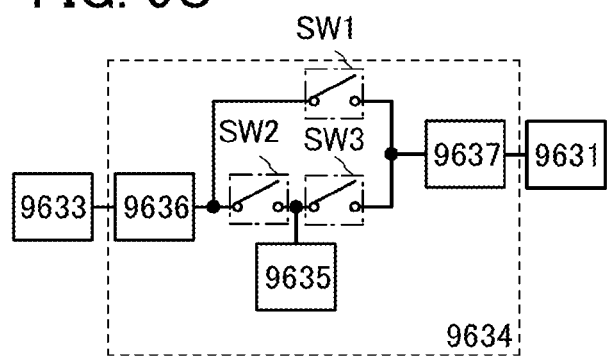

The structure and operation of the charge and discharge control circuit 9634 illustrated in FIG. 9B are described with reference to a block diagram of FIG. 9C. FIG. 9C illustrates the solar battery 9633, the battery 9635, the DCDC converter 9636, a converter 9637, switches SW1 to SW3, and the display portion 9631. The battery 9635, the DCDC converter 9636, the converter 9637, and the switches SW1 to SW3 correspond to the charge and discharge control circuit 9634 in FIG. 9B.

First, description is made on an example of the operation in the case where power is generated by the solar battery 9633 using external light. The voltage of power generated by the solar battery 9633 is raised or lowered by the DCDC converter 9636 so that a voltage for charging the battery 9635 is obtained. When the display portion 9631 is operated with the power from the solar battery 9633, the switch SW1 is turned on and the voltage of the power is raised or lowered by the converter 9637 to a voltage needed for operating the display portion 9631. When display is not performed on the display portion 9631, the switch SW1 is turned off and the switch SW2 is turned on so that the battery 9635 can be charged.

Although the solar battery 9633 is shown as an example of a power generation means, there is no particular limitation and the battery 9635 may be charged with another power generation means such as a piezoelectric element or a thermoelectric conversion element (Peltier element). For example, the battery 9635 may be charged with a non-contact power transmission module which is capable of charging by transmitting and receiving power wirelessly (without contact), or another charge means used in combination.

This embodiment can be implemented in appropriate combination with the other embodiments.

EXAMPLE 1

SYNTHESIS EXAMPLE 1

This example shows a method of synthesizing 2-[4-(naphthalen-1-yl)phenyl]dibenzo[f,h]quinoxaline (abbreviation: NPDBq) represented by the following structural formula (101).

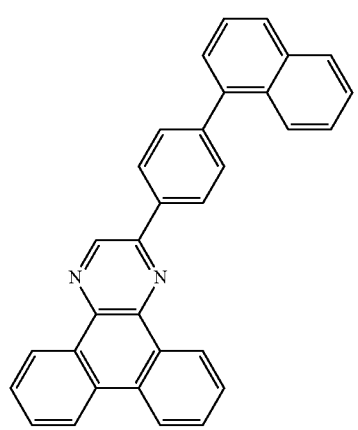

(101)

NPDBq (Synthesis of NPDBq)

A synthesis scheme of NPDBq is illustrated in (C-1).

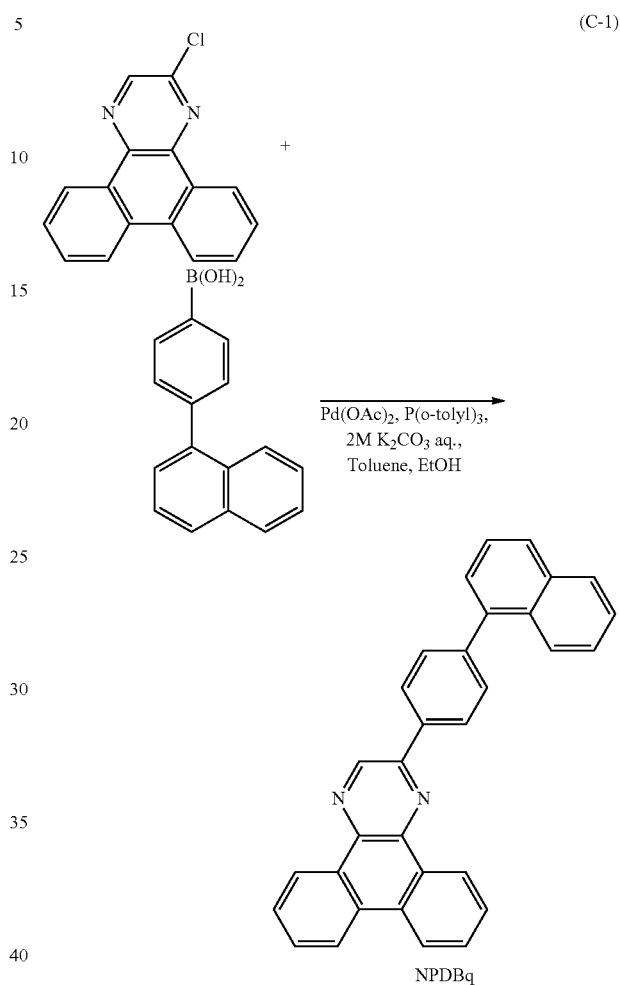

(C-1)

NPDBq

In a 200 mL three-neck flask, a mixture of 2.7 g (10 mmol) of 2-chlorodibenzo[f,h]quinoxaline, 2.7 g (11 mmol) of 4-(1-naphthyl)phenylboronic acid, 23 mg (0.1 mmol) of palladium (II) acetate, 91 mg (0.3 mmol) of tri(ortho-tolyl)phosphine, 43 mL of toluene, 4 mL of ethanol, and 14 mL of an aqueous solution of potassium carbonate (2 mol/L) was degassed while being stirred under reduced pressure, and was then reacted by being heated and stirred under a nitrogen atmosphere at 80° C. for 12 hours.

After the reaction, 500 mL of toluene was added to this reaction mixture solution, and an organic layer of the mixture solution was filtered through Florisil (produced by Wako Pure Chemical Industries, Ltd., Catalog No. 540-00135), alumina (produced by Merck & Co., Inc., neutral), and Celite (produced by Wako Pure Chemical Industries, Ltd., catalog No. 531-16855). The obtained filtrate was washed with water, and magnesium sulfate was added thereto so that moisture was adsorbed. This suspension was filtered to obtain a filtrate. The resulting filtrate was concentrated, followed by purification using silica gel column chromatography. At this time, a mixed solvent of toluene and hexane in a ratio of 1:5 was used as a developing solvent for the chromatography. The obtained fraction was concentrated, and methanol was added thereto. The mixture was irradiated with supersonic and then recrystallized, so that the objective substance was obtained as 3.0 g of yellow powder in a yield of 69%.

The Rf values of the objective substance and 2-chlorodibenzo[f,h]quinoxaline were respectively 0.33 and 0.55, which were found by silica gel thin layer chromatography (TLC) (with a developing solvent of ethyl acetate and hexane in a ratio of 1:10).

A nuclear magnetic resonance (NMR) method identified this compound as 2-[4-(naphthalen-1-yl)phenyl]dibenzo[f,h]quinoxaline (abbreviation: NPDBq), which was the objective substance.

$^1$H NMR data of the obtained substance are as follows: $^1$H NMR (CDCl$_3$, 300 MHz): δ (ppm)=7.47-7.62 (m, 4H), 7.75-8.03 (m, 9H), 8.50 (d, J=8.3 Hz, 2H), 8.68 (d, J=7.3 Hz, 2H), 9.27 (d, J=7.8 Hz, 1H), 9.46-9.50 (m, 2H).

Figure 10A:
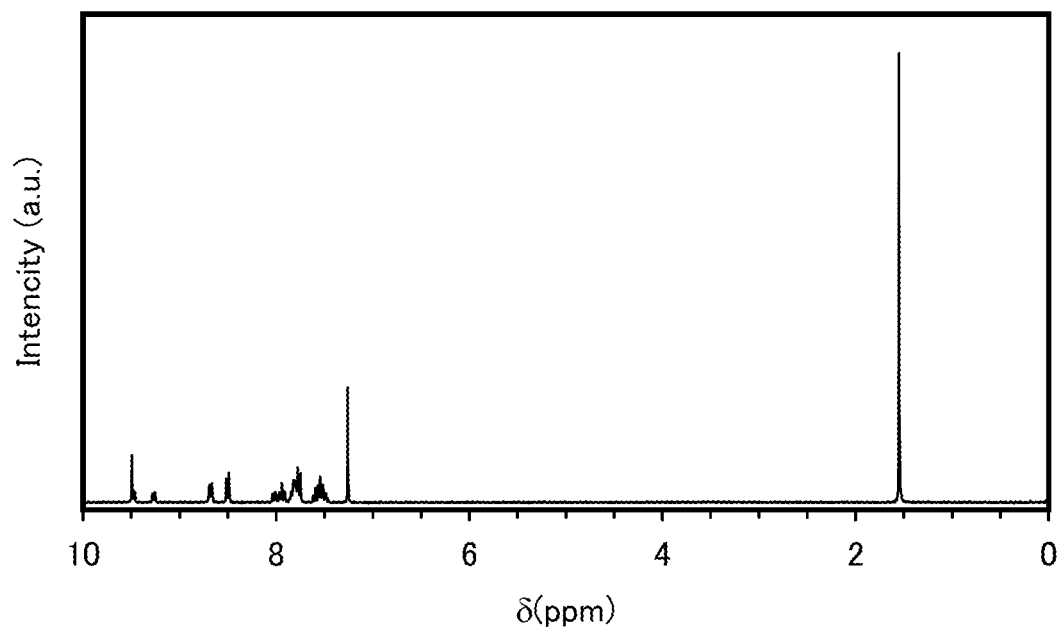
FIGS. 10A and 10B show $^1$H NMR charts of 2-[4-(naphthalen-1-yl)phenyl]dibenzo[f,h]quinoxaline (abbreviation: NPDBq).
Figure 10B:
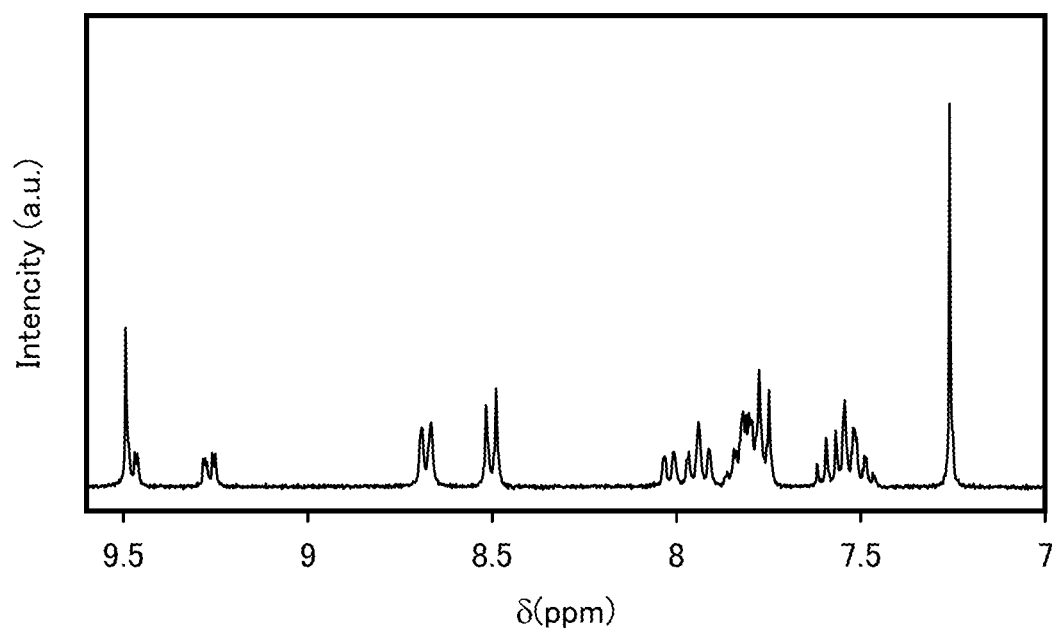

The $^1$H NMR chart is shown in FIGS. 10A and 10B. Note that FIG. 10B is a chart showing an enlarged part of FIG. 10A in the range of 7.00 ppm to 9.60 ppm.

Figure 11A:
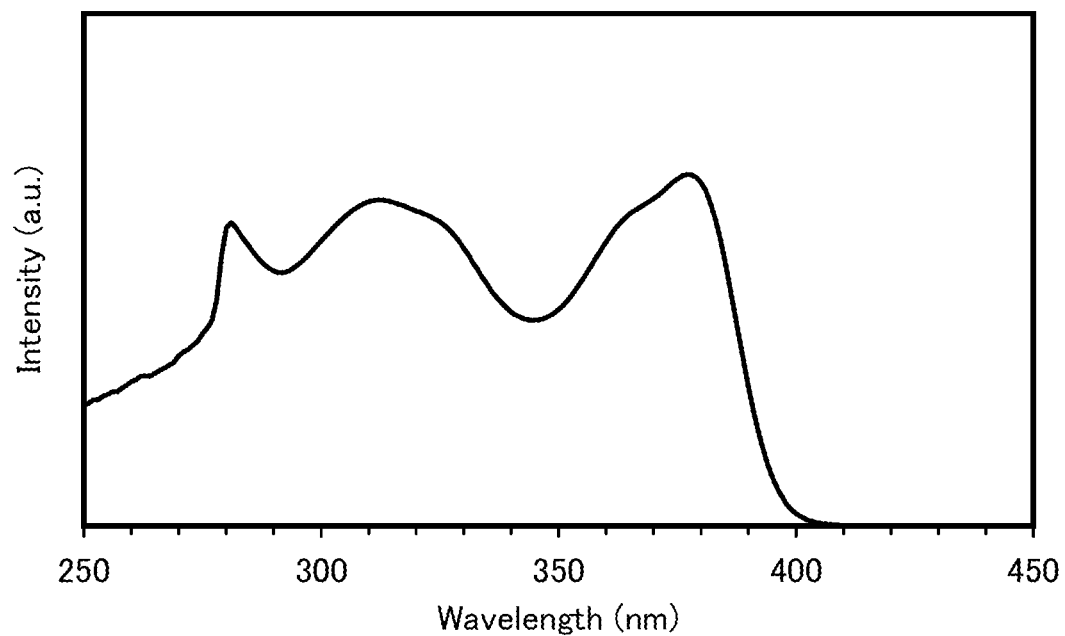
FIGS. 11A and 11B show an absorption spectrum and an emission spectrum of a toluene solution of NPDBq.
Figure 11B:
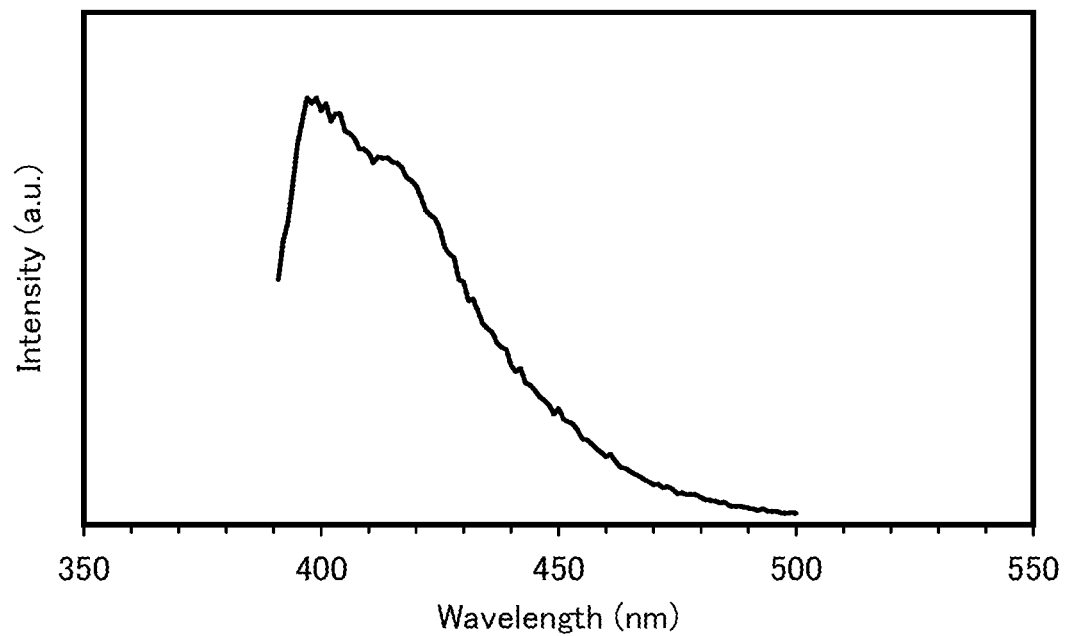
Figure 12A:
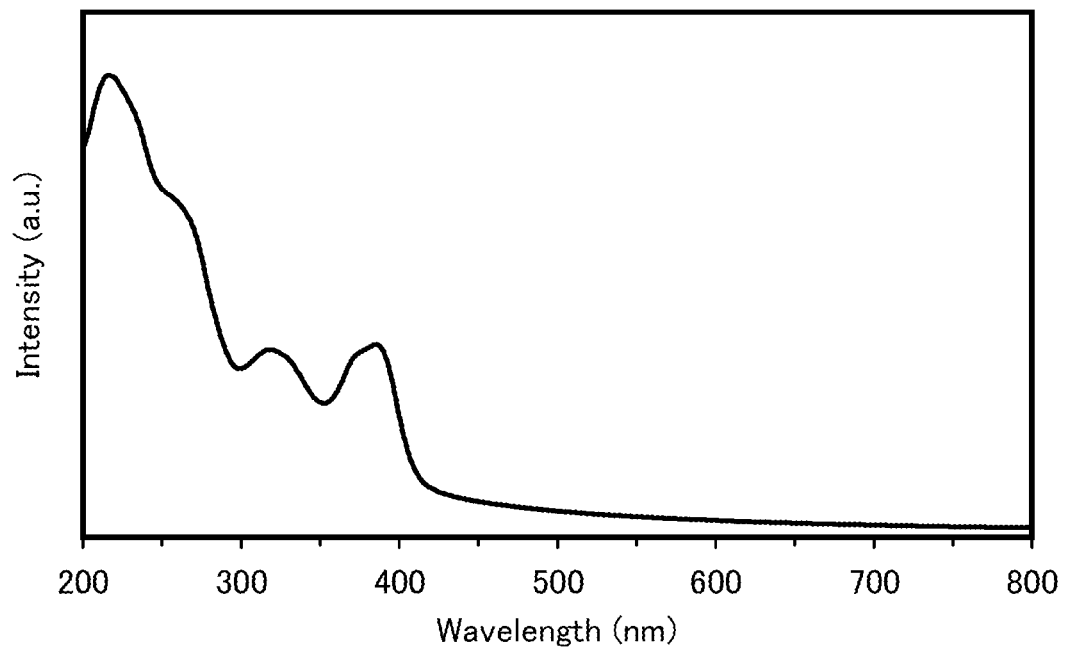
FIGS. 12A and 12B show an absorption spectrum and an emission spectrum of a thin film of NPDBq.
Figure 12B:
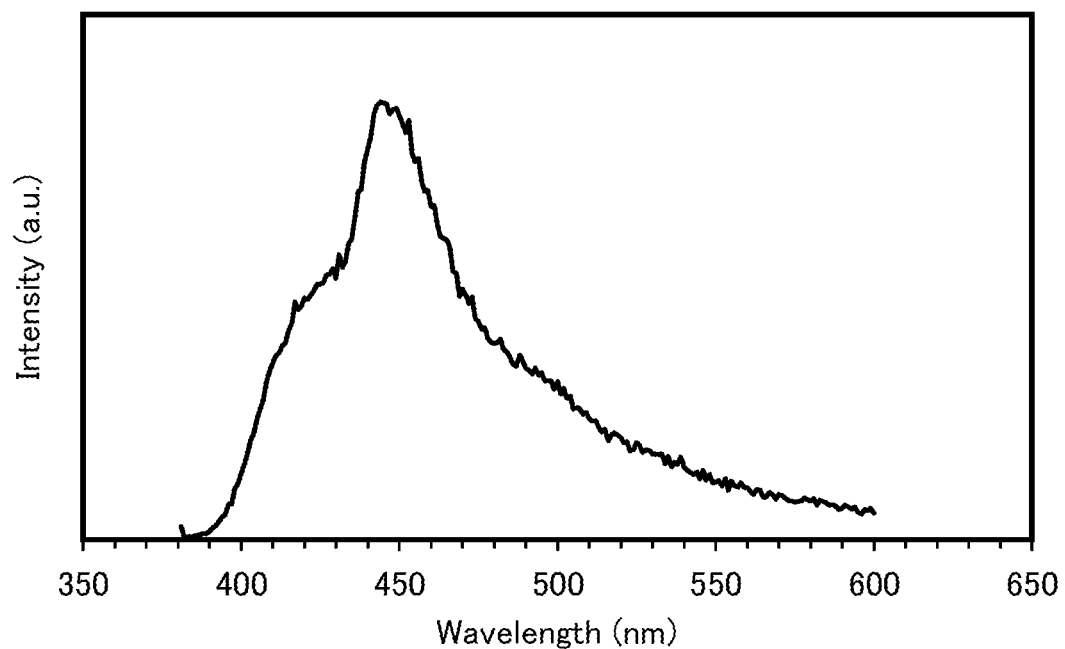

Further, FIG. 11A shows an absorption spectrum of a toluene solution of NPDBq, and FIG. 11B shows an emission spectrum thereof. In addition, FIG. 12A shows the absorption spectrum of a thin film of NPDBq, and FIG. 12B shows the emission spectrum thereof. The measurement of the absorption spectrum was conducted by using a UV-visible spectrophotometer (V-550, produced by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from the spectrum of the solution, and the absorption spectrum of the thin film was obtained by subtracting the absorption spectrum of a quartz substrate from the spectrum of the thin film. In FIGS. 11A and 11B and FIGS. 12A and 12B, the horizontal axis represents wavelength (nm) and the vertical axis represents intensity (arbitrary unit). In the case of the toluene solution, an absorption peak was observed at around 377 nm, and an emission wavelength peak was 398 nm. In the case of the thin film, an absorption peak was observed at around 385 nm, and emission wavelength peaks were 429 nm, 445 nm, and 488 nm (at an excitation wavelength of 378 nm).

Electrochemical characteristics of a thin film of NPDBq were measured (the measuring instrument was AC-2 produced by Riken Keiki, Co., Ltd.). Note that the measurement of electrochemical characteristics of the thin film was carried out as follows.

The value of the HOMO level was obtained by conversion of the value of the ionization potential measured with a photoelectron spectrometer (AC-2, produced by Riken Keiki Co., Ltd.) in the air into a negative value. The value of the LUMO level was obtained in such a manner that the absorption edge, which was obtained from Tauc plot with an assumption of direct transition using data on the absorption spectrum of the thin film, was regarded as an optical energy gap and was added to the value of the HOMO level.

From the results of the measurement of electrochemical characteristics of the thin film, the HOMO level, the LUMO level, and the band gap (Bg) were found to be −5.84 eV, −2.78 eV, and 3.06 eV, respectively.

The above results reveal that NPDBq has a relatively deep HOMO level, a relatively shallow LUMO level, and a relatively wide Bg.

Electrochemical characteristics of an NPDBq solution were also measured.

As a measuring method, cyclic voltammetry (CV) measurement was employed. An electrochemical analyzer (ALS model 600A or 600C, produced by BAS Inc.) was used for the measurement.

The value of the HOMO level was found to be −6.21 eV, indicating that NPDBq can efficiently inject holes into a material having a HOMO level whose value is close to this value. Further, since the HOMO level is deep (the value thereof is small), it is found that NPDBq can efficiently inject holes into a material having a shallower HOMO level (a larger value) than NPDBq.

The value of the LUMO level was found to be −2.95 eV, indicating that NPDBq can efficiently inject electrons into a material having a LUMO level whose value is close to this value. Further, since the LUMO level is shallow (the value thereof is large), it is found that NPDBq can efficiently inject electrons into a material having a deeper LUMO level (a smaller value) than NPDBq. In addition, the reduction peak was at a similar value even after 100 cycles. This indicates that NPDBq has properties effective against repetition of redox reactions between a reduced state and a neutral state.

Note that the above-described cyclic voltammetry (CV) measurement was carried out as follows.

As for a solution used for the CV measurement, dehydrated dimethylformamide (DMF, produced by Sigma-Aldrich Co. LLC., 99.8%, catalog No. 22705-6) was used as a solvent, and tetra-n-butylammonium perchlorate (n-Bu$_4$NClO$_4$, produced by Tokyo Chemical Industry Co., Ltd., catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 2 mmol/L. A platinum electrode (produced by BAS Inc., PTE platinum electrode) was used as a working electrode, a platinum electrode (produced by BAS Inc., Pt counter electrode for VC-3 (5 cm)) was used as an auxiliary electrode, and an Ag/Ag$^+$ electrode (produced by BAS Inc., RE-7 reference electrode for nonaqueous solvent) was used as a reference electrode. Note that the measurement was conducted at room temperature (20° C. to ° C.). In addition, the scan rate at the CV measurement was set to 0.1 V/sec in all the measurement.

(Calculation of the Potential Energy of the Reference Electrode with Respect to the Vacuum Level)

First, a potential energy (eV) of the reference electrode (Ag/Ag$^+$ electrode), which was used in this example, with respect to the vacuum level was calculated. In other words, Fermi level of the Ag/Ag$^+$ electrode was calculated. It is known that the oxidation-reduction potential of ferrocene in methanol is +0.610 [V vs. SHE] with respect to the standard hydrogen electrode (Reference: Christian R. Goldsmith et al., J. Am. Chem. Soc., Vol. 124, No. 1, 83-96, 2002).

On the other hand, using the reference electrode used in this example, the oxidation-reduction potential of ferrocene in methanol was calculated to be +0.11 [V vs. Ag/Ag$^+$]. Thus, it was found that the potential energy of the reference electrode used in this example was lower than that of the standard hydrogen electrode by 0.50 [eV].

Note that it is known that the potential energy of the standard hydrogen electrode from the vacuum level is −4.44 eV (Reference: Toshihiro Ohnishi and Tamami Koyama, High molecular EL material, Kyoritsu shuppan, pp. 64-67). Accordingly, the potential energy of the reference electrode, which was used in this example, with respect to the vacuum level could be calculated as follows: −4.44−0.50=−4.94 [eV].

The measurement of the oxidation reaction characteristics of the compound of this example was performed by the steps of scanning the potential of the working electrode with respect to the reference electrode in ranges of about 0.2 V to about 1.5 V, and then about 1.5 V to about 0.2 V.

Subsequently, the calculation of the HOMO level of the objective substance based on CV measurement is described in detail. In the measurement of the oxidation reaction characteristics, an oxidation peak potential $E_{pa}$ [V] and a reduction peak potential $E_{pc}$ [V] were calculated. Accordingly, a half-wave potential (intermediate potential between $E_{pa}$ and $E_{pc}$) can be calculated by $(E_{pa}+E_{pc})/2$ [V]. This means that the compound of this example is oxidized by an electric energy corresponding to the value of the half-wave potential [V vs. Ag/Ag$^+$], and this energy corresponds to the HOMO level.

The reduction reaction characteristics of the compound of this example were measured in the following manner: the potential of the working electrode with respect to the reference electrode was scanned from about −1.4 V to about −2.1 V, and then from about −2.1 V to about −1.4 V.

Subsequently, the calculation of the LUMO level of the objective substance based on CV measurement is described in detail. In the measurement of the reduction reaction characteristics, a reduction peak potential $E_{pc}$ [V] and an oxidation peak potential $E_{pa}$ [V] were calculated. Accordingly, a half-wave potential (intermediate potential between $E_{pa}$ and $E_{pc}$) can be calculated by $(E_{pa}+E_{pc})/2$ [V]. This means that the compound of this example is reduced by an electric energy corresponding to the value of the half-wave potential [V vs. Ag/Ag$^+$], and this energy corresponds to the LUMO level.

Next, NPDBq obtained in this example was analyzed by liquid chromatography mass spectrometry (LC/MS).

Figure 42A:
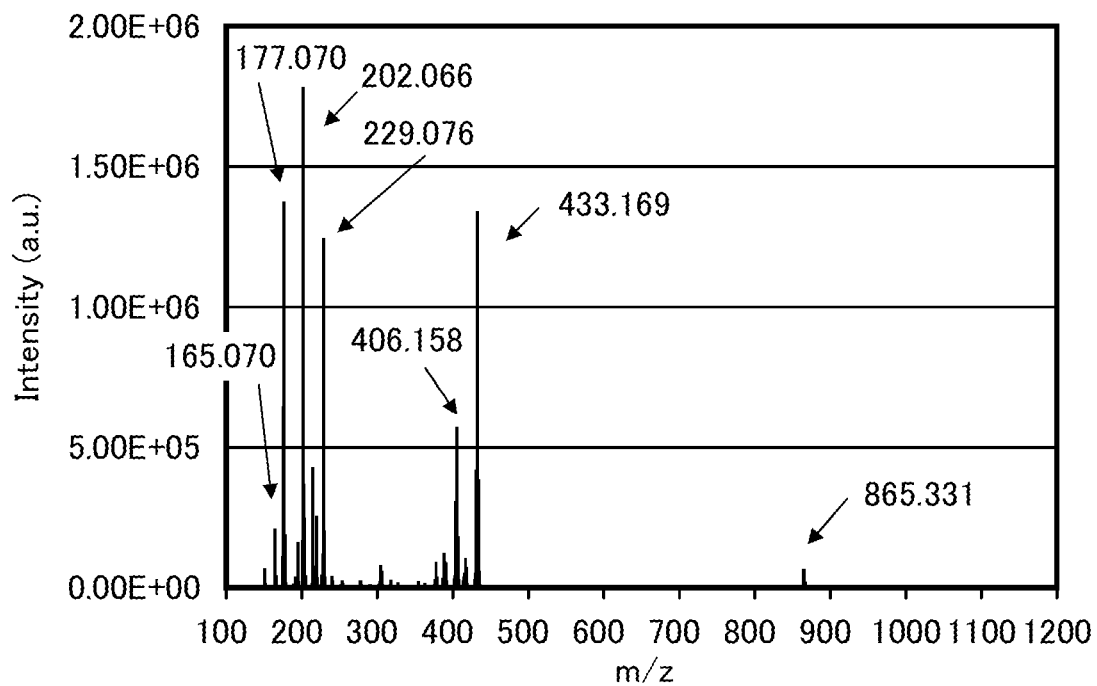
FIGS. 42A and 42B show results of LC/MS analysis of NPDBq.
Figure 42B:
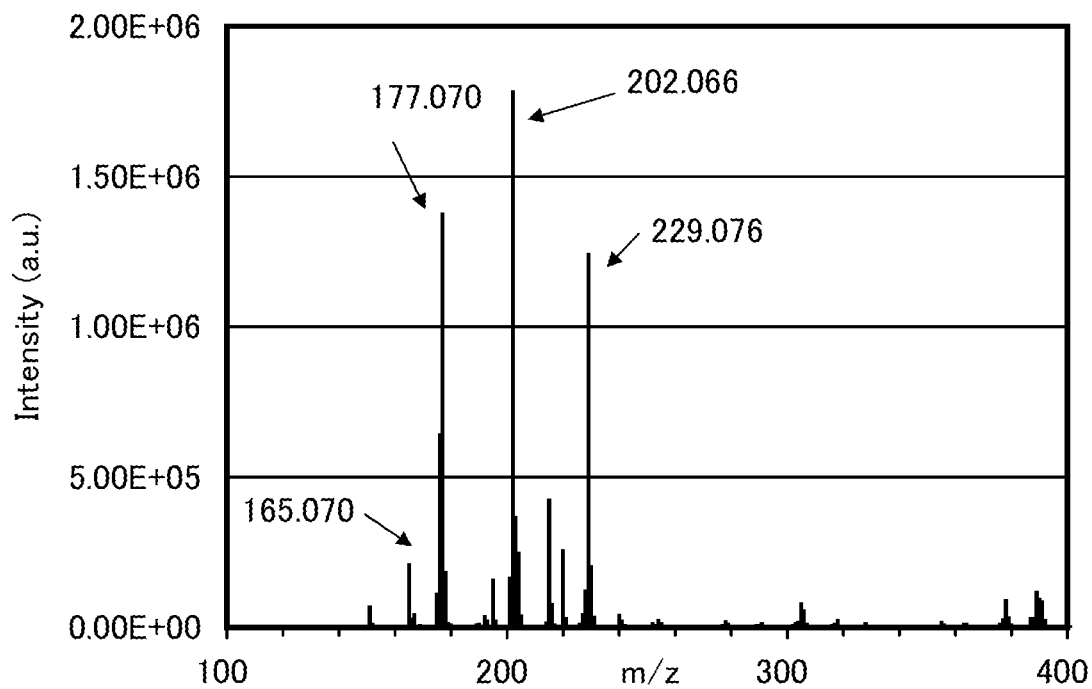

The analysis by LC/MS was carried out with Acquity UPLC (manufactured by Waters Corporation), and Xevo G2 T of MS (manufactured by Waters Corporation). In the MS analysis, ionization was carried out by an electrospray ionization (ESI) method. Capillary voltage and sample cone voltage were set to 3.0 kV and 30 V, respectively. Detection was performed in a positive mode. A component which underwent the ionization under the above conditions was collided with an argon gas in a collision cell to dissociate into product ions. Energy (collision energy) for the collision with argon was 50 eV. The mass range for the analysis was m/z=100 to 1200. FIGS. 42A and 42B show the results of the analysis.

The results in FIGS. 42A and 42B show that, owing to the presence and absence of hydrogen ions and isotopes, a plurality of peaks derived from product ions of NPDBq are detected mainly around m/z 406, m/z 229, m/z 202, m/z 177, and m/z 165. The results in FIGS. 42A and 42B are characteristically derived from NPDBq and thus can be regarded as important data in identification of NPDBq contained in a mixture.

Peaks around m/z 406 are presumed to be derived from product ions of cations in the state where one C atom and one N atom are dissociated from the dibenzo[f,h]quinoxaline ring in NPDBq. This is one of features of the heterocyclic compound according to one embodiment of the present invention. In particular, this is one of features of the heterocyclic compound according to one embodiment of the present invention in which a substituent(s) (in NPDBq, a phenylene group and a naphthalene skeleton) is bonded to the 2-position of the dibenzo[f,h]quinoxaline ring.

Peaks around m/z 229 are presumed to be derived from product ions of cations of a diazatriphenylenyl group such as a dibenzo[f,h]quinoxaline ring. Peaks around m/z 202, m/z 177, and m/z 165 are also detected, indicating that NPDBq, which is the heterocyclic compound according to one embodiment of the present invention, includes a dibenzo[f,h]quinoxaline ring.

Measurement of NPDBq with a time-of-flight secondary ion mass spectrometer (TOF-SIMS) was further performed, and FIGS. 43A and 43B and FIGS. 44A and 44B show the qualitative spectra (positive and negative ions).

Note that FIGS. 43A and 43B each show measurement results of positive ions. In FIG. 43A, the horizontal axis represents m/z in the range of 0 to 500, and the vertical axis represents intensity (arbitrary unit). In FIG. 43B, the horizontal axis represents m/z in the range of 400 to 1200, and the vertical axis represents intensity (arbitrary unit). Further, FIGS. 44A and 44B each show measurement results of negative ions. In FIG. 44A, the horizontal axis represents m/z in the range of 0 to 400, and the vertical axis represents intensity (arbitrary unit). In FIG. 44B, the horizontal axis represents m/z in the range of 400 to 1200, and the vertical axis represents intensity (arbitrary unit).

TOF.SIMS 5 (manufactured by ION-TOF GmbH) was used, where $Bi_3^{++}$ was used as a primary ion source. Note that irradiation with the primary ions was performed in a pulsed manner with a pulse width of 7 nm to 12 nm. The irradiation amount was greater than or equal to 8.2 E10 ions/cm$^2$ and less than or equal to 6.7 E11 ions/cm$^2$ (less than or equal to 1 E12 ions/cm$^2$), acceleration voltage was 25 eV, and a current value was 0.2 pA. A powder of NPDBq was the sample used for the measurement.

The results in FIGS. 43A and 43B reveal that, owing to the presence and absence of hydrogen ions and isotopes, a plurality of peaks derived from precursor ions of NPDBq are detected mainly around m/z 433. Owing to the presence and absence of hydrogen ions and isotopes, a plurality of peaks derived from product ions around m/z 226, m/z 202, m/z 176, and m/z 165 are also detected, indicating that NPDBq includes a dibenzo[f,h]quinoxaline ring. Note that the measurement results with a TOF-SIMS can be similarly regarded as important data in identification of NPDBq contained in a mixture.

The results in FIGS. 44A and 44B reveal that, owing to the presence and absence of hydrogen ions and isotopes, NPDBq mainly has a plurality of peaks derived from product ions around m/z 419, peaks derived from precursor ions around m/z 433, peaks derived from oligomers of product ions around m/z 849, and peaks of dimmer ions around m/z 863 and m/z 875. The results in FIGS. 44A and 44B are characteristically derived from NPDBq and thus can be regarded as important data in identification of NPDBq contained in a mixture.

Peaks around m/z 419 are presumed to be derived from product ions of radical cations in the state where one N atom is removed from the dibenzo[f,h]quinoxaline ring in NPDBq. This is one of features of the heterocyclic compound according to one embodiment of the present invention. In particular, this is one of features of the heterocyclic compound according to one embodiment of the present invention in which a substituent(s) (in NPDBq, a phenylene group and a naphthalene skeleton) is bonded to the 2-position of the dibenzo[f,h]quinoxaline ring.

EXAMPLE 2

SYNTHESIS EXAMPLE 2

This example shows a method of synthesizing 2-[3-(phenanthren-9-yl)phenyl]dibenzo[f,h]quinoxaline (abbreviation: mPnPDBq) represented by the following structural formula (104).

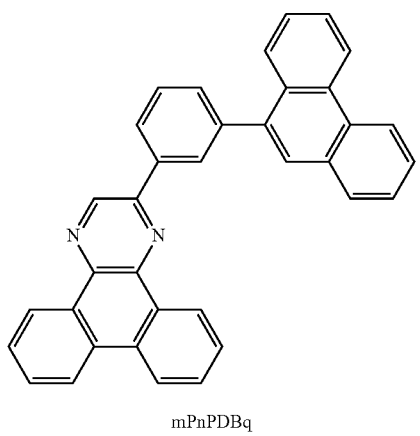

mPnPDBq (Synthesis of mPnPDBq)
A synthesis scheme of mPnPDBq is illustrated in (D-1).

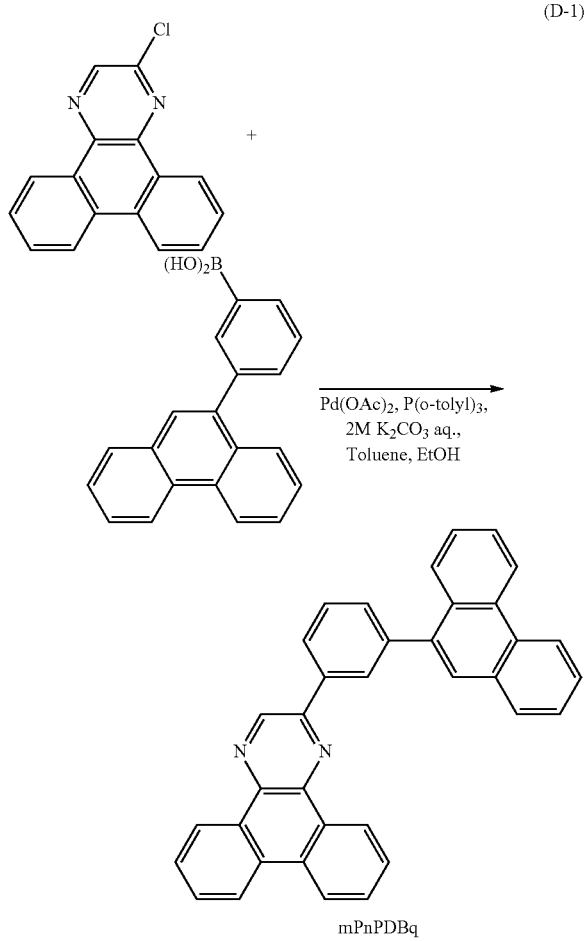

(D-1)

mPnPDBq

In a 200 mL three-neck flask, a mixture of 1.6 g (6.1 mmol) of 2-chlorodibenzo[f,h]quinoxaline, 2.0 g (6.71 mmol) of 3-(phenanthren-9-yl)phenylboronic acid, 47 mg (0.2 mmol) of palladium(II) acetate, 190 mg (0.6 mmol) of tri(ortho-tolyl)phosphine, 30 mL of toluene, 3 mL of ethanol, and mL of an aqueous solution of potassium carbonate (2 mol/L) was degassed while being stirred under reduced pressure, and was then reacted by being heated and stirred under a nitrogen atmosphere at 100° C. for 14 hours.

After the reaction, 500 mL of toluene was added to the reaction mixture solution, and an organic layer of the mixture solution was filtered through alumina (produced by Merck & Co., Inc., neutral) and Celite (produced by Wako Pure Chemical Industries, Ltd., catalog No. 531-16855). The obtained filtrate was washed with water, and magnesium sulfate was added thereto so that moisture was adsorbed. This suspension was filtered to obtain a filtrate. The obtained filtrate was concentrated and purified by silica gel column chromatography. At this time, a mixed solvent of toluene was used as a developing solvent for the chromatography. The obtained fraction was concentrated, and toluene was added thereto. The mixture was irradiated with supersonic and then recrystallized, so that the objective substance was obtained as 0.60 g of white powder in a yield of 20%.

The Rf values of the objective substance and 2-chlorodibenzo[f,h]quinoxaline were respectively 0.55 and 0.75, which were found by silica gel thin layer chromatography (TLC) (with a developing solvent of toluene).

A nuclear magnetic resonance (NMR) method identified this compound as 2-[3-(phenanthren-9-yl)phenyl]dibenzo[f,h]quinoxaline (abbreviation: mPnPDBq), which was the objective substance.

$^1$H NMR data of the obtained substance are as follows: $^1$H NMR (CDCl$_3$, 300 MHz): δ (ppm)=7.59-7.85 (m, 11H), 7.97 (d, J=6.8 Hz, 1H), 8.03 (d, J=7.8 Hz, 1H), 8.45 (d, J=6.8 Hz, 1H), 8.56 (s, 1H), 8.66 (d, J=7.8 Hz, 2H), 8.79 (d, J=8.8 Hz, 1H), 8.84 (d, J=8.3 Hz, 1H), 9.25 (d, J=7.8 Hz, 1H), 9.39 (d, J=9.3 Hz, 1H), 9.47 (s, 1H).

Figure 13A:
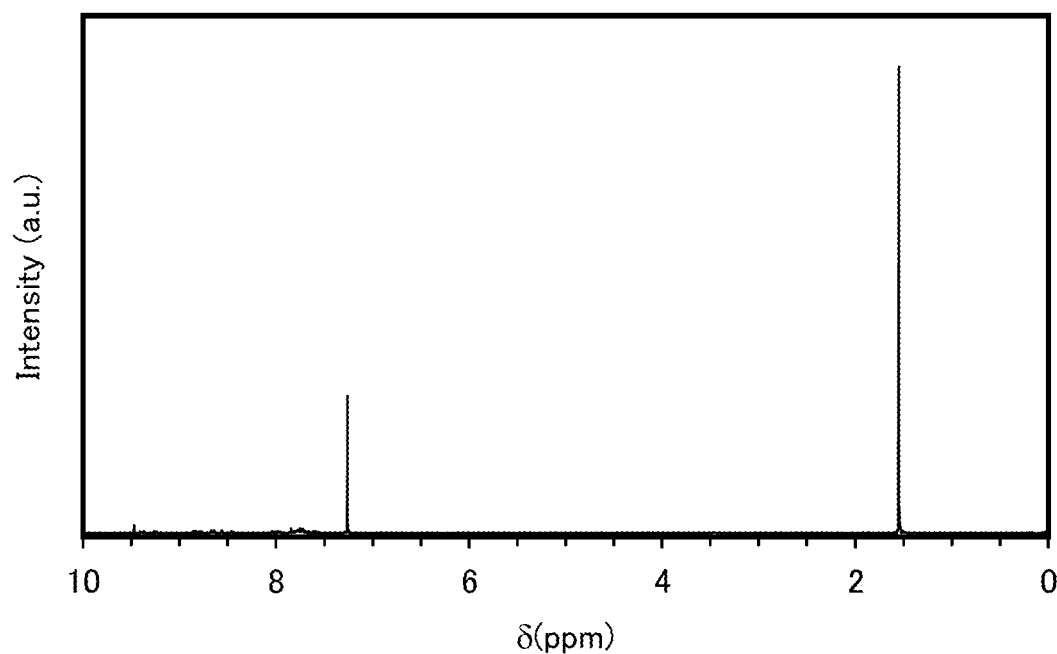
FIGS. 13A and 13B show $^1$H NMR charts of 2-[3-(phenanthren-9-yl)phenyl]dibenzo[f,h]quinoxaline (abbreviation: mPnPDBq).
Figure 13B:
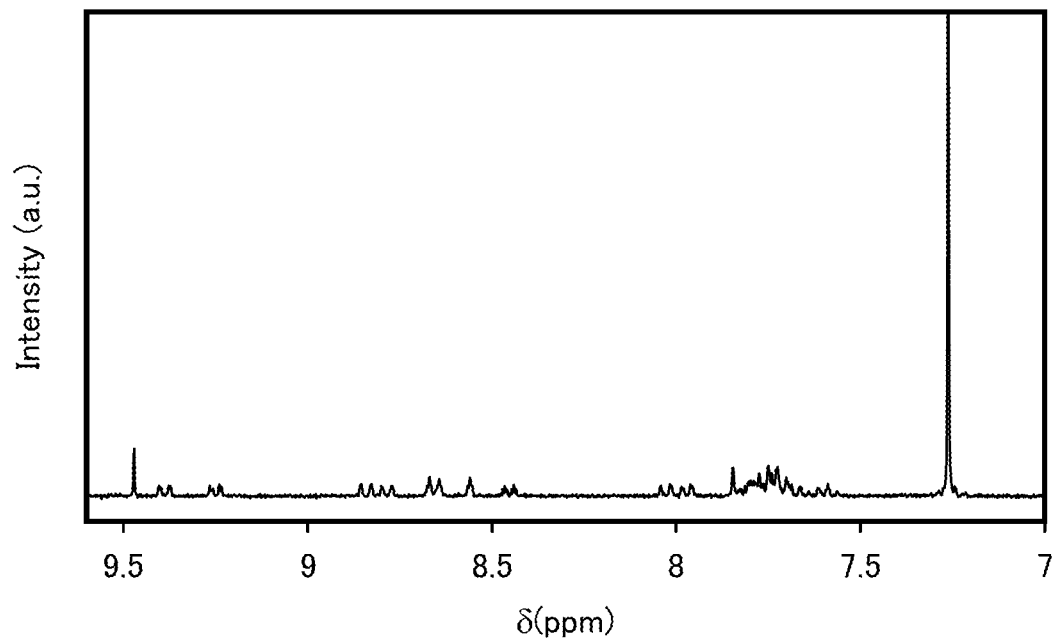

The $^1$H NMR chart is shown in FIGS. 13A and 13B. Note that FIG. 13B is a chart showing an enlarged part of FIG. 13A in the range of 7.00 ppm to 9.60 ppm.

Figure 14A:
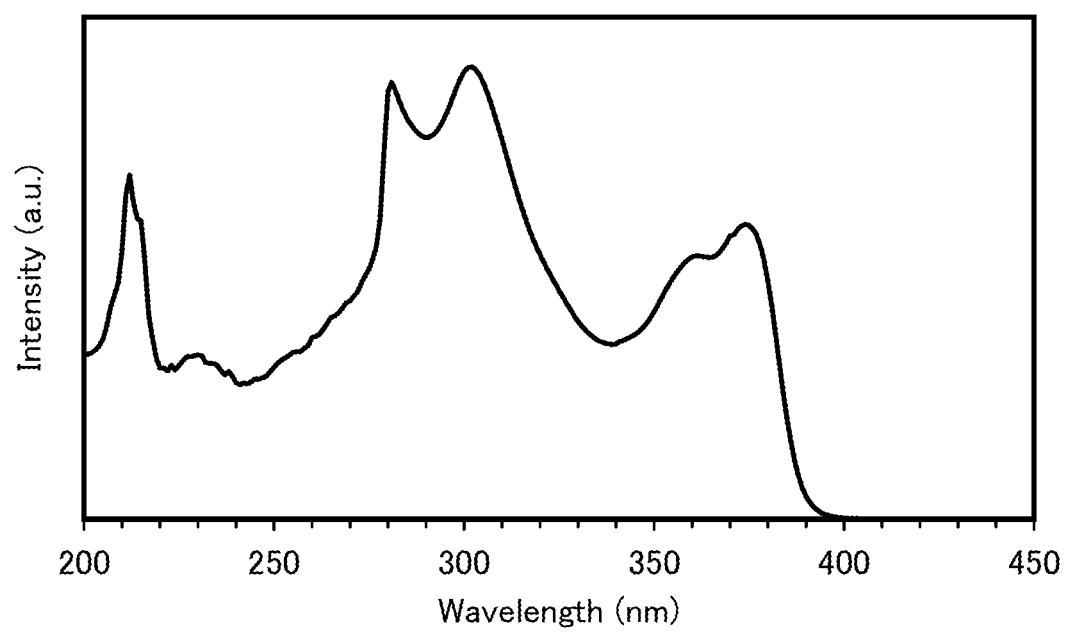
FIGS. 14A and 14B show an absorption spectrum and an emission spectrum of a toluene solution of mPnPDBq.
Figure 14B:
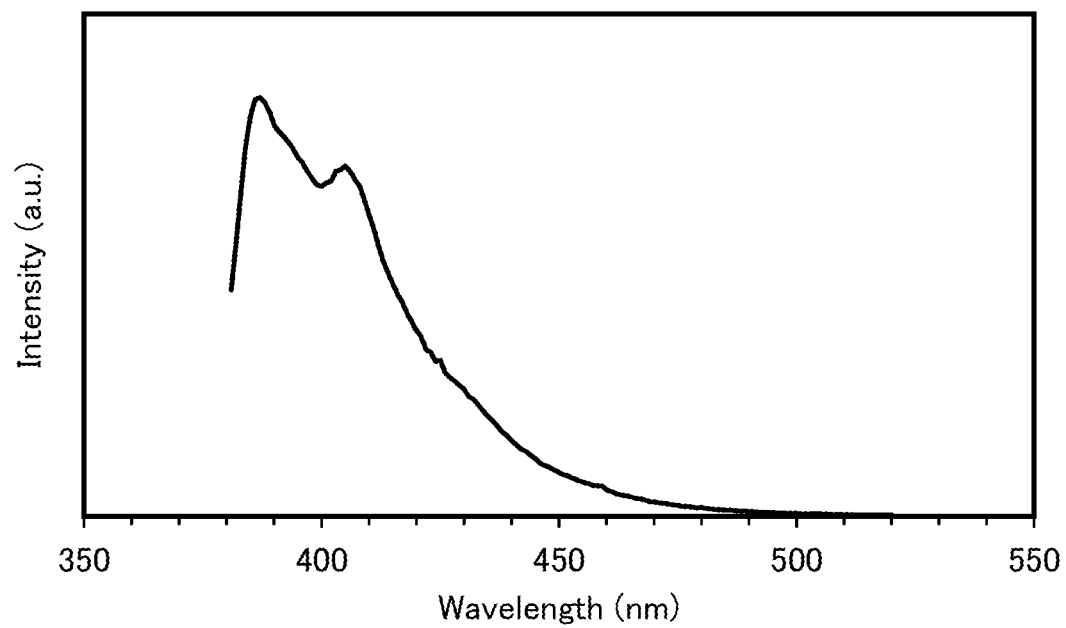
Figure 15A:
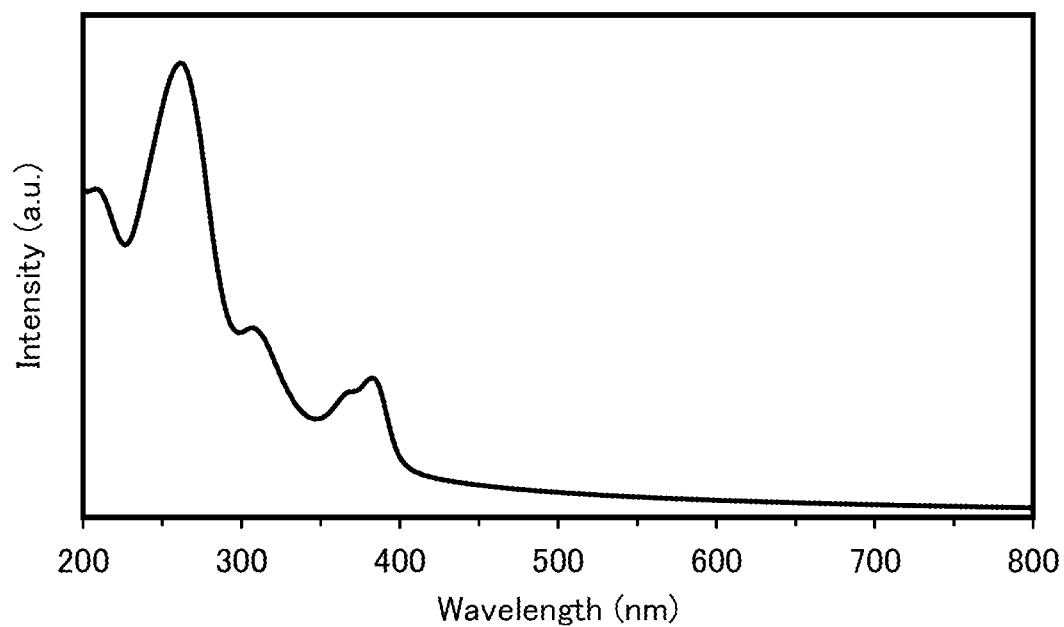
FIGS. 15A and 15B show an absorption spectrum and an emission spectrum of a thin film of mPnPDBq.
Figure 15B:
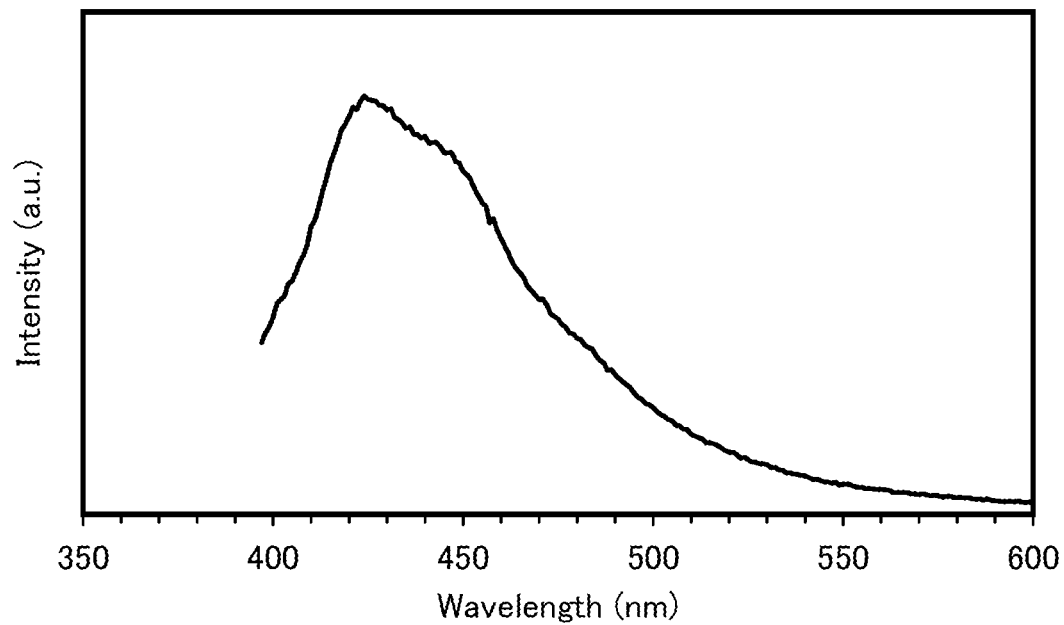

Further, FIG. 14A shows an absorption spectrum of a toluene solution of mPnPDBq, and FIG. 14B shows an emission spectrum thereof. FIG. 15A shows an absorption spectrum of a thin film of mPnPDBq, and FIG. 15B shows an emission spectrum thereof. The absorption spectra were obtained in the same manner as Example 1. In FIGS. 14A and 14B and FIGS. 15A and 15B, the horizontal axis represents wavelength (nm) and the vertical axis represents intensity (arbitrary unit). In the case of the toluene solution, an absorption peak was observed at around 372 nm, and emission wavelength peaks were 387 nm and 406 nm (at an excitation wavelength of 362 nm). In the case of the thin film, an absorption peak was observed at around 383 nm, and emission wavelength peaks were 425 nm and 441 nm (at an excitation wavelength of 381 nm).

Further, electrochemical characteristics of a thin film of mPnPDBq were measured (the measuring instrument was AC-2 produced by Riken Keiki, Co., Ltd.). Note that the measurement of electrochemical characteristics of the thin film was carried out in the same manner as Example 1.

From the results of the measurement of electrochemical characteristics of the thin film, the HOMO level, the LUMO level, and the band gap (Bg) were found to be −5.90 eV, −2.79 eV, and 3.11 eV, respectively.

The above results reveal that mPnPDBq has a relatively deep HOMO level, a relatively shallow LUMO level, and a relatively wide Bg.

Electrochemical characteristics of an mPnPDBq solution were also measured.

As a measuring method, cyclic voltammetry (CV) measurement was employed. An electrochemical analyzer (ALS model 600A or 600C, produced by BAS Inc.) was used for the measurement.

The value of the HOMO level was found to be −6.20 eV, indicating that mPnPDBq can efficiently inject holes into a material having a HOMO level whose value is close to this value. Further, since the HOMO level is deep (the value thereof is small), it is found that mPnPDBq can efficiently inject holes into a material having a shallower HOMO level (a smaller value) than mPnPDBq.

The value of the LUMO level was found to be −2.95 eV, indicating that mPnPDBq can efficiently inject electrons into a material having a LUMO level whose value is close to this value. Further, since the LUMO level is shallow (the value thereof is large), it is found that mPnPDBq can efficiently inject electrons into a material having a deeper LUMO level (a smaller value) than mPnPDBq. In addition, the reduction peak was at a similar value even after 100 cycles. This indicates that mPnPDBq has properties effective against repetition of redox reactions between a reduced state and a neutral state.

Note that the CV measurement was carried out in the same manner as Example 1.

Figure 45A:
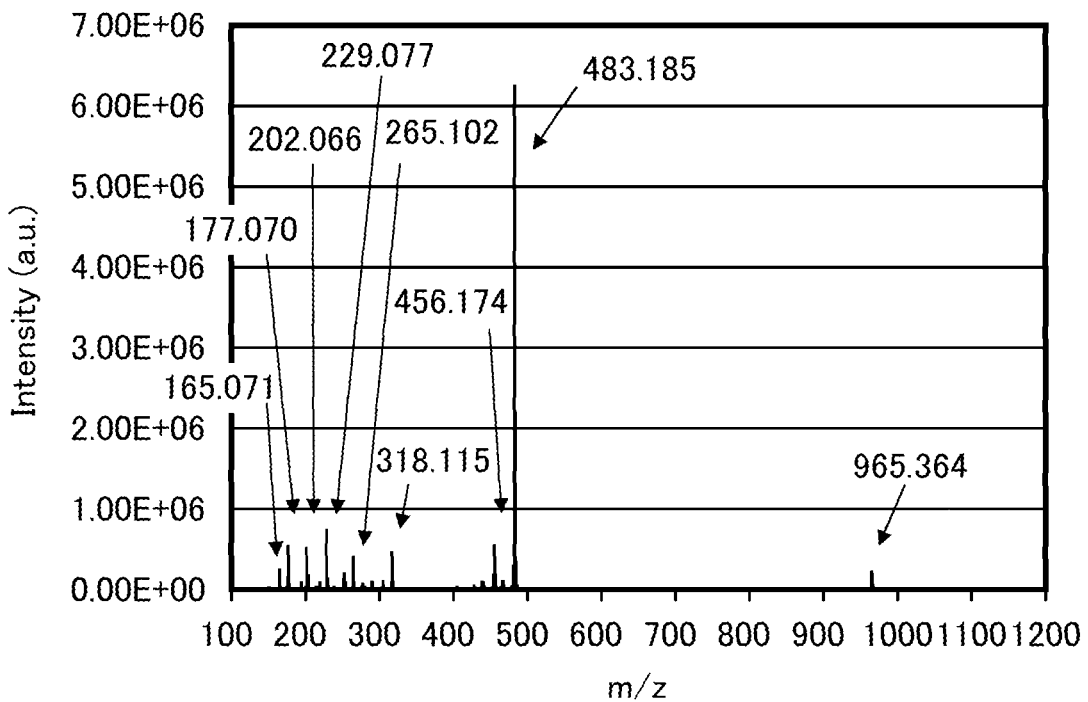
FIGS. 45A and 45B show results of LC/MS analysis of mPnPDBq.
Figure 45B:
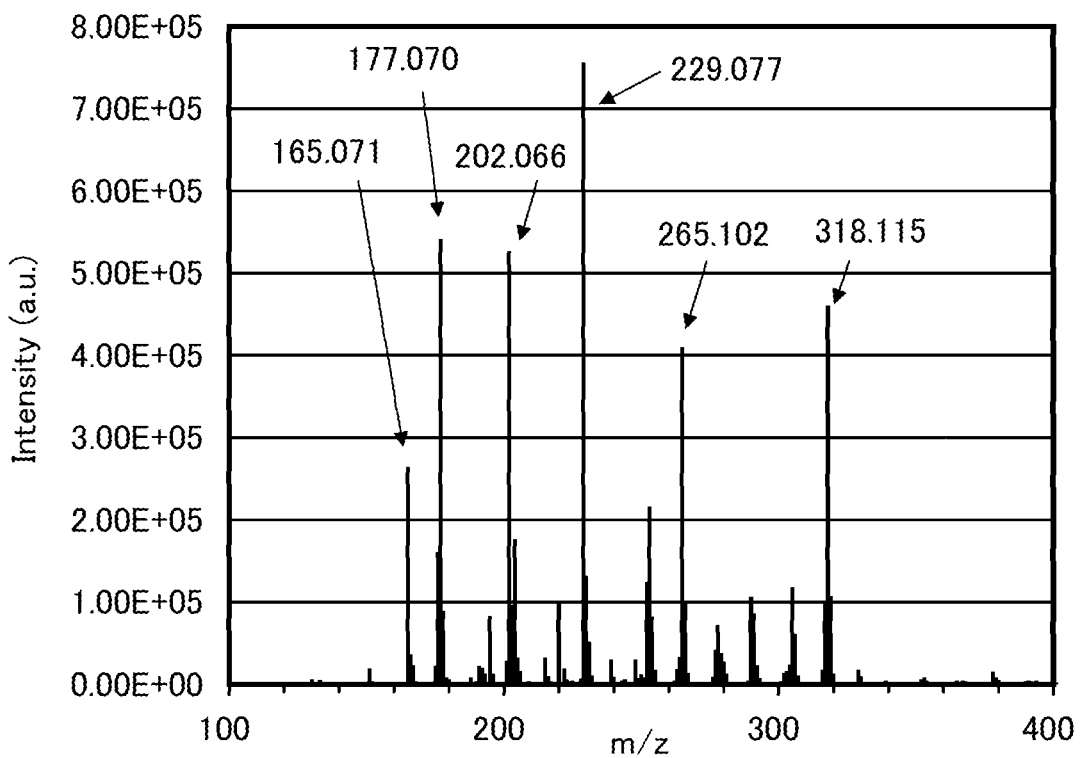

Next, mPnPDBq obtained in this example was analyzed by LC/MS. Methods, conditions, and the like for the analysis by LC/MS were the same as those in Example 1. FIGS. 45A and 45B show the results of the analysis.

The results in FIGS. 45A and 45B show that, owing to the presence and absence of hydrogen ions and isotopes, a plurality of peaks derived from product ions of mPnPDBq are detected mainly around m/z 456, m/z 229, m/z 202, m/z 177, and m/z 165. The results in FIGS. 45A and 45B are characteristically derived from mPnPDBq and thus can be regarded as important data in identification of mPnPDBq contained in a mixture.

Peaks around m/z 456 are presumed to be derived from product ions of cations in the state where one C atom and one N atom are dissociated from the dibenzo[f,h]quinoxaline ring in mPnPDBq. This is one of features of the heterocyclic compound according to one embodiment of the present invention. In particular, this is one of features of the heterocyclic compound according to one embodiment of the present invention in which a substituent(s) (in mPnPDBq, a phenylene group and a naphthalene skeleton) is bonded to the 2-position of the dibenzo[f,h]quinoxaline ring.

Peaks around m/z 229 are presumed to be product ions of cations of a diazatriphenylenyl group such as a dibenzo[f,h]quinoxaline ring. Peaks around m/z 202, m/z 177, and m/z 165 are also detected, indicating that mPnPDBq, which is the heterocyclic compound according to one embodiment of the present invention, includes a dibenzo[f,h]quinoxaline ring.

Measurement of mPnPDBq with a TOF-SIMS was further performed, and FIGS. 46A and 46B and FIGS. 47A and 47B show the qualitative spectra (positive and negative ions).

Note that FIGS. 46A and 46B each show measurement results of positive ions. In FIG. 46A, the horizontal axis represents m/z in the range of 0 to 500, and the vertical axis represents intensity (arbitrary unit). In FIG. 46B, the horizontal axis represents m/z in the range of 400 to 1200, and the vertical axis represents intensity (arbitrary unit). Further, FIGS. 47A and 47B each show measurement results of negative ions. In FIG. 47A, the horizontal axis represents m/z in the range of 0 to 400, and the vertical axis represents intensity (arbitrary unit). In FIG. 47B, the horizontal axis represents m/z in the range of 400 to 1200, and the vertical axis represents intensity (arbitrary unit).

TOF.SIMS 5 (manufactured by ION-TOF GmbH) was used, where $Bi_3^{++}$ was used as a primary ion source. Note that irradiation with the primary ions was performed in a pulsed manner with a pulse width of 7 nm to 12 nm. The irradiation amount was greater than or equal to $8.2 E10$ ions/cm$^2$ and less than or equal to $6.7 E11$ ions/cm$^2$ (less than or equal to $1 E12$ ions/cm$^2$), acceleration voltage was 25 eV, and a current value was 0.2 pA. A powder of mPnPDBq was the sample used for the measurement.

The results in FIGS. 46A and 46B reveal that, owing to the presence and absence of hydrogen ions and isotopes, a plurality of peaks derived from precursor ions of mPnPDBq are detected mainly around m/z 483. Owing to the presence and absence of hydrogen ions and isotopes, a plurality of peaks derived from product ions around m/z 229, m/z 202, m/z 176, and m/z 165 are also detected, indicating that mPnPDBq includes a dibenzo[f,h]quinoxaline ring. Note that the measurement results with a TOF-SIMS can be similarly regarded as important data in identification of mPnPDBq contained in a mixture.

The results in FIGS. 47A and 47B reveal that, owing to the presence and absence of hydrogen ions and isotopes, mPnPDBq mainly has a plurality of peaks derived from product ions around m/z 469 and peaks derived from precursor ions around m/z 483. The results in FIGS. 47A and 47B are characteristically derived from mPnPDBq and thus can be regarded as important data in identification of mPnPDBq contained in a mixture.

Peaks around m/z 469 are presumed to be derived from product ions of radical cations in the state where one N atom is removed from the dibenzo[f,h]quinoxaline ring in mPnPDBq. This is one of features of the heterocyclic compound according to one embodiment of the present invention. In particular, this is one of features of the heterocyclic compound according to one embodiment of the present invention in which a substituent(s) (in mPnPDBq, a phenylene group and a naphthalene skeleton) is bonded to the 2-position of the dibenzo[f,h]quinoxaline ring.

EXAMPLE 3

SYNTHESIS EXAMPLE 3

Example 3 shows a method of synthesizing 2-[4-(phenanthren-9-yl)phenyl]dibenzo[f,h]quinoxaline (abbreviation: DBqPPn) represented by the following structural formula (105), which is the heterocyclic compound according to one embodiment of the present invention. Example 3 also shows methods of synthesizing 9-(4-bromophenyl)phenanthrene (abbreviation: PnPBr) represented by the following structural formula (900) and 4-(phenanthren-9-yl)phenylboronic acid represented by the following structural formula (901), which are heterocyclic compounds according to embodiments of the present invention.

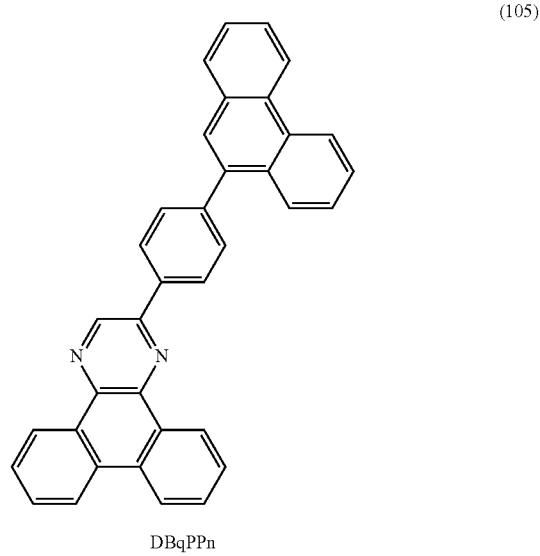

(105)

DBqPPn

-continued

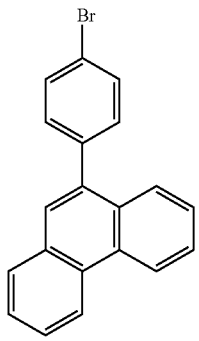

PnPBr                                    (900)

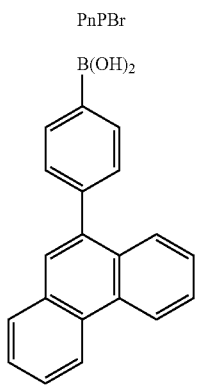

PnPBr                                    (901)

Step 1: Synthesis of 9-(4-bromophenyl)phenanthrene (abbreviation: PnPBr)

A synthesis scheme of Step 1 is illustrated in (E-1).

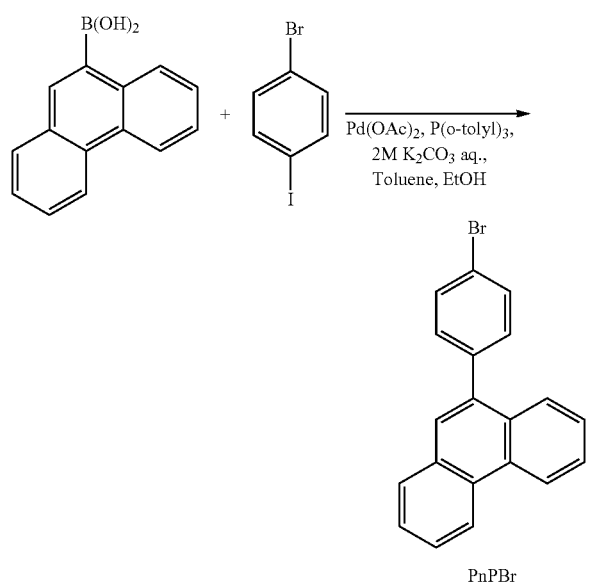

(E-1)

In a 200 mL three-neck flask, a mixture of 7.7 g (27 mmol) of 1-bromo-4-iodobenzene, 5.0 g (23 mmol) of 9-phenanthrene boronic acid, 61 mg (0.3 mmol) of palladium acetate, 247 mg (0.8 mmol) of tri(ortho-tolyl)phosphine, 100 mL of toluene, 10 mL of ethanol, and 35 mL of an aqueous solution of potassium carbonate (2 mol/L) was degassed while being stirred under reduced pressure, and reacted while being heated and stirred under a nitrogen atmosphere at 80° C. for 9 hours.

After the reaction, 500 mL of toluene was added to this reaction mixture solution, and an organic layer of the mixture solution was filtered through Florisil (produced by Wako Pure Chemical Industries, Ltd., catalog No. 540-00135), alumina (produced by Merck & Co., Inc., neutral), and Celite (produced by Wako Pure Chemical Industries, Ltd., catalog No. 531-16855). The obtained filtrate was washed with water, and magnesium sulfate was added thereto so that moisture was adsorbed. This suspension was filtered to obtain a filtrate. The obtained filtrate was concentrated and purified by silica gel column chromatography. At this time, a mixed solvent of toluene and hexane in a ratio of 1:5 was used as a developing solvent for the chromatography. The obtained fraction was concentrated, and then recrystallized with toluene and hexane, so that the objective substance was obtained as 5.0 g of white powder in a yield of 66%.

A nuclear magnetic resonance (NMR) method identified this compound as 9-(4-bromophenyl)phenanthrene (abbreviation: PnPBr).

$^1$H NMR data of the obtained substance are as follows: $^1$H NMR (CDCl$_3$, 300 MHz): δ (ppm)=7.42 (d, J=8.3 Hz, 2H), 7.49-7.71 (m, 7H), 7.84-7.91 (m, 2H), 8.73 (d, J=7.8 Hz, 1H), 8.78 (d, J=8.3 Hz, 1H).

Step 2: Synthesis of 4-(phenanthren-9-yl)phenylboronic acid

A synthesis scheme of Step 2 is illustrated in (E-2).

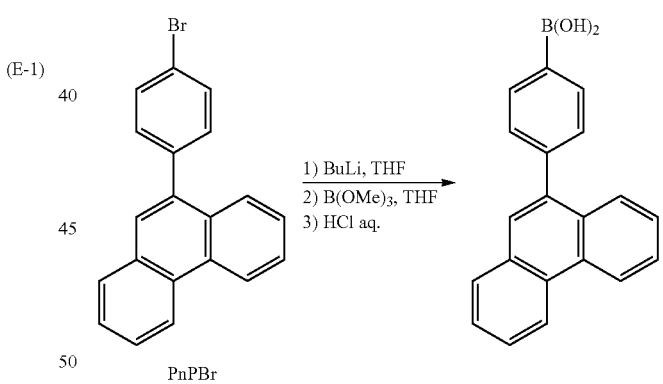

(E-2)

Into a 100 mL three-neck flask, 2.0 g (11 mmol) of PnPBr obtained in the above Step 1 was put, and the air in the flask was replaced with nitrogen. Into the flask, 35 mL of tetrahydrofuran (THF) was added, and then this solution was stirred at −80° C. Into this solution, 8.3 mL (14 mmol) of n-butyllithium (1.6 mol/L hexane solution) was dropped by a syringe. After the dropping, this solution was stirred at the same temperature for 2 hours. After the stirring, 1.3 mL (11 mmol) of trimethyl borate was added to this solution, and the solution was stirred for 18 hours while the temperature of the solution was being increased to room temperature. Into this solution, hydrochloric acid (1.0 mol/L) was added, and then the solution was stirred for one hour. The organic layer was washed with a saturated aqueous solution of sodium hydrogen carbonate and then with saturated saline, and magnesium sulfate was added to the organic layer so that moisture was adsorbed. The mixture was gravity-filtered, and the obtained filtrate was concentrated to give the objective white solid. This solid was recrystallized with ethyl acetate and hexane to give the objective substance as 2.5 g of white powdered solid in a yield of 74%.

Step 3: Synthesis of 2-[4-(phenanthren-9-yl)phenyl] dibenzo[f,h]quinoxaline (abbreviation: DBqPPn)

A synthesis scheme of Step 3 is illustrated in (E-3).

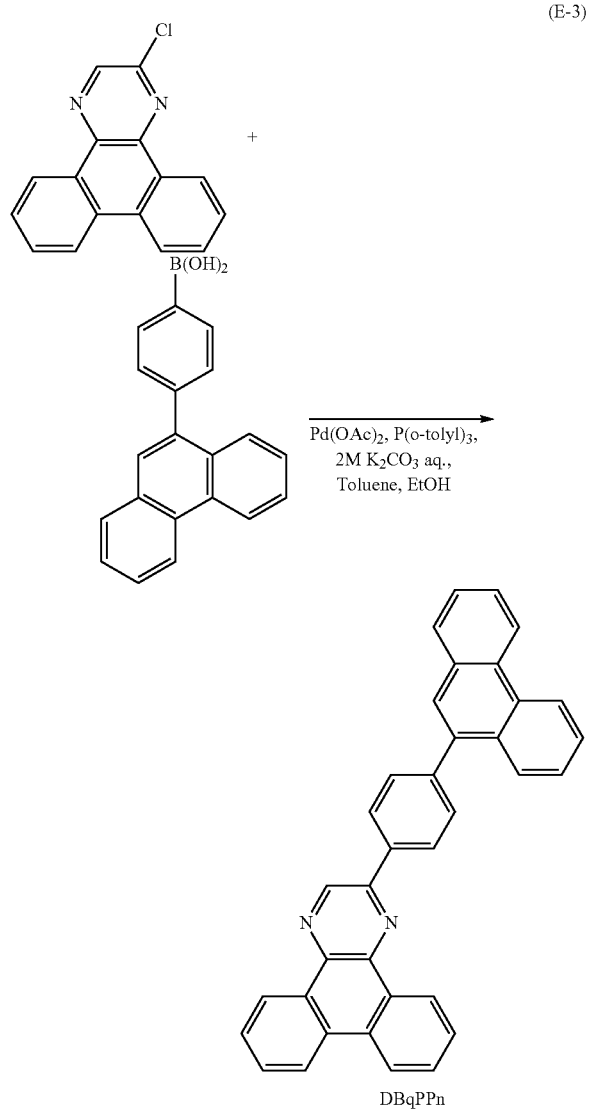

DBqPPn

In a 200 mL three-neck flask, a mixture of 2.0 g (7.6 mmol) of 2-chlorodibenzo[f,h]quinoxaline, 2.5 g (8.4 mmol) of 4-(phenanthren-9-yl)phenylboronic acid obtained in the above Step 2, 18 mg (0.1 mmol) of palladium(II) acetate, 73 mg (0.2 mmol) of tri(ortho-tolyl)phosphine, 30 mL of toluene, 3 mL of ethanol, and 10 mL of an aqueous solution of potassium carbonate (2 mol/L) was degassed while being stirred under reduced pressure, and was then reacted by being heated and stirred under a nitrogen atmosphere at 80° C. for 10.5 hours.

After the reaction, 500 mL of toluene was added to this reaction mixture solution, and an organic layer of the mixture solution was filtered through Florisil (produced by Wako Pure Chemical Industries, Ltd., catalog No. 540-00135), alumina (produced by Merck & Co., Inc., neutral), and Celite (produced by Wako Pure Chemical Industries, Ltd., catalog No. 531-16855). The obtained filtrate was washed with water, and magnesium sulfate was added thereto so that moisture was adsorbed. This suspension was filtered to obtain a filtrate. The obtained filtrate was concentrated and purified by silica gel column chromatography. At this time, a mixed solvent of toluene and hexane in a ratio of 3:5 was used as a developing solvent for the chromatography. The obtained fraction was concentrated, and then recrystallized with toluene, so that the objective substance was obtained as 1.6 g of white powder in a yield of 44%.

The Rf values of the objective substance and 2-chlorodibenzo[f,h]quinoxaline were respectively 0.20 and 0.55, which were found by silica gel thin layer chromatography (TLC) (with a developing solvent of ethyl acetate and hexane in a ratio of 1:10).

A nuclear magnetic resonance (NMR) method identified this compound as 2-[4-(phenanthren-9-yl)phenyl]dibenzo[f,h]quinoxaline (abbreviation: DBqPPn), which was the objective substance.

$^1$H NMR data of the obtained substance are as follows: $^1$H NMR (CDCl$_3$, 300 MHz): δ (ppm)=7.60-7.85 (m, 11H), 7.96 (d, J=7.3 Hz, 1H), 8.04 (d, J=7.3 Hz, 1H), 8.53 (d, J=8.8 Hz, 2H), 8.69 (d, J=8.3 Hz, 2H), 8.77 (d, J=7.8 Hz, 1H), 8.83 (d, J=6.8 Hz, 1H), 9.28 (d, J=8.3 Hz, 1H), 9.48-9.52 (m, 2H).

Figure 16A:
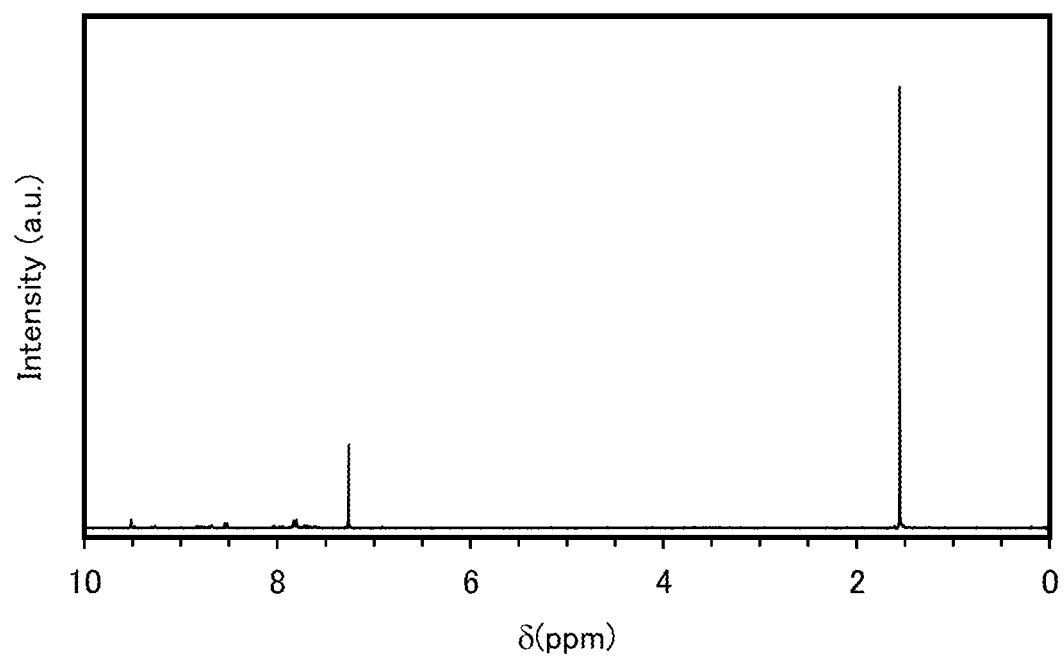
FIGS. 16A and 16B show $^1$H NMR charts of 2-[4-(phenanthren-9-yl)phenyl]dibenzo[f,h]quinoxaline (abbreviation: DBqPPn).
Figure 16B:
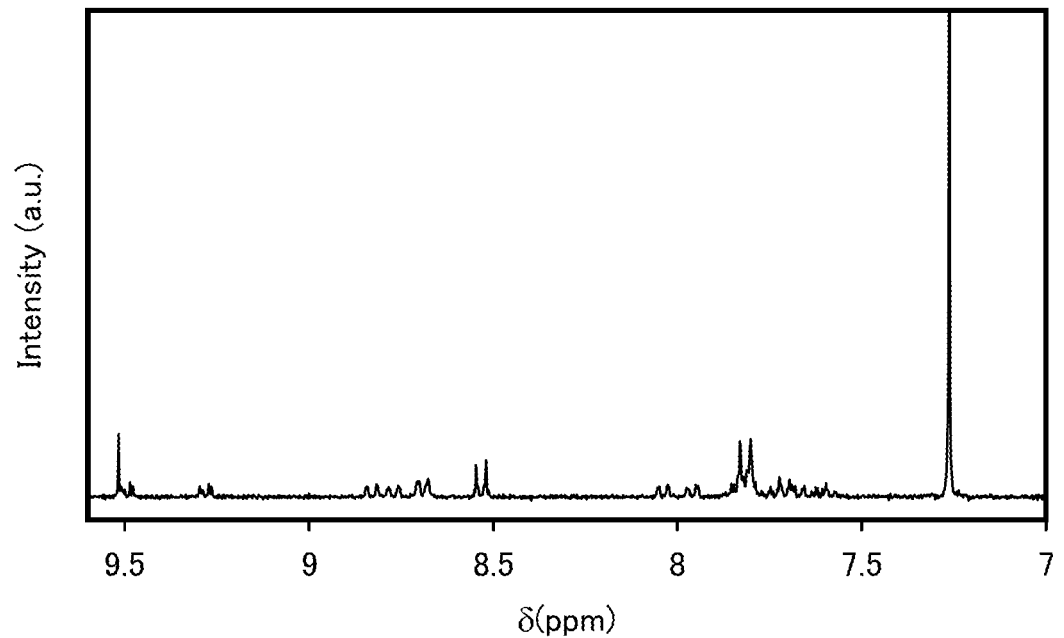

The $^1$H NMR chart is shown in FIGS. 16A and 16B. Note that FIG. 16B is a chart showing an enlarged part of FIG. 16A in the range of 7.00 ppm to 9.60 ppm.

Figure 17A:
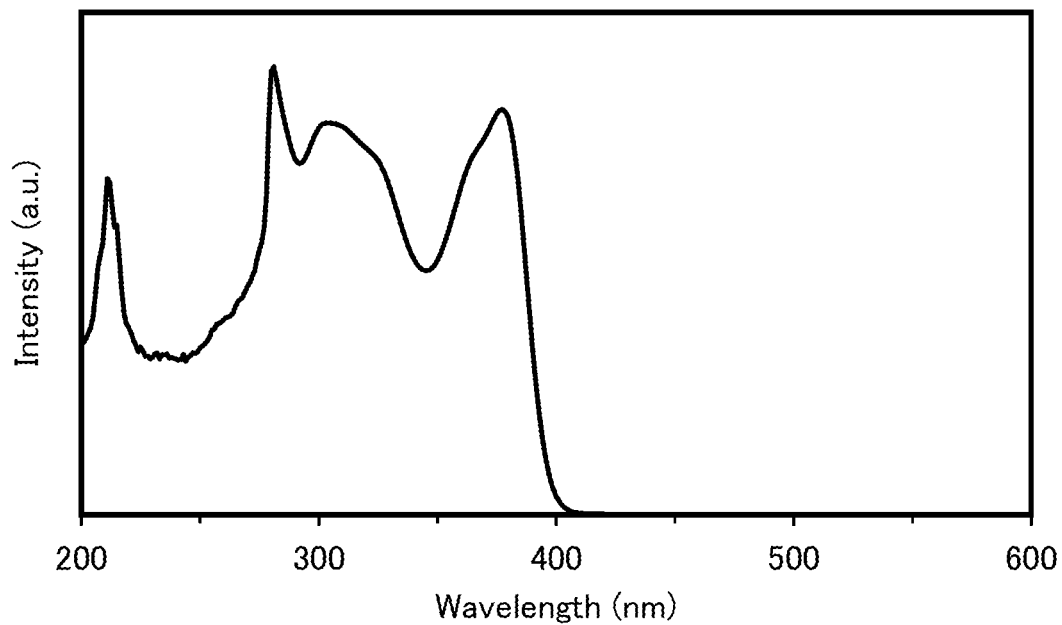
FIGS. 17A and 17B show an absorption spectrum and an emission spectrum of a toluene solution of DBqPPn.
Figure 17B:
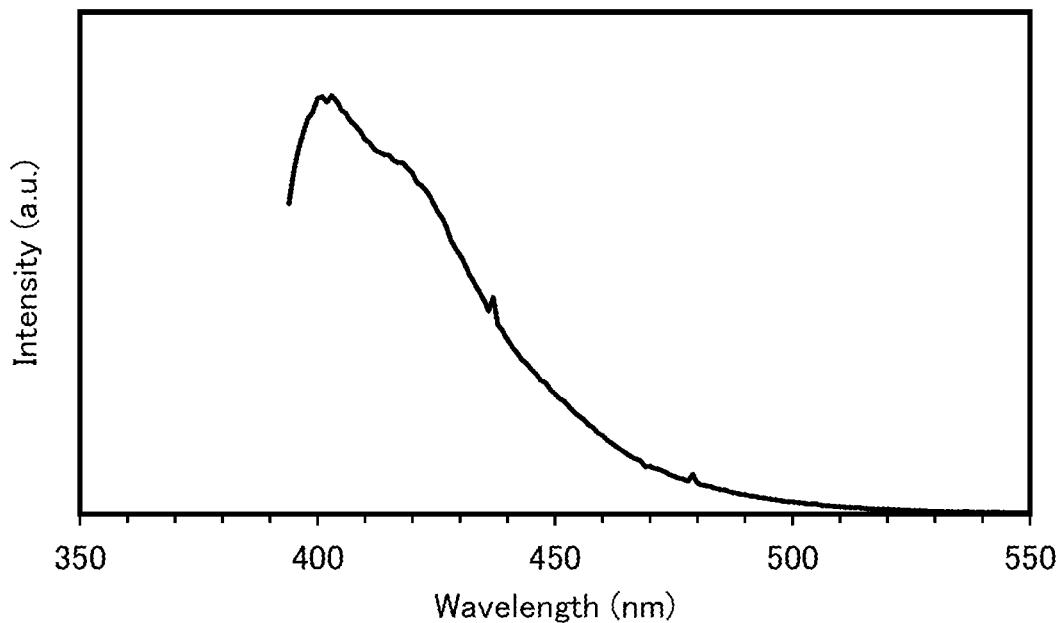
Figure 18A:
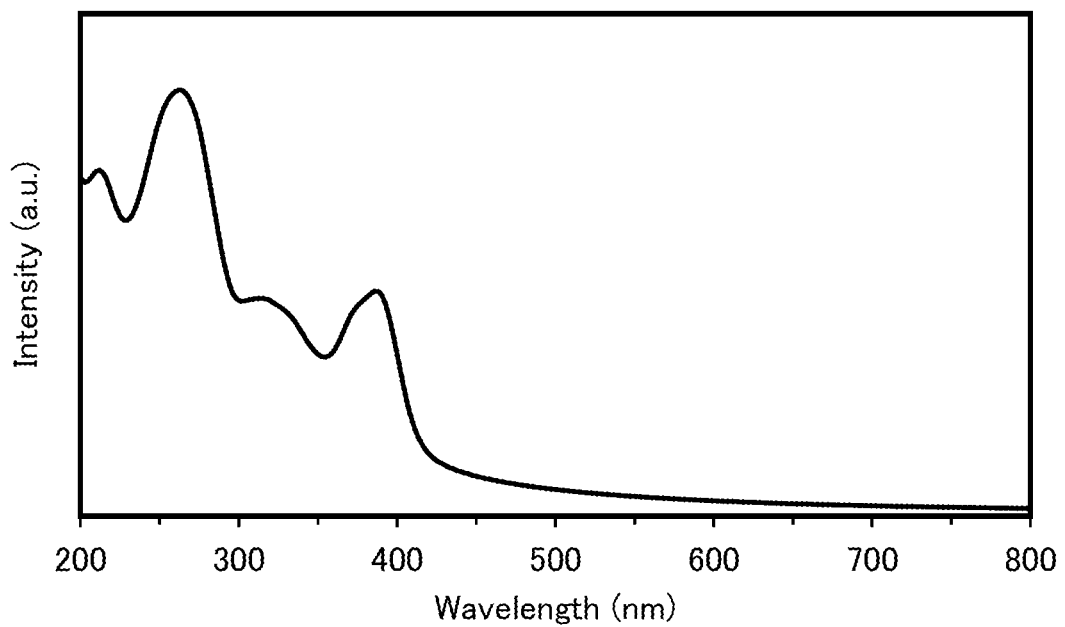
FIGS. 18A and 18B show an absorption spectrum and an emission spectrum of a thin film of DBqPPn.
Figure 18B:
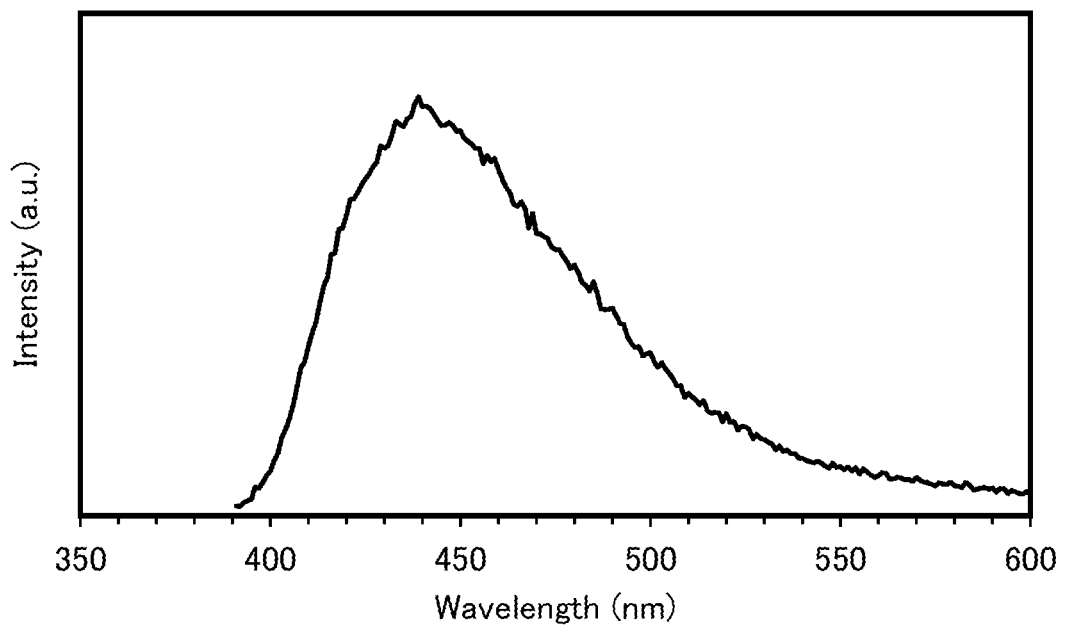

Further, FIG. 17A shows an absorption spectrum of a toluene solution of DBqPPn, and FIG. 17B shows an emission spectrum thereof. FIG. 18A shows an absorption spectrum of a thin film of DBqPPn, and FIG. 18B shows an emission spectrum thereof. The absorption spectra were obtained in the same manner as Example 1. In FIGS. 17A and 17B and FIGS. 18A and 18B, the horizontal axis represents wavelength (nm) and the vertical axis represents intensity (arbitrary unit). In the case of the toluene solution, an absorption peak was observed at around 375 nm, and an emission wavelength peak was 404 nm (at an excitation wavelength of 337 nm). In the case of the thin film, an absorption peak was observed at around 387 nm, and an emission wavelength peak was at 439 nm (at an excitation wavelength of 387 nm).

Further, electrochemical characteristics of a thin film of DBqPPn were measured (the measuring instrument was AC-2 produced by Riken Keiki, Co., Ltd.). Note that the measurement of electrochemical characteristics of the thin film was carried out in the same manner as Example 1.

From the results of the measurement of electrochemical characteristics of the thin film, the HOMO level, the LUMO level, and the band gap (Bg) were found to be −5.91 eV, −2.88 eV, and 3.03 eV, respectively.

The above results reveal that DBqPPn has a relatively deep HOMO level, a relatively shallow LUMO level, and a relatively wide Bg.

Electrochemical characteristics of a DBqPPn solution were also measured.

As a measuring method, cyclic voltammetry (CV) measurement was employed. An electrochemical analyzer (ALS model 600A or 600C, produced by BAS Inc.) was used for the measurement.

The value of the HOMO level was found to be −6.15 eV, indicating that DBqPPn can efficiently inject holes into a material having a HOMO level whose value is close to this value. Further, since the HOMO level is deep (the value thereof is small), it is found that DBqPPn can efficiently inject holes into a material having a shallower HOMO level (a smaller value) than DBqPPn.

The value of the LUMO level was found to be −2.95 eV, indicating that DBqPPn can efficiently inject electrons into a material having a LUMO level whose value is close to this value. Further, since the LUMO level is shallow (the value thereof is large), it is found that DBqPPn can efficiently inject electrons into a material having a deeper LUMO level (a smaller value) than DBqPPn. In addition, the reduction peak was at a similar value even after 100 cycles. This indicates that DBqPPn has properties effective against repetition of redox reactions between a reduced state and a neutral state.

Note that the CV measurement was carried out in the same manner as Example 1.

Figure 48A:
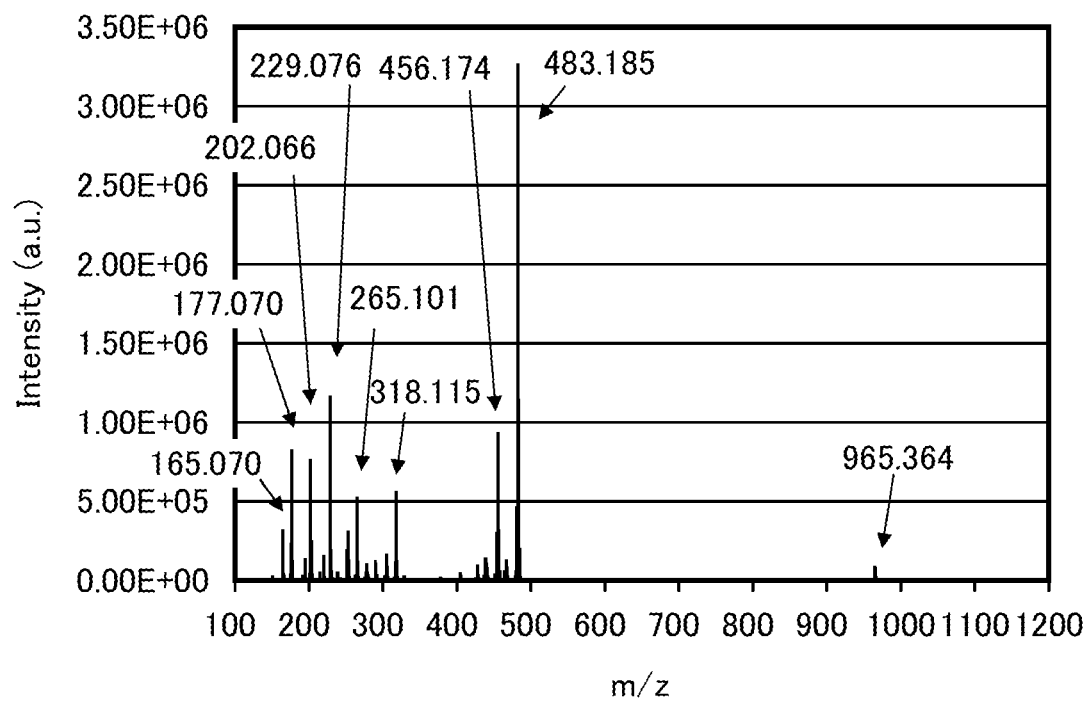
FIGS. 48A and 48B show results of LC/MS analysis of DBqPPn.
Figure 48B:
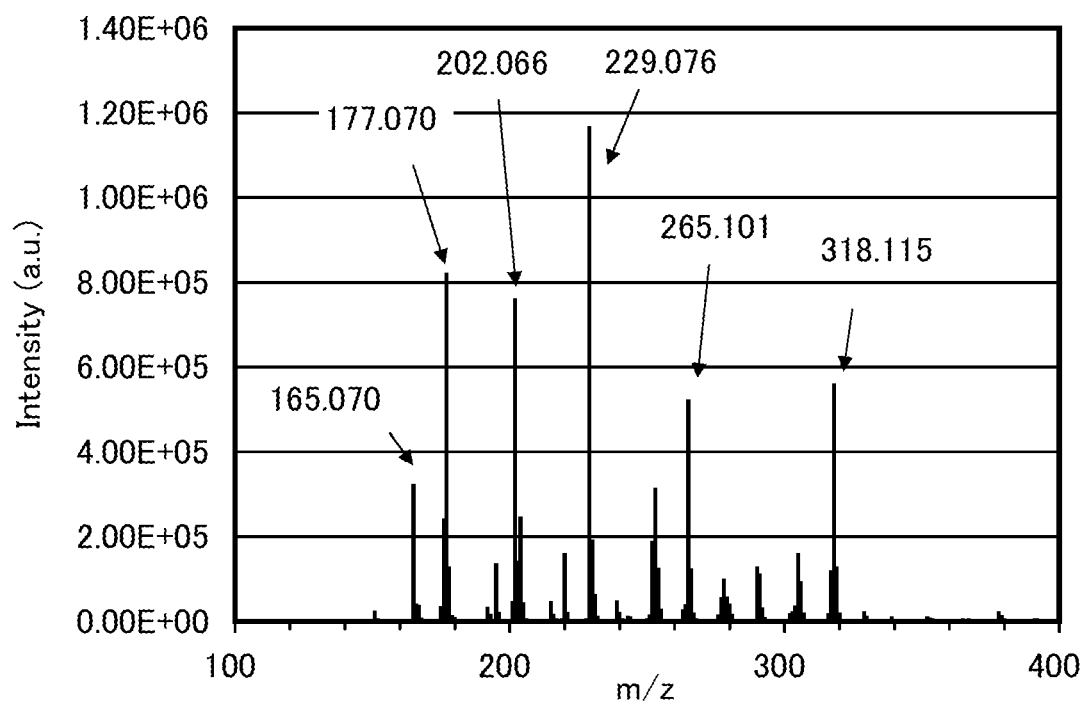

Next, DBqPPn obtained in this example was analyzed by LC/MS. Methods, conditions, and the like for the analysis by LC/MS were the same as those in Example 1. FIGS. 48A and 48B show the results of the analysis.

The results in FIGS. 48A and 48B show that, owing to the presence and absence of hydrogen ions and isotopes, a plurality of peaks derived from product ions of DBqPPn are detected mainly around m/z 456, m/z 229, m/z 202, m/z 177, and m/z 165. The results in FIGS. 48A and 48B are characteristically derived from DBqPPn and thus can be regarded as important data in identification of DBqPPn contained in a mixture.

Peaks around m/z 456 are presumed to be derived from product ions of cations in the state where one C atom and one N atom are dissociated from the dibenzo[f,h]quinoxaline ring in DBqPPn. This is one of features of the heterocyclic compound according to one embodiment of the present invention. In particular, this is one of features of the heterocyclic compound according to one embodiment of the present invention in which a substituent(s) (in DBqPPn, a phenylene group and a naphthalene skeleton) is bonded to the 2-position of the dibenzo[f,h]quinoxaline ring.

Peaks around m/z 229 are presumed to be derived from product ions of cations of a diazatriphenylenyl group such as a dibenzo[f,h]quinoxaline ring. Peaks around m/z 202, m/z 177, and m/z 165 are also detected, indicating that DBqPPn, which is the heterocyclic compound according to one embodiment of the present invention, includes a dibenzo[f,h] quinoxaline ring.

Measurement of DBqPPn with a TOF-SIMS was further performed, and FIGS. 49A and 49B and FIGS. 50A and 50B show the qualitative spectra (positive and negative ions).

Note that FIGS. 49A and 49B each show measurement results of positive ions. In FIG. 49A, the horizontal axis represents m/z in the range of 0 to 500, and the vertical axis represents intensity (arbitrary unit). In FIG. 49B, the horizontal axis represents m/z in the range of 400 to 1200, and the vertical axis represents intensity (arbitrary unit). Further, FIGS. 50A and 50B each show measurement results of negative ions. In FIG. 50A, the horizontal axis represents m/z in the range of 0 to 400, and the vertical axis represents intensity (arbitrary unit). In FIG. 50B, the horizontal axis represents m/z in the range of 400 to 1200, and the vertical axis represents intensity (arbitrary unit).

TOF.SIMS 5 (manufactured by ION-TOF GmbH) was used, where $Bi_3^{++}$ was used as a primary ion source. Note that irradiation with the primary ions was performed in a pulsed manner with a pulse width of 7 nm to 12 nm. The irradiation amount was greater than or equal to $8.2\ E10$ ions/cm$^2$ and less than or equal to $6.7\ E11$ ions/cm$^2$ (less than or equal to $1\ E12$ ions/cm$^2$), acceleration voltage was 25 eV, and a current value was 0.2 pA. A powder of DBqPPn was the sample used for the measurement.

The results in FIGS. 49A and 49B reveal that, owing to the presence and absence of hydrogen ions and isotopes, a plurality of peaks derived from precursor ions of DBqPPn are detected mainly around m/z 483. Owing to the presence and absence of hydrogen ions and isotopes, a plurality of peaks derived from product ions around m/z 229, m/z 201, m/z 176, and m/z 165 are also detected, indicating that DBqPPn includes a dibenzo[f,h]quinoxaline ring. Note that the measurement results with a TOF-SIMS can be similarly regarded as important data in identification of DBqPPn contained in a mixture.

The results in FIGS. 50A and 50B reveal that, owing to the presence and absence of hydrogen ions and isotopes, DBqPPn mainly has a plurality of peaks derived from product ions around m/z 469 and peaks derived from precursor ions around m/z 483. The results in FIGS. 50A and 50B are characteristically derived from DBqPPn and thus can be regarded as important data in identification of DBqPPn contained in a mixture.

Peaks around m/z 469 are presumed to be derived from product ions of radical cations in the state where one N atom is removed from the dibenzo[f,h]quinoxaline ring in DBqPPn. This is one of features of the heterocyclic compound according to one embodiment of the present invention. In particular, this is one of features of the heterocyclic compound according to one embodiment of the present invention in which a substituent(s) (in DBqPPn, a phenylene group and a naphthalene skeleton) is bonded to the 2-position of the dibenzo[f,h]quinoxaline ring.

EXAMPLE 4

Figure 19:
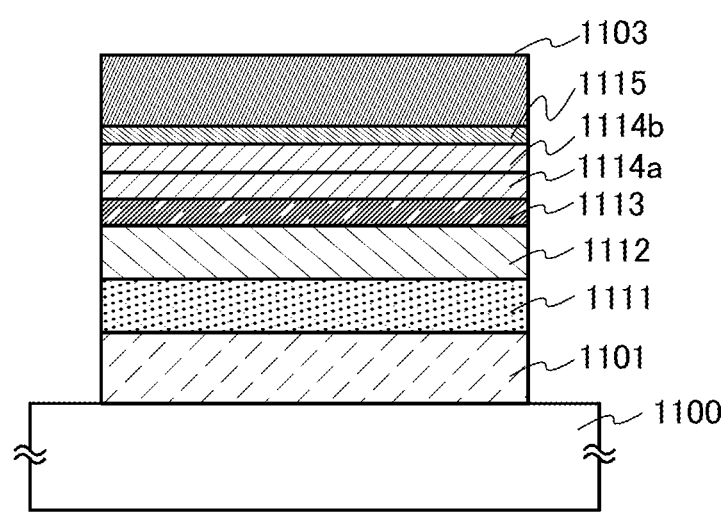
FIG. 19 illustrates a light-emitting element of Examples.

In this example, a light-emitting element according to one embodiment of the present invention is described with reference to FIG. 19. Chemical formulas of materials used in this example are shown below. Note that the chemical formulas of the materials which are described above are omitted.

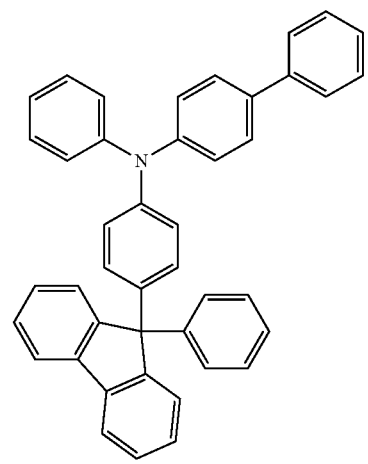

BPAFLP

-continued

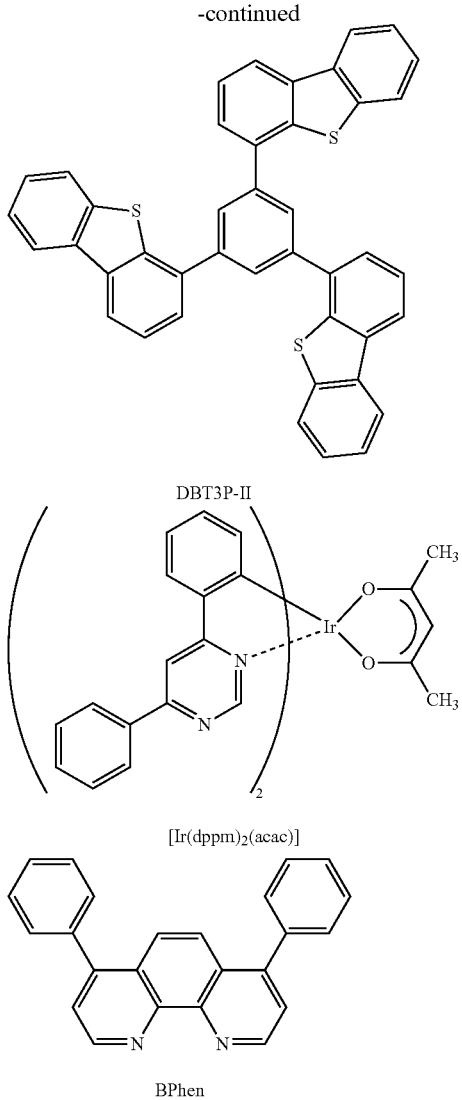

DBT3P-II

[Ir(dppm)₂(acac)]

BPhen

The following shows methods of fabricating light-emitting elements 1 and 2 of this example.
(Light-Emitting Element 1)

First, indium tin oxide containing silicon oxide (ITSO) was deposited by a sputtering method on a glass substrate 1100, whereby a first electrode 1101 was formed. The thickness was 110 nm and the electrode area was 2 mm×2 mm. Here, the first electrode 1101 functions as an anode of the light-emitting element.

Next, as pretreatment for forming the light-emitting element over the substrate 1100, the surface of the substrate was washed with water, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Then, the substrate 1100 over which the first electrode 1101 was formed was fixed to a substrate holder provided in the vacuum evaporation apparatus such that the surface on which the first electrode 1101 was formed faced downward.

The pressure in the vacuum evaporation apparatus was reduced to about $10^{-4}$ Pa. After that, over the first electrode 1101, 4,4',4''-(1,3,5-benzenetriyl)tri(dibenzothiophene) (abbreviation: DBT3P-II) and molybdenum(VI) oxide were co-evaporated by an evaporation method using resistance heating, so that a hole-injection layer 1111 was formed. The thickness of the hole-injection layer 1111 was set to 40 nm, and the weight ratio of DBT3P-II to molybdenum oxide was adjusted to 4:2 (=DBT3P-II:molybdenum oxide). Note that the co-evaporation method refers to an evaporation method in which evaporation is carried out from a plurality of evaporation sources at the same time in one treatment chamber.

Next, 4-phenyl-4'-(9-phenylfluoren-9-yl)triphenylamine (abbreviation: BPAFLP) was deposited to a thickness of 20 nm on the hole-injection layer 1111, whereby a hole-transport layer 1112 was formed.

Further, 2-[4-(naphthalen-1-yl)phenyl]dibenzo[f,h]quinoxaline (abbreviation: NPDBq) synthesized in Example 1, 4,4'-bis[N-(1-naphthyl)-N-phenylamino]biphenyl (abbreviation: NPB), and (acetylacetonato)bis(4,6-diphenylpyrimidinato)iridium(III) (abbreviation: [Ir(dppm)₂(acac)]) were co-evaporated, whereby a light-emitting layer 1113 was formed over the hole-transport layer 1112. Here, the weight ratio of NPDBq to NPB and [Ir(dppm)₂(acac)] was adjusted to 0.8: 0.2:0.05 (=NPDBq:NPB[Ir(dppm)₂(acac)]). The thickness of the light-emitting layer 1113 was set to 40 nm.

Further, an NPDBq film was formed to a thickness of 10 nm over the light-emitting layer 1113, whereby a first electron-transport layer 1114a was formed.

Then, a bathophenanthroline (abbreviation: BPhen) film was formed to a thickness of 20 nm over the first electron-transport layer 1114a, whereby a second electron-transport layer 1114b was formed.

Further, a lithium fluoride (LiF) film was formed to a thickness of 1 nm over the second electron-transport layer 1114b by evaporation, whereby an electron-injection layer 1115 was formed.

Lastly, an aluminum film was formed to a thickness of 200 nm by evaporation, whereby a second electrode 1103 functioning as a cathode was formed. Thus, the light-emitting element 1 of this example was fabricated.

Note that, in the above evaporation process, evaporation was all performed by a resistance heating method.

(Light-Emitting Element 2)

The light-emitting layer 1113 of the light-emitting element 2 was formed by co-evaporation of 2-[4-(phenanthren-9-yl) phenyl]dibenzo[f,h]quinoxaline (abbreviation: DBqPPn) synthesized in Example 3, NBP, and [Ir(dppm)₂(acac)]. Here, the weight ratio of DBqPPn to NPB and [Ir(dppm)₂(acac)] was adjusted to 0.8:0.2:0.05 (=DBqPPn:NPB[Ir(dppm)₂ (acac)]). The thickness of the light-emitting layer 1113 was set to 40 nm.

A DBqPPn film was formed to a thickness of 10 nm, whereby the first electron-transport layer 1114a of the light-emitting element 2 was formed. The components other than the light-emitting layer 1113 and the first electron-transport layer 1114a were formed in the same manner as those of the light-emitting element 1.

Table 1 shows element structures of the light-emitting elements 1 and 2 obtained as described above.

TABLE 1

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 1 | ITSO 110 nm | DBT3P-II:MoOx (= 4:2) 40 nm | BP AFLP 20 nm | NPDBq:NPB:[Ir(dppm)$_2$(acac)] (= 0.8:0.2:0.05) 40 nm | NPDBq 10 nm | BPhen 20 nm | LiF 1 nm | Al 200 nm |
| Light-emitting element 2 | ITSO 110 nm | DBT3P-II:MoOx (= 4:2) 40 nm | BP AFLP 20 nm | DBqPPn:NPB:[Ir(dppm)$_2$(acac)] (= 0.8:0.2:0.05) 40 nm | DBqPPn 10 nm | BPhen 20 nm | LiF 1 nm | Al 200 nm |

In a glove box containing a nitrogen atmosphere, the light-emitting elements 1 and 2 were sealed with a glass substrate so as not to be exposed to the air. Then, operation characteristics of the elements were measured. Note that the measurement was carried out at room temperature (in an atmosphere kept at 25° C.).

Figure 20:
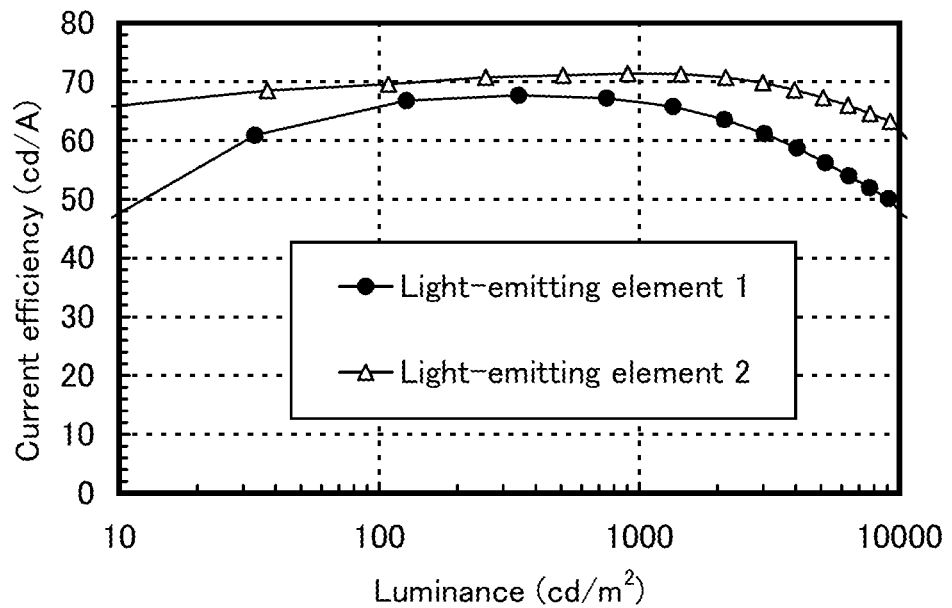
FIG. 20 shows luminance-current efficiency characteristics of light-emitting elements of Example 4.
Figure 21:
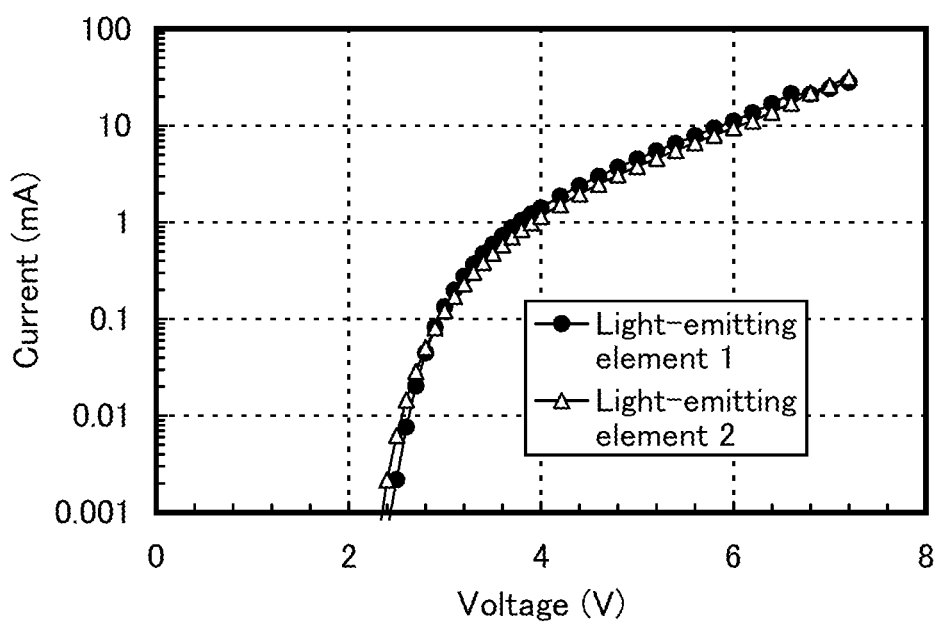
FIG. 21 shows voltage-current characteristics of the light-emitting elements of Example 4.
Figure 22:
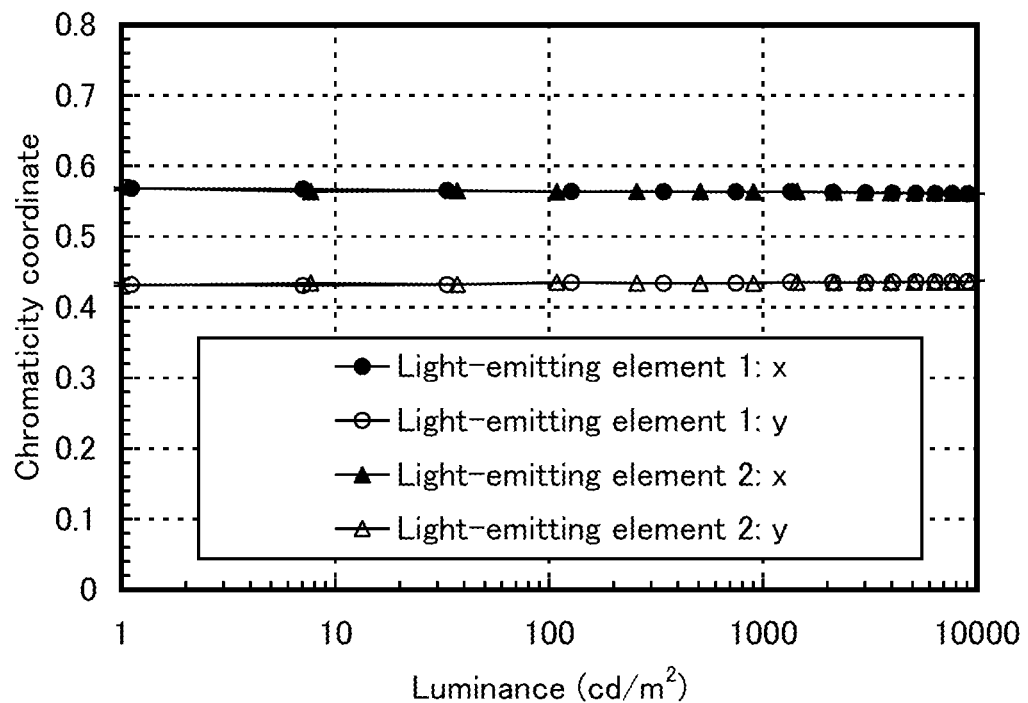
FIG. 22 shows luminance-chromaticity coordinate characteristics of the light-emitting elements of Example 4.
Figure 23:
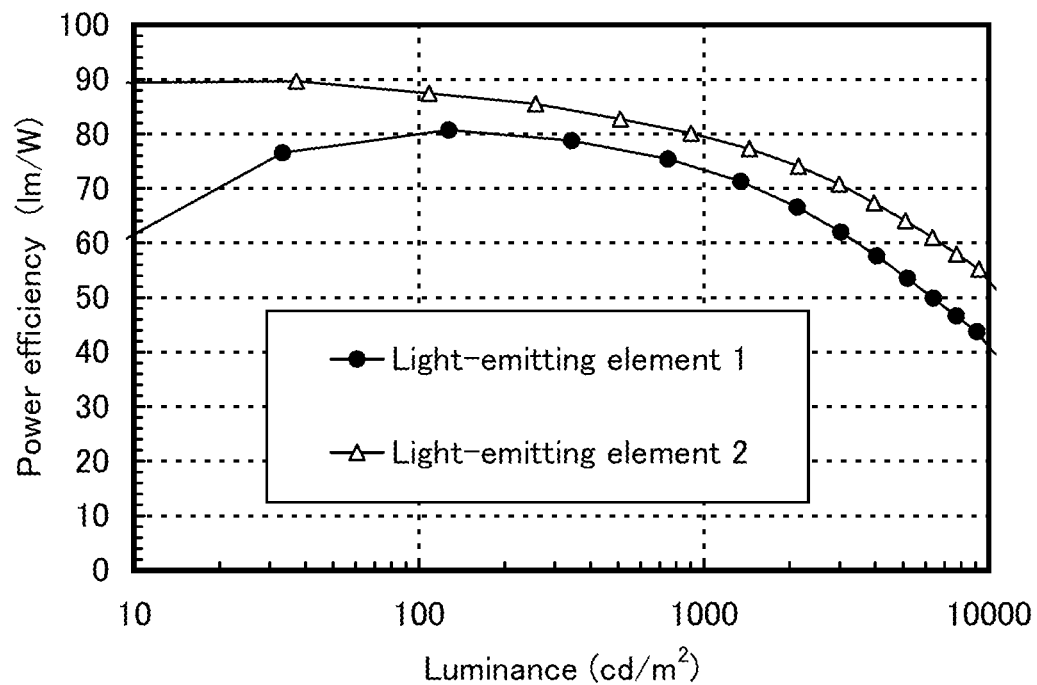
FIG. 23 shows luminance-power efficiency characteristics of the light-emitting elements of Example 4.

FIG. 20 shows luminance-current efficiency characteristics of the light-emitting elements 1 and 2. In FIG. 20, the horizontal axis represents luminance (cd/m$^2$) and the vertical axis represents current efficiency (cd/A). FIG. 21 shows voltage-current characteristics. In FIG. 21, the horizontal axis represents voltage (V) and the vertical axis represents current (mA). FIG. 22 shows the luminance-chromaticity coordinate characteristics. In FIG. 22, the horizontal axis represents luminance (cd/m$^2$) and the vertical axis represents chromaticity coordinate (the x-coordinate or the y-coordinate). FIG. 23 shows luminance-power efficiency characteristics. In FIG. 23, the horizontal axis represents luminance (cd/m$^2$) and the vertical axis represents power efficiency (lm/W). Further, Table 2 shows voltage (V), current density (mA/cm$^2$), CIE chromaticity coordinates (x, y), luminance (cd/m$^2$), current efficiency (cd/A), and external quantum efficiency (%) of each light-emitting element at a luminance of around 1000 cd/m$^2$.

element 2, respectively, NPDBq and DBqPPn, which are heterocyclic compounds according to embodiments of the present invention, are used as a host material in the light-emitting layer and as a material in the first electron-transport layer. Note that NPDBq and DBqPPn are heterocyclic compounds in which a dibenzo[f,h]quinoxaline ring and a naphthalene ring or a phenanthrene ring are bonded to each other via a para-phenylene group. Accordingly, the light-emitting elements can be driven at a low voltage.

FIG. 20, FIG. 23, and Table 2 reveal that both the light-emitting element 1 and the light-emitting element 2 have high current efficiency, high external quantum efficiency, and high power efficiency.

As shown in FIG. 22, the light-emitting elements 1 and 2 show substantially no change in color over a range from low luminance to high luminance. It can be said from this result that the light-emitting elements 1 and 2 are elements having excellent carrier balance.

One of the reasons why the light-emitting elements 1 and 2 have excellent carrier balance can be the following. In light-emitting layers of the light-emitting elements 1 and 2, NPDBq or DBqPPn with a high electron-transport property and NPB with a high hole-transport property are used. Therefore, electrons and holes can be efficiently injected into [Ir

TABLE 2

| | Voltage (V) | Current density (mA/cm$^2$) | Chromaticity (x, y) | | Luminance (cd/m$^2$) | Current efficiency (cd/A) | External quantum efficiency (%) |
|---|---|---|---|---|---|---|---|
| Light-emitting element 1 | 2.8 | 1.1 | 0.56 | 0.43 | 750 | 67 | 26 |
| Light-emitting element 2 | 2.8 | 1.3 | 0.56 | 0.43 | 900 | 71 | 29 |

Figure 24:
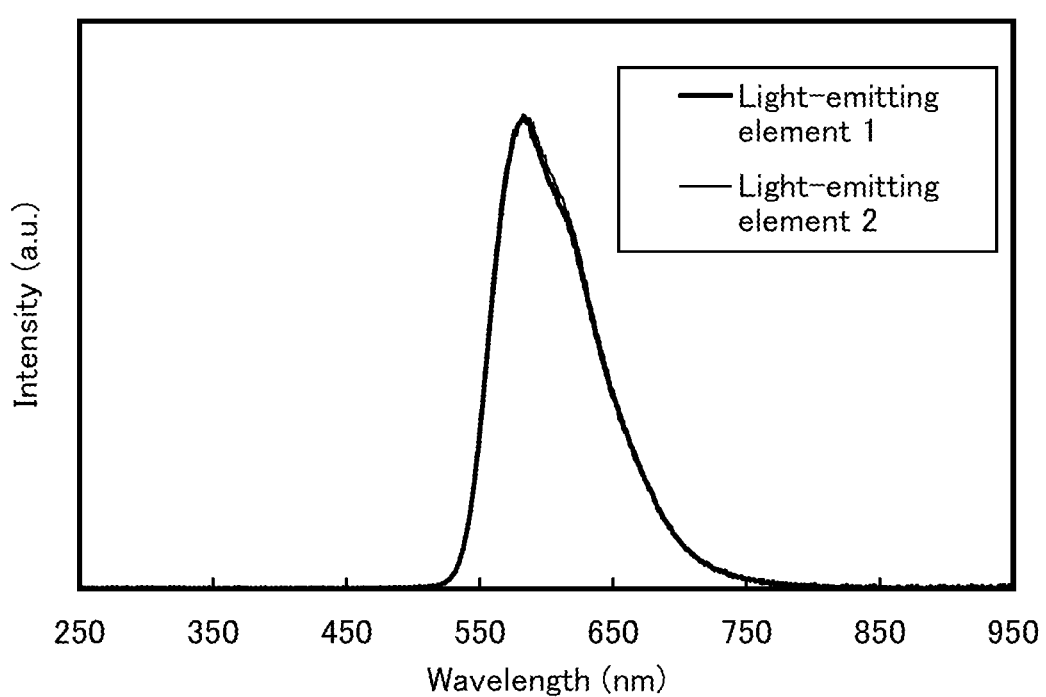
FIG. 24 shows emission spectra of the light-emitting elements of Example 4.

FIG. 24 shows emission spectra of the light-emitting elements 1 and 2, which were obtained by applying a current of 0.1 mA. In FIG. 24, the horizontal axis represents wavelength (nm) and the vertical axis represents emission intensity (arbitrary unit). As shown in FIG. 24 and Table 2, the CIE chromaticity coordinates of the light-emitting element 1 were (x, y)=(0.56, 0.43) at a luminance of 750 cd/m$^2$. In addition, the CIE chromaticity coordinates of the light-emitting element 2 were (x, y)=(0.56, 0.43) at a luminance of 900 cd/m$^2$. The light-emitting elements 1 and 2 were found to emit light originating from [Ir(dppm)$_2$(acac)]. This reveals that NPDBq and DBqPPn, which are heterocyclic compounds according to embodiments of the present invention, each have a T1 level which enables an orange phosphorescent material to emit light. Accordingly, it is found that NPDBq and DBqPPn can each be used as a host material for orange to red phosphorescent materials.

FIG. 21 and Table 2 reveal that both the light-emitting element 1 and the light-emitting element 2 are driven at a low voltage. In the light-emitting element 1 and the light-emitting (dppm)$_2$(acac)], which is the light-emitting material, so that the light-emitting elements have excellent carrier balance.

Figure 25:
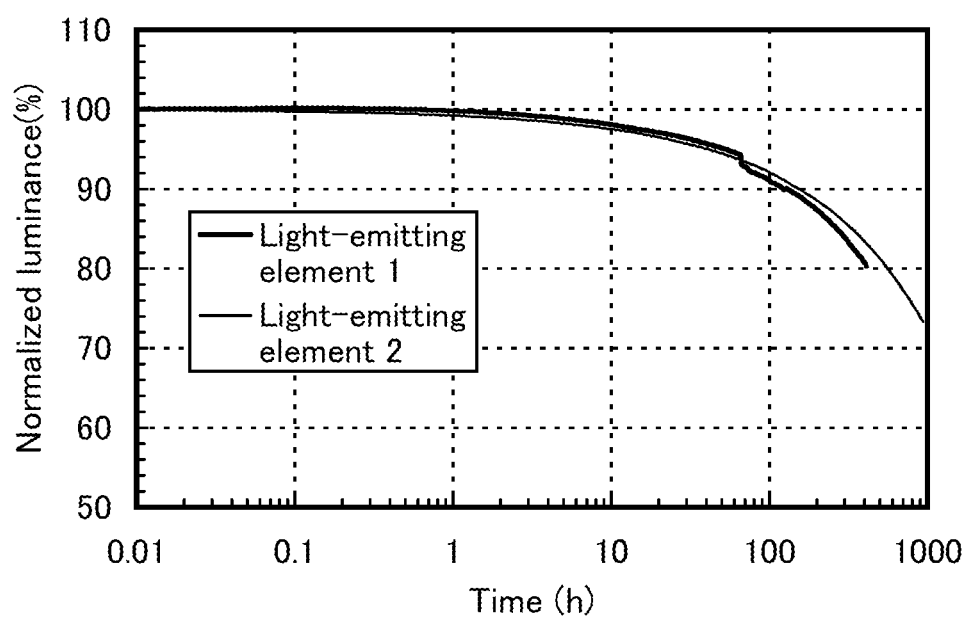
FIG. 25 shows results of reliability tests of the light-emitting elements of Example 4.

Next, the light-emitting elements 1 and 2 were subjected to reliability tests. The results of the reliability tests are shown in FIG. 25. In FIG. 25, the vertical axis represents normalized luminance (%) with an initial luminance of 100% and the horizontal axis represents driving time (h) of the elements. In the reliability tests, the light-emitting elements of this example were driven at room temperature under the conditions where the initial luminance was set to 5000 cd/m$^2$ and the current density was constant. FIG. 25 shows that the light-emitting element 1 kept 80% of the initial luminance after driving for 410 hours and the light-emitting element 2 kept 73% of the initial luminance after driving for 940 hours. These results of the reliability tests revealed that the light-emitting elements 1 and 2 each had a long lifetime.

As described above, by use of NPDBq synthesized in Example 1 or DBqPPn synthesized in Example 3 as the host material in the light-emitting layer and the material in the electron-transport layer, the light-emitting element can have a low driving voltage, high emission efficiency, or a long lifetime.

EXAMPLE 5

In this example, a light-emitting element according to one embodiment of the present invention is described with reference to FIG. 19. Chemical formulas of materials used in this example are shown below. Note that the chemical formulas of the materials which are described above are omitted.

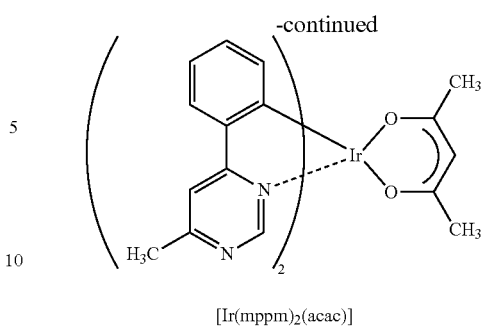

[Ir(mppm)$_2$(acac)]

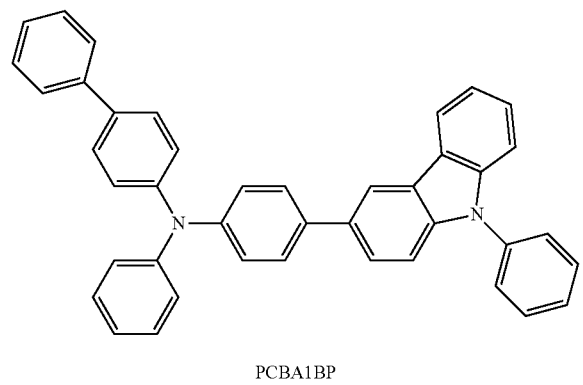

PCBA1BP

The following shows a method of fabricating a light-emitting element 3 of this example.

(Light-Emitting Element 3)

The light-emitting layer 1113 of the light-emitting element 3 was formed by co-evaporation of DBqPPn synthesized in Example 3, 4-phenyl-4'-(9-phenyl-9H-carbazol-3-yl)triphenylamine (abbreviation: PCBA1BP), and (acetylacetonato)bis(6-methyl-4-phenylpyrimidinato)iridium(III) (abbreviation: [Ir(mppm)$_2$(acac)]). Here, the weight ratio of DBqPPn to PCBA1BP and [Ir(mppm)$_2$(acac)] was adjusted to 0.8:0.2:0.05 (=DBqPPn:PCBA1BP[Ir(mppm)$_2$(acac)]). The thickness of the light-emitting layer 1113 was set to 40 nm.

A DBqPPn film was formed to a thickness of 10 nm, whereby the first electron-transport layer 1114*a* of the light-emitting element 3 was formed. The components other than the light-emitting layer 1113 and the first electron-transport layer 1114*a* were formed in the same manner as those of the light-emitting element 1.

Table 3 shows an element structure of the light-emitting element 3 obtained as described above.

TABLE 3

| | First electrode | Hole-injection layer | Hole-transport layer | Light emitting layer | First electron-transport layer | Second electron-transport layer | Electron-injection layer | Second electrode |
|---|---|---|---|---|---|---|---|---|
| Light-emitting element 3 | ITSO 110 nm | DBT3P-II:MoOx (= 4:2) 40 nm | BP AFLP 20 nm | DBqPPn:PCBA1BP:[Ir(mppm)$_2$(acac)] (= 0.8:0.2:0.05) 40 nm | DBqPPn 10 nm | BPhen 20 nm | LiF 1 nm | Al 200 nm |

In a glove box containing a nitrogen atmosphere, the light-emitting element 3 was sealed with a glass substrate so as not to be exposed to the air. Then, operation characteristics of the element were measured. Note that the measurement was carried out at room temperature (in an atmosphere kept at 25° C.).

Figure 26:
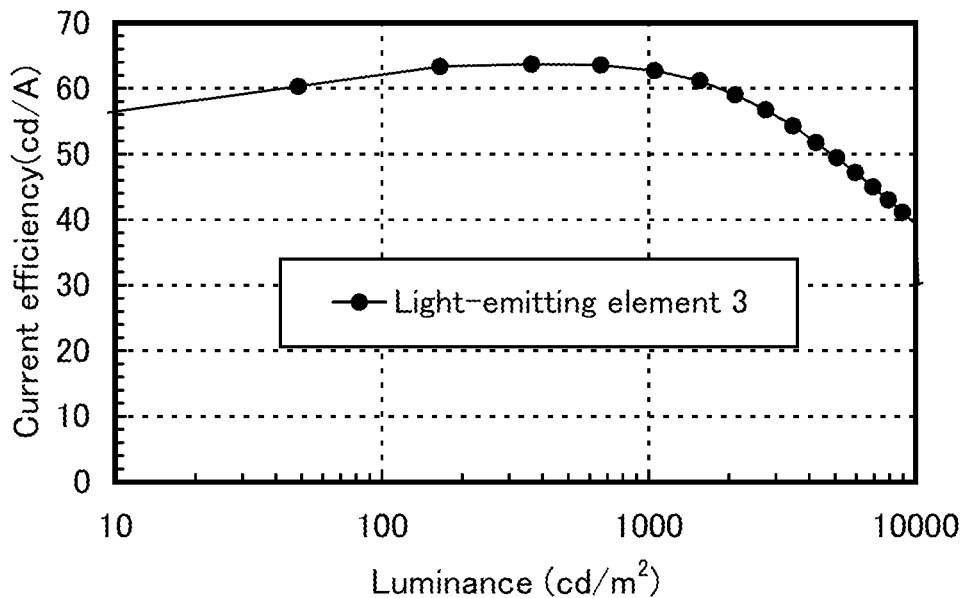
FIG. 26 shows luminance-current efficiency characteristics of a light-emitting element of Example 5.
Figure 27:
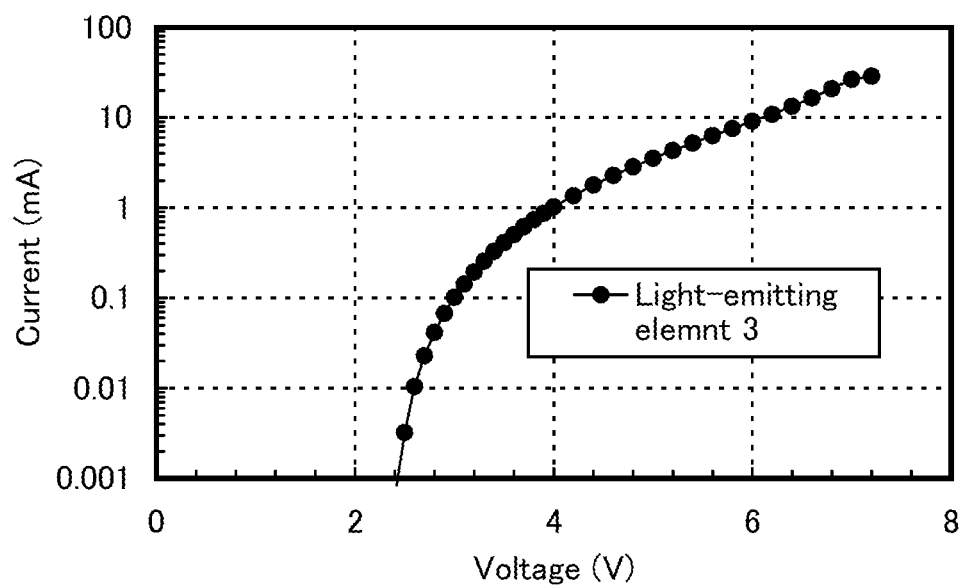
FIG. 27 shows voltage-current characteristics of the light-emitting element of Example 5.
Figure 28:
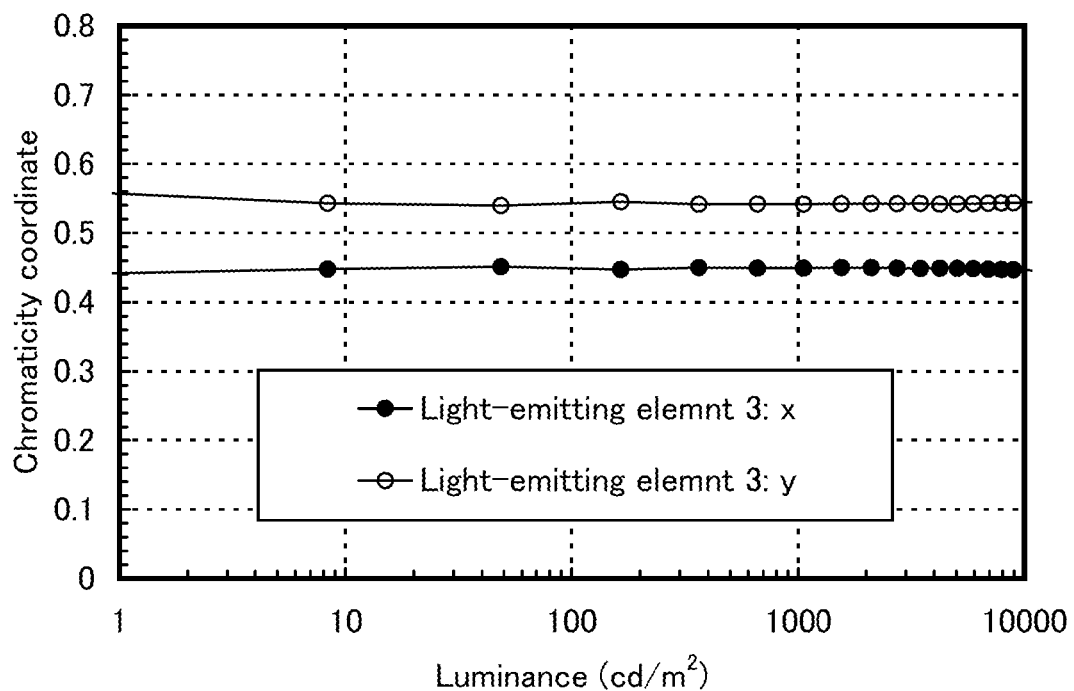
FIG. 28 shows luminance-chromaticity coordinate characteristics of the light-emitting element of Example 5.
Figure 29:
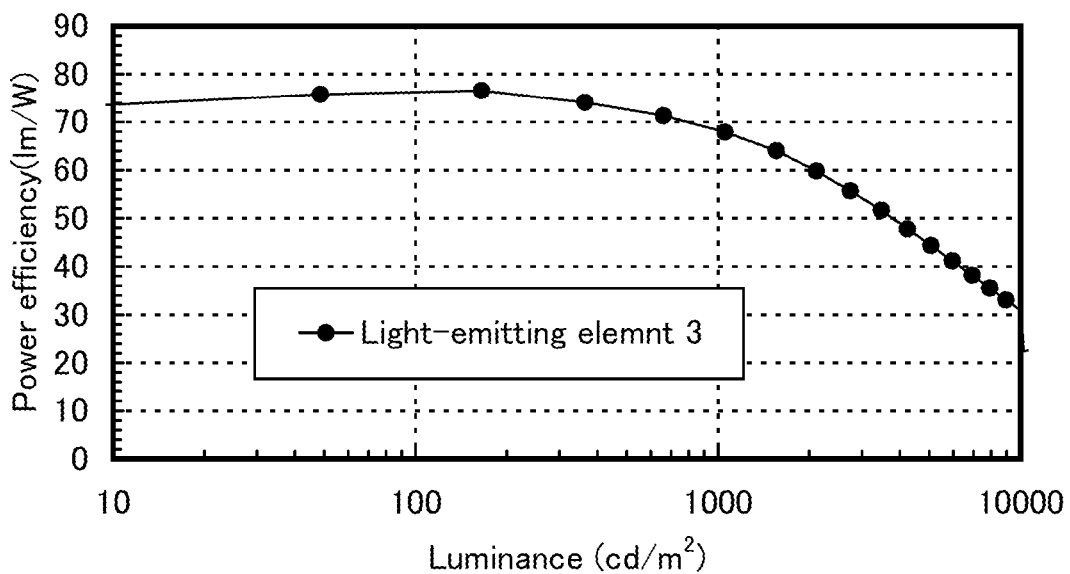
FIG. 29 shows luminance-power efficiency characteristics of the light-emitting element of Example 5.

FIG. 26 shows luminance-current efficiency characteristics of the light-emitting element 3. In FIG. 26, the horizontal axis represents luminance (cd/m$^2$) and the vertical axis represents current efficiency (cd/A). FIG. 27 shows voltage-current characteristics. In FIG. 27, the horizontal axis represents voltage (V) and the vertical axis represents current (mA). FIG. 28 shows luminance-chromaticity coordinate characteristics. In FIG. 28, the horizontal axis represents luminance (cd/m$^2$) and the vertical axis represents chromaticity coordinate (x-coordinate or the y-coordinate). FIG. 29 shows luminance-power efficiency characteristics. In FIG. 29, the horizontal axis represents luminance (cd/m$^2$) and the vertical axis represents power efficiency (lm/W). Further, Table 4 shows voltage (V), current density (mA/cm$^2$), CIE chromaticity coordinates (x, y), current efficiency (cd/A), and external quantum efficiency (%) of the light-emitting element 3 at a luminance of 1100 cd/m$^2$.

TABLE 4

|  | Voltage (V) | Current density (mA/cm$^2$) | Chromaticity (x, y) | | Luminance (cd/m$^2$) | Current efficiency (cd/A) | External quantum efficiency (%) |
|---|---|---|---|---|---|---|---|
| Light-emitting element 3 | 2.9 | 1.7 | 0.45 | 0.54 | 1100 | 62 | 18 |

Figure 30:
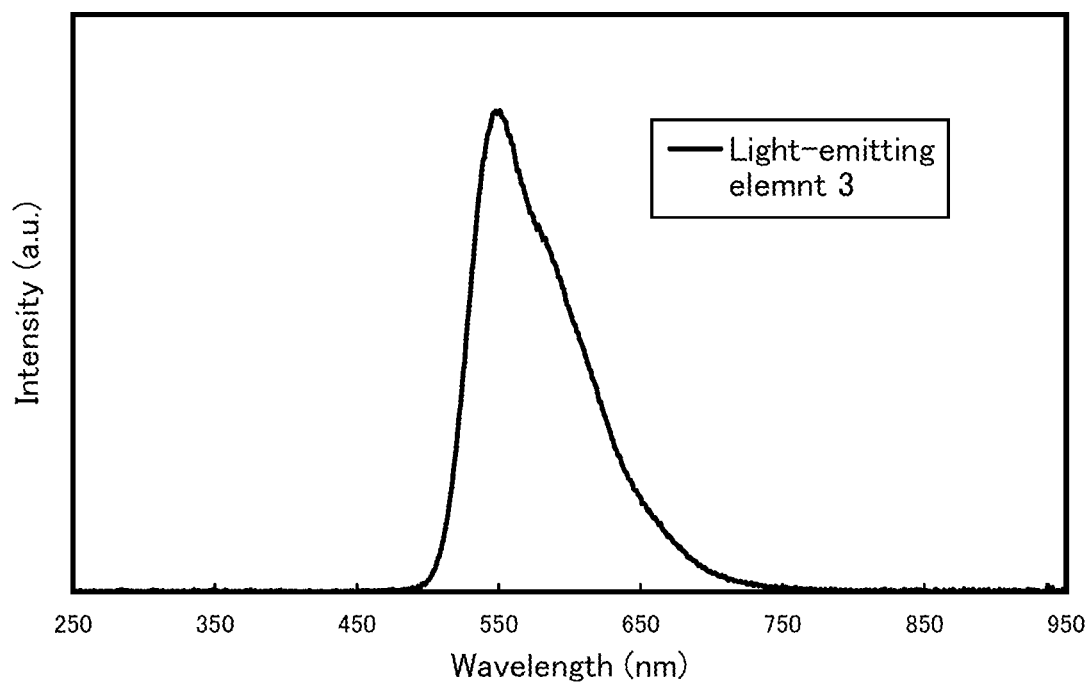
FIG. 30 shows an emission spectrum of the light-emitting element of Example 5.

FIG. 30 shows an emission spectrum of the light-emitting element 3, which was obtained by applying a current of 0.1 mA. In FIG. 30, the horizontal axis represents wavelength (nm) and the vertical axis represents emission intensity (arbitrary unit). As shown in FIG. 30 and Table 4, the CIE chromaticity coordinates of the light-emitting element 3 were (x, y)=(0.45, 0.54) at a luminance of 1100 cd/m$^2$. The light-emitting element 3 was found to emit light originating from [Ir(mppm)$_2$(acac)]. This reveals that DBqPPn, which is the heterocyclic compound according to one embodiment of the present invention, has a T1 level which enables a green phosphorescent material to sufficiently emit light. Accordingly, it is found that DBqPPn can be used as a host material for green to red phosphorescent materials.

FIG. 27 and Table 4 reveal that the light-emitting element 3 is driven at a low voltage. In the light-emitting element 3, DBqPPn, which is the heterocyclic compound according to one embodiment of the present invention, is used as a host material in the light-emitting layer and as a material in the first electron-transport layer. Note that DBqPPn is the heterocyclic compound in which a dibenzo[f,h]quinoxaline ring and a phenanthrene ring are bonded to each other via a para-phenylene group. Accordingly, the light-emitting element can be driven at a low voltage.

FIG. 26, FIG. 29, and Table 4 reveal that the light-emitting element 3 has high current efficiency, high external quantum efficiency, and high power efficiency.

As shown in FIG. 28, the light-emitting element 3 shows substantially no change in color over a range from low luminance to high luminance. It can be said from this result that the light-emitting element 3 is an element having excellent carrier balance.

One of the reasons why the light-emitting element 3 has excellent carrier balance can be the following. In light-emitting layer of the light-emitting element 3, DBqPPn with a high electron-transport property and PCBA1BP with a high hole-transport property are used. Therefore, electrons and holes can be efficiently injected into [Ir(mppm)$_2$(acac)], which is the light-emitting material, so that the light-emitting element has excellent carrier balance.

As described above, by use of DBqPPn synthesized in Example 3 as the host material in the light-emitting layer and the material in the electron-transport layer, the light-emitting element can have a low driving voltage and high emission efficiency.

EXAMPLE 6

In this example, a light-emitting element of one embodiment of the present invention is described with reference to FIG. 19. Chemical formulas of materials used in this example are shown below. Note that the chemical formulas of the materials which are described above are omitted.

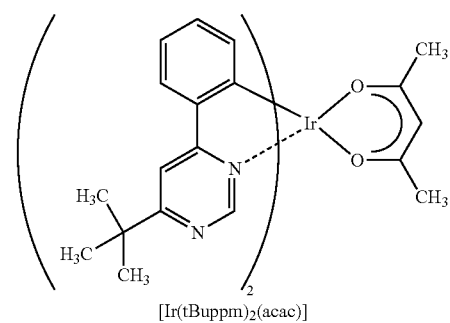

[Ir(tBuppm)$_2$(acac)]

The following shows a method of fabricating a light-emitting element 4 of this example.

(Light-Emitting Element 4)

The light-emitting layer 1113 of the light-emitting element 4 was formed by co-evaporation of 2-[3-(phenanthren-9-yl)phenyl]dibenzo[f,h]quinoxaline (abbreviation: mPnPDBq) synthesized in Example 2, PCBA1BP, and (acetylacetonato)bis(6-tert-butyl-4-phenylpyrimidinato)iridium(III) (abbreviation: [Ir(tBuppm)$_2$(acac)]). Here, the weight ratio of mPnPDBq to PCBA1BP and [Ir(tBuppm)$_2$(acac)] was adjusted to 0.8:0.2:0.05 (=mPnPDBq:PCBA1BP[Ir(tBuppm)$_2$(acac)]). The thickness of the light-emitting layer 1113 was set to 40 nm.

An mPnPDBq film was formed to a thickness of 10 nm, whereby the first electron-transport layer 1114a of the light-emitting element 4 was formed. The components other than the light-emitting layer 1113 and the first electron-transport layer 1114a were formed in the same manner as those of the light-emitting element 1.

Table 5 shows an element structure of the light-emitting element 4 obtained as described above.

TABLE 5

| | First electrode | Hole-injection layer | Hole-transport layer | Light emitting layer | First electron-transport layer | Second electron-transport layer | Electron-injection layer | Second electrode |
|---|---|---|---|---|---|---|---|---|
| Light-emitting element 4 | ITSO 110 nm | DBT3P-II:MoOx (= 4:2) 40 nm | BP AFLP 20 nm | mPnPDBq:PCBA1BP:[Ir(tBuppm)$_2$(acac)] (= 0.8:0.2:0.05) 40 nm | mPnPDBq 10 nm | BPhen 20 nm | LiF 1 nm | Al 200 nm |

In a glove box containing a nitrogen atmosphere, the light-emitting element 4 was sealed with a glass substrate so as not to be exposed to the air. Then, operation characteristics of the element were measured. Note that the measurement was carried out at room temperature (in an atmosphere kept at 25° C.).

Figure 31:
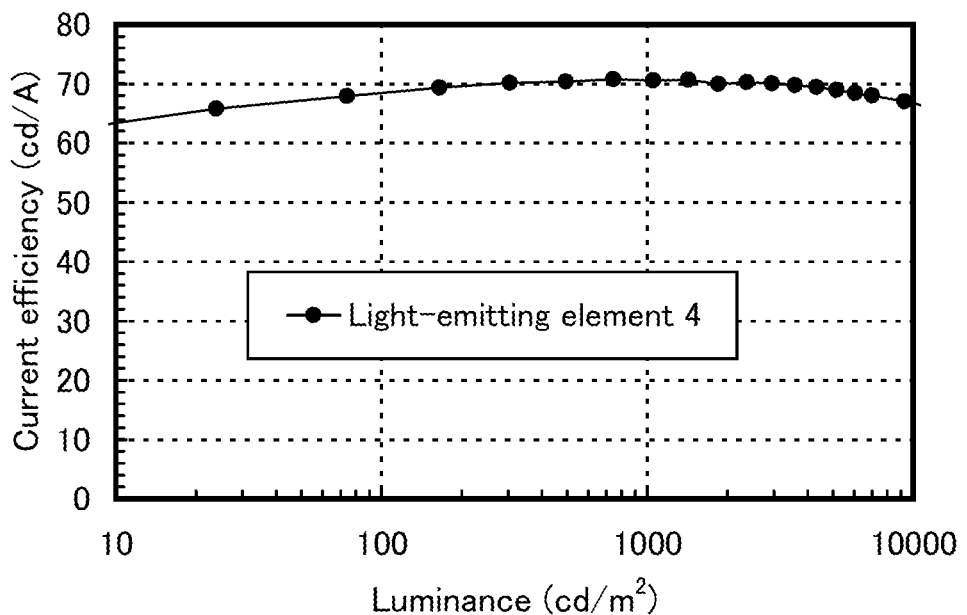
FIG. 31 shows luminance-current efficiency characteristics of a light-emitting element of Example 6.
Figure 32:
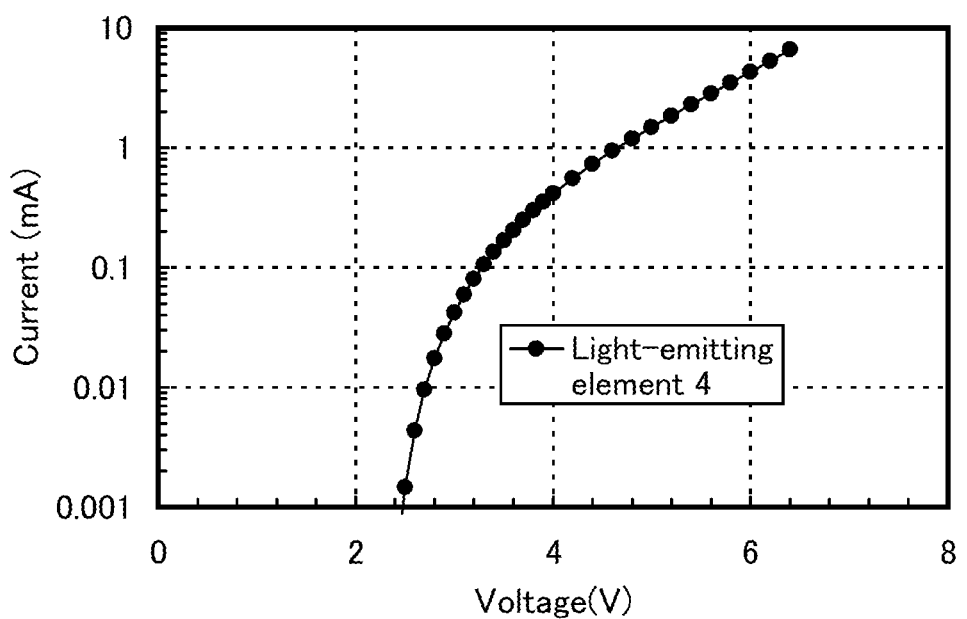
FIG. 32 shows voltage-current characteristics of the light-emitting element of Example 6.
Figure 33:
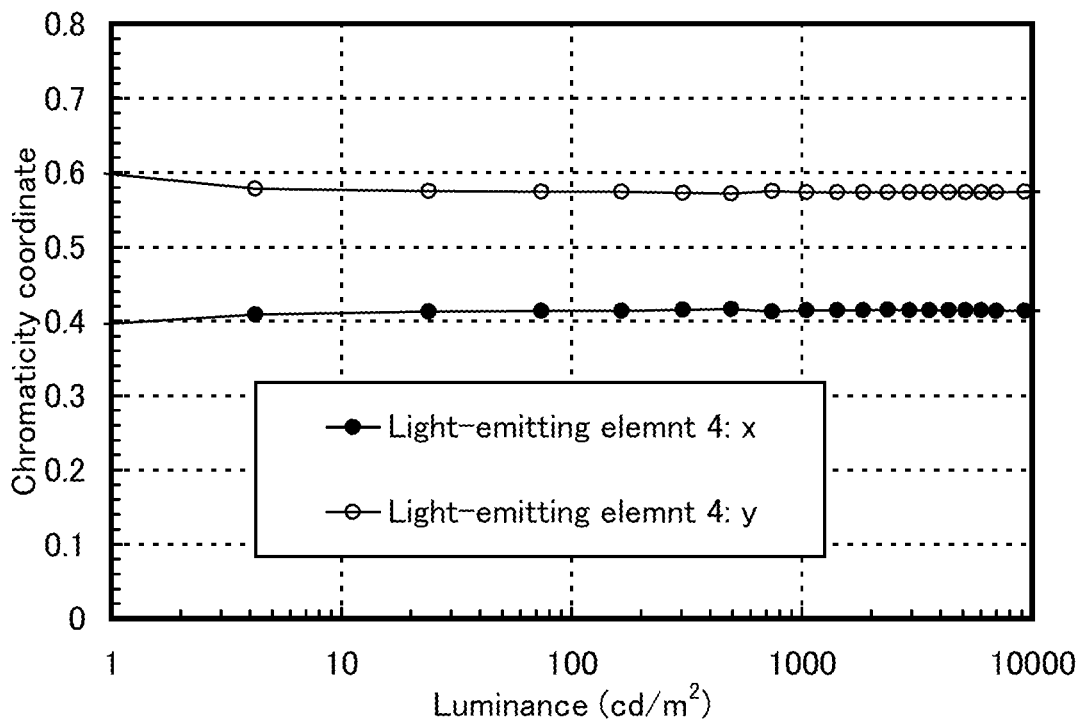
FIG. 33 shows luminance-chromaticity coordinate characteristics of the light-emitting element of Example 6.
Figure 34:
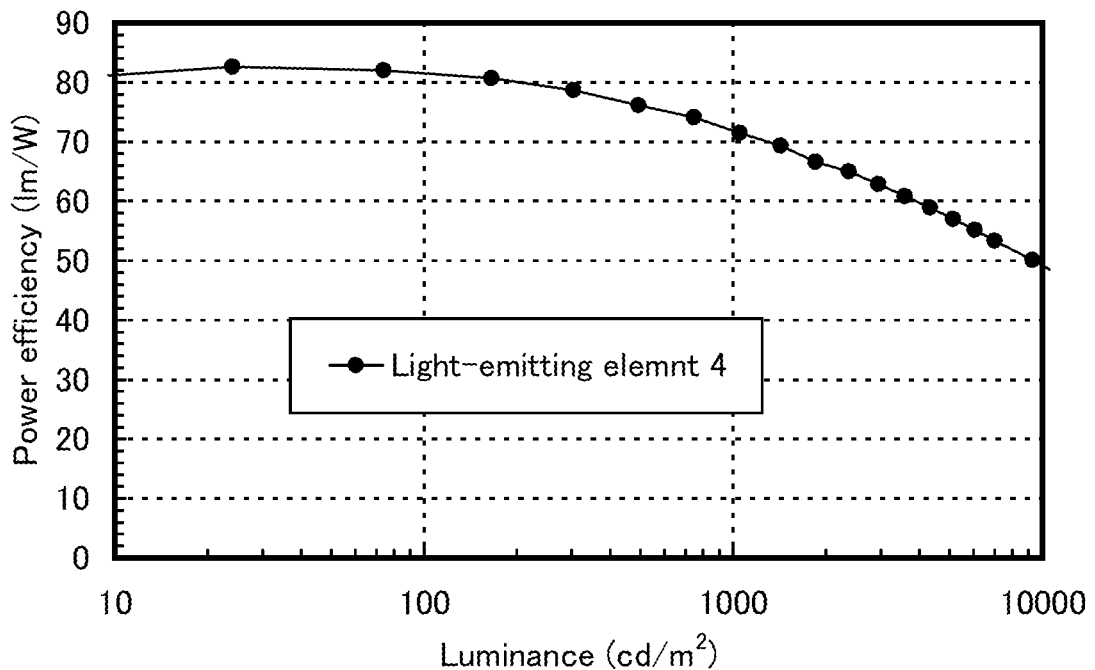
FIG. 34 shows luminance-power efficiency characteristics of the light-emitting element of Example 6.

FIG. 31 shows luminance-current efficiency characteristics of the light-emitting element 4. In FIG. 31, the horizontal axis represents luminance ($cd/m^2$) and the vertical axis represents current efficiency (cd/A). FIG. 32 shows voltage-current characteristics. In FIG. 32, the horizontal axis represents voltage (V) and the vertical axis represents current (mA). FIG. 33 shows luminance-chromaticity coordinate characteristics. In FIG. 33, the horizontal axis represents luminance ($cd/m^2$) and the vertical axis represents chromaticity coordinate (x-coordinate or y-coordinate). FIG. 34 shows luminance-power efficiency characteristics. In FIG. 34, the horizontal axis represents luminance ($cd/m^2$) and the vertical axis represents power efficiency (lm/W). Further, Table 6 shows voltage (V), current density ($mA/cm^2$), CIE chromaticity coordinates (x, y), current efficiency (cd/A), and external quantum efficiency (%) of the light-emitting element 4 at a luminance of 750 $cd/m^2$.

As shown in FIG. 31, the light-emitting element 4 shows a small change in current efficiency over a range from low luminance to high luminance. Further, FIG. 33 reveals that the light-emitting element 4 shows almost no change in color over a range from low luminance to high luminance. It can be said from this result that the light-emitting element 4 is an element having excellent carrier balance.

One of the reasons why the light-emitting element 4 has excellent carrier balance can be the following. In light-emitting layer of the light-emitting element 4, mPnPDBq with a high electron-transport property and PCBA1BP with a high hole-transport property are used. Therefore, electrons and holes can be efficiently injected into [Ir(tBuppm)$_2$(acac)], which is the light-emitting material, so that the light-emitting element has excellent carrier balance.

As described above, by use of mPnPDBq synthesized in Example 2 as the host material in the light-emitting layer and the material in the electron-transport layer, the light-emitting element can have a low driving voltage and high emission efficiency.

TABLE 6

|  | Voltage (V) | Current density ($mA/cm^2$) | Chromaticity (x, y) | | Luminance ($cd/m^2$) | Current efficiency (cd/A) | External quantum efficiency (%) |
|---|---|---|---|---|---|---|---|
| Light-emitting element 4 | 3.0 | 1.1 | 0.41 | 0.57 | 750 | 71 | 20 |

Figure 35:
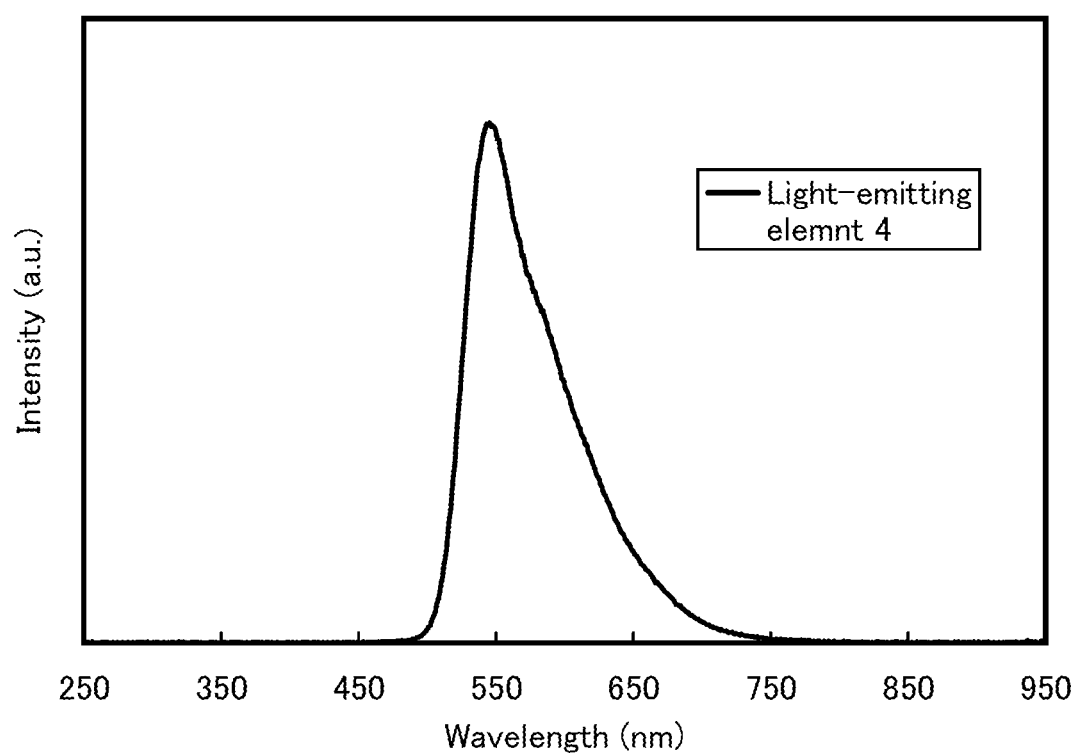
FIG. 35 shows an emission spectrum of the light-emitting element of Example 6.

FIG. 35 shows an emission spectrum of the light-emitting element 4, which was obtained by applying a current of 0.1 mA. In FIG. 35, the horizontal axis represents wavelength (nm) and the vertical axis represents emission intensity (arbitrary unit). As shown in FIG. 35 and Table 6, the CIE chromaticity coordinates of the light-emitting element 4 were (x, y)=(0.41, 0.57) at a luminance of 750 $cd/m^2$. The light-emitting element 4 was found to emit light originating from [Ir(tBuppm)$_2$(acac)]. This reveals that mPnPDBq, which is the heterocyclic compound according to one embodiment of the present invention, has a T1 level which enables a green phosphorescent material to sufficiently emit light. Accordingly, it is found that mPnPDBq can be used as a host material for green to red phosphorescent materials.

FIG. 32 and Table 6 reveal that the light-emitting element 4 is driven at a low voltage. In the light-emitting element 4, mPnPDBq, which is the heterocyclic compound according to one embodiment of the present invention, was used as a host material in the light-emitting layer and a material in the first electron-transport layer. Therefore, the light-emitting element can be driven at a low voltage. Further, FIG. 31, FIG. 34, and Table 6 reveal that the light-emitting element 4 has high current efficiency, high external quantum efficiency, and high power efficiency. Since mPnPDBq is a heterocyclic compound in which a dibenzo[f,h]quinoxaline ring and a phenanthrene ring are bonded to each other via a meta-phenylene group, the light-emitting element can have high emission efficiency.

EXAMPLE 7

In this example, a light-emitting element according to one embodiment of the present invention is described with reference to FIG. 19. Materials used in this example are the same as those used in the above Examples, and their chemical formulas are omitted here.

The following shows a method of fabricating a light-emitting element 5 of this example.

(Light-Emitting Element 5)

The light-emitting layer 1113 of the light-emitting element 5 was formed by co-evaporation of mPnPDBq synthesized in Example 2, PCBA1BP, and [Ir(dppm)$_2$(acac)]. Here, the weight ratio of mPnPDBq to PCBA1BP and [Ir(dppm)$_2$(acac)] was adjusted to 0.8:0.2:0.05 (=mPnPDBq:PCBA1BP[Ir(dppm)$_2$(acac)]). The thickness of the light-emitting layer 1113 was set to 40 nm.

An mPnPDBq film was formed to a thickness of 10 nm, whereby the first electron-transport layer 1114a of the light-emitting element 5 was formed. The components other than the light-emitting layer 1113 and the first electron-transport layer 1114a were formed in the same manner as those of the light-emitting element 1.

Table 7 shows an element structure of the light-emitting element 5 obtained as described above.

TABLE 7

|  | First electrode | Hole-injection layer | Hole-transport layer | Light emitting layer | First electron-transport layer | Second electron-transport layer | Electron-injection layer | Second electrode |
|---|---|---|---|---|---|---|---|---|
| Light-emitting element 5 | ITSO 110 nm | DBT3P-II:MoOx (= 4:2) 40 nm | BP AFLP 20 nm | mPnPDBq:PCBA1BP:[Ir(dppm)$_2$(acac)] (= 0.8:0.2:0.05) 40 nm | mPnPDBq 10 nm | BPhen 20 nm | LiF 1 nm | Al 200 nm |

In a glove box containing a nitrogen atmosphere, the light-emitting element 5 was sealed with a glass substrate so as not to be exposed to the air. Then, operation characteristics of the element were measured. Note that the measurement was carried out at room temperature (in an atmosphere kept at 25° C.).

Figure 36:
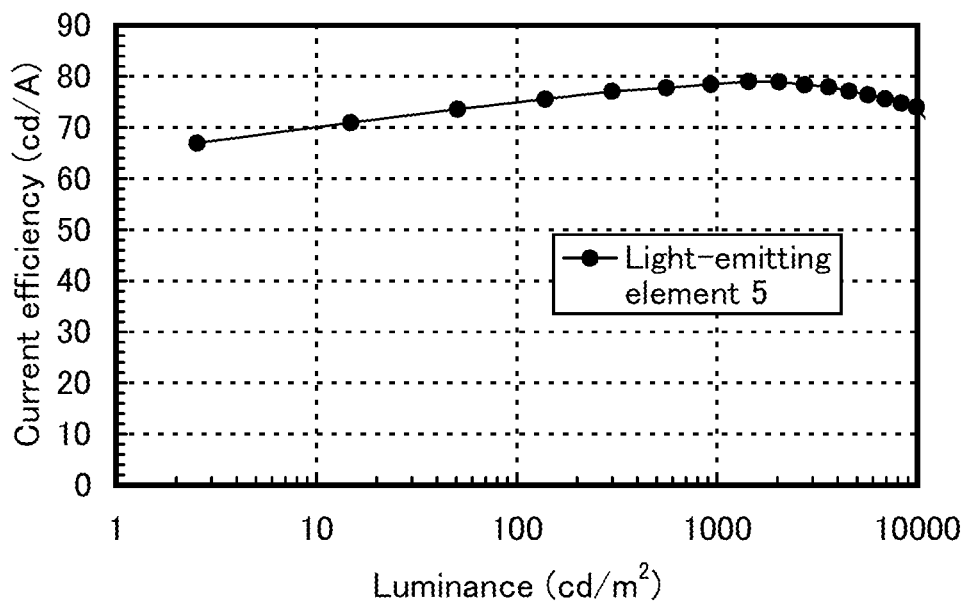
FIG. 36 shows luminance-current efficiency characteristics of a light-emitting element of Example 7.
Figure 37:
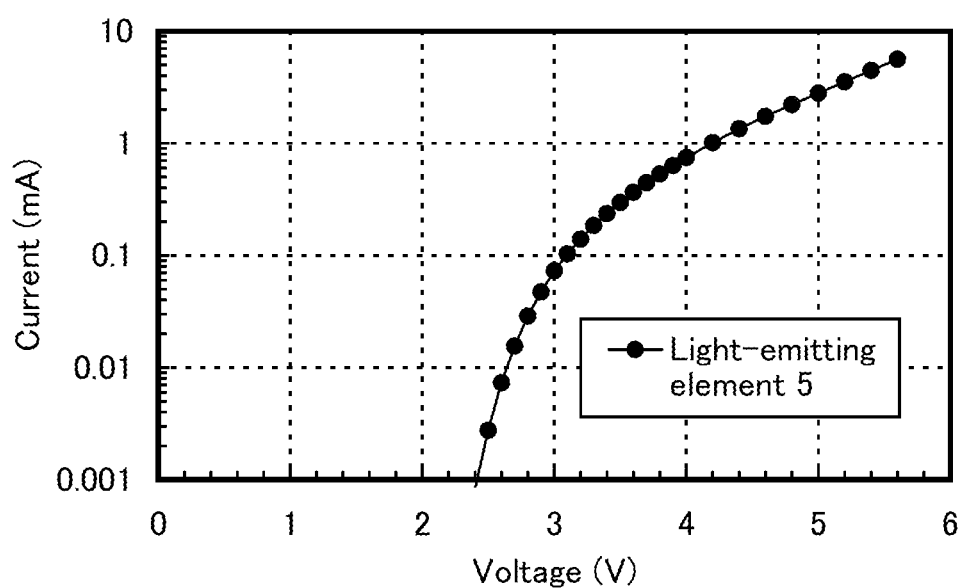
FIG. 37 shows voltage-current characteristics of the light-emitting element of Example 7.
Figure 38:
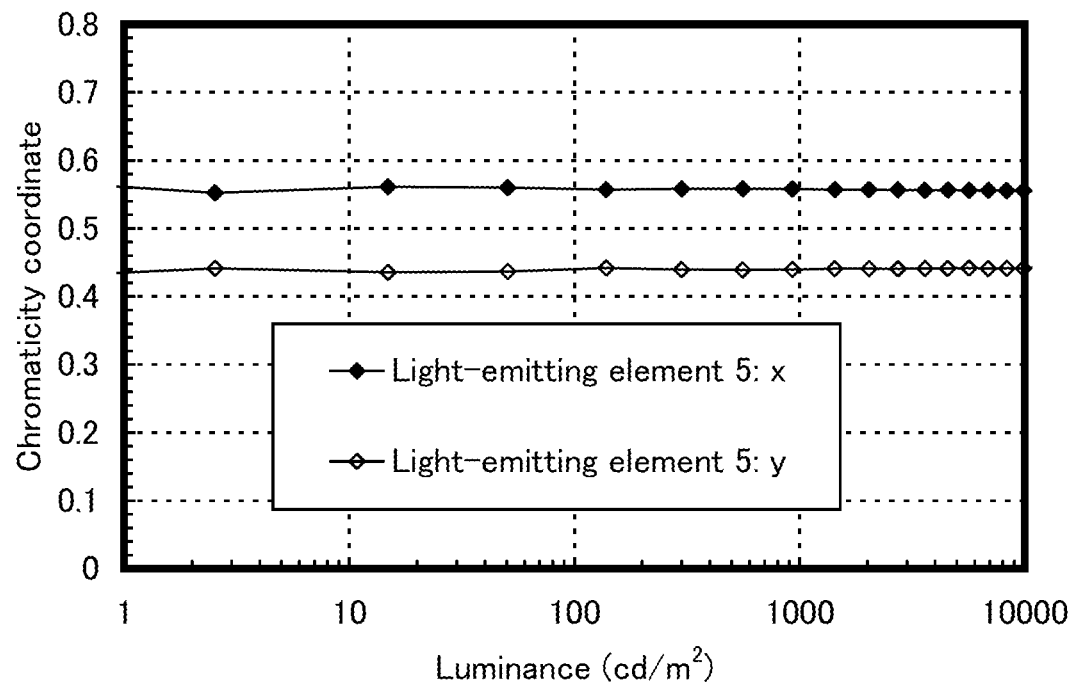
FIG. 38 shows luminance-chromaticity coordinate characteristics of the light-emitting element of Example 7.
Figure 39:
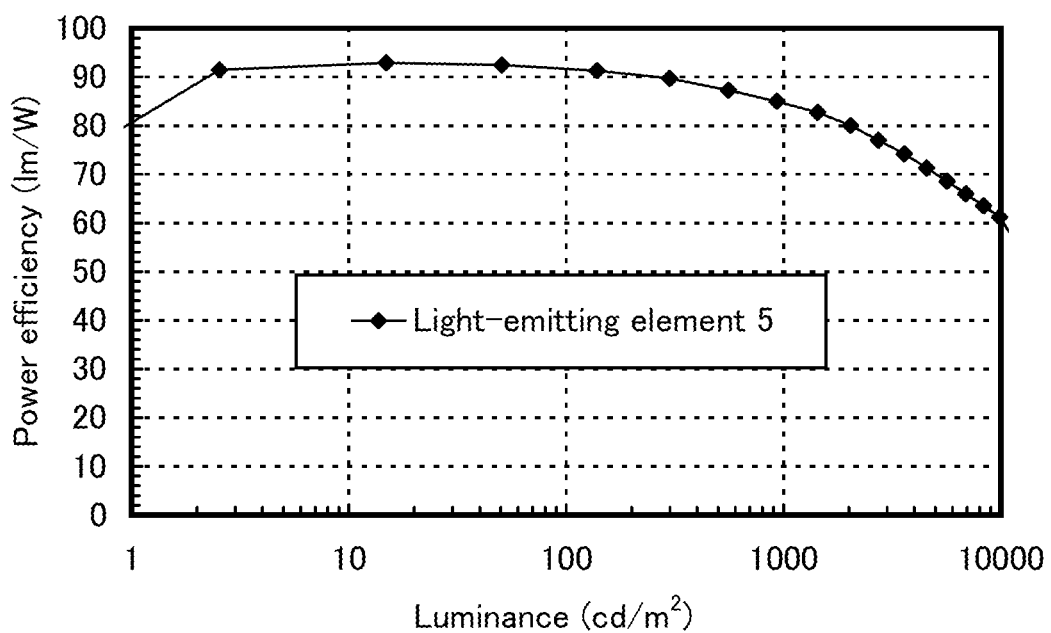
FIG. 39 shows luminance-power efficiency characteristics of the light-emitting element of Example 7.

FIG. 36 shows luminance-current efficiency characteristics of the light-emitting element 5. In FIG. 36, the horizontal axis represents luminance (cd/m$^2$) and the vertical axis represents current efficiency (cd/A). FIG. 37 shows voltage-current characteristics. In FIG. 37, the horizontal axis represents voltage (V) and the vertical axis represents current (mA). FIG. 38 shows luminance-chromaticity coordinate characteristics. In FIG. 38, the horizontal axis represents luminance (cd/m$^2$) and the vertical axis represents chromaticity coordinate (x-coordinate or y-coordinate). FIG. 39 shows luminance-power efficiency characteristics. In FIG. 39, the horizontal axis represents luminance (cd/m$^2$) and the vertical axis represents power efficiency (lm/W). Further, Table 8 shows voltage (V), current density (mA/cm$^2$), CIE chromaticity coordinates (x, y), current efficiency (cd/A), and external quantum efficiency (%) of the light-emitting element 5 at a luminance of 900 cd/m$^2$.

TABLE 8

| | Voltage (V) | Current density (mA/cm$^2$) | Chromaticity (x, y) | | Luminance (cd/m$^2$) | Current efficiency (cd/A) | External quantum efficiency (%) |
|---|---|---|---|---|---|---|---|
| Light-emitting element 5 | 2.9 | 1.2 | 0.56 | 0.44 | 900 | 78 | 30 |

Figure 40:
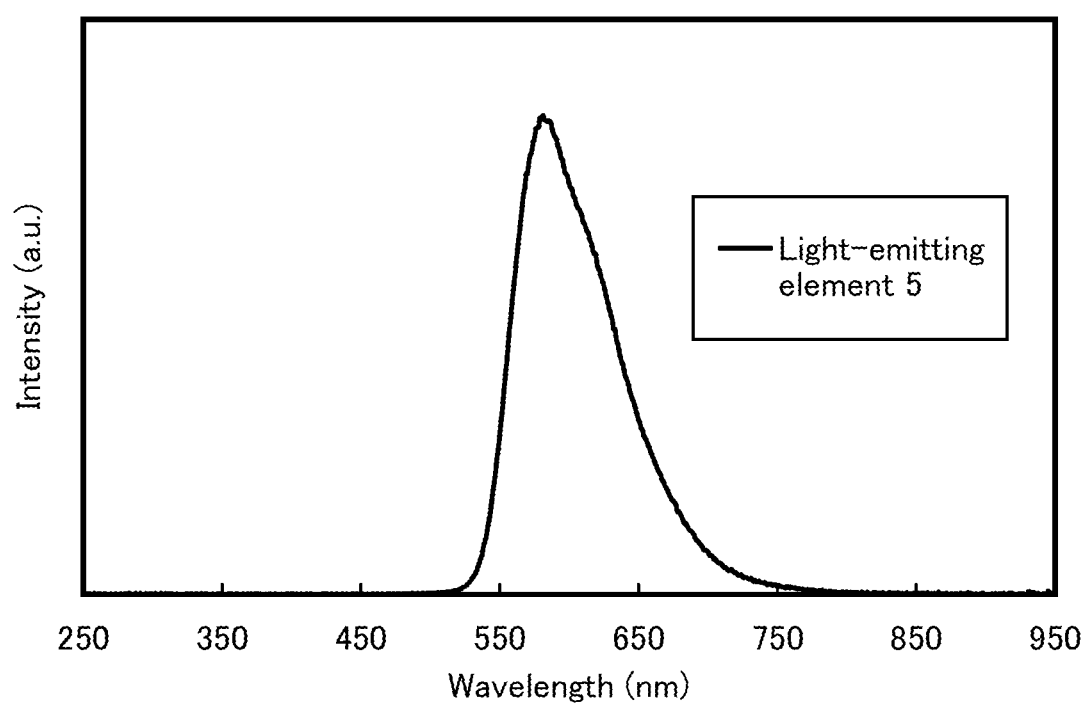
FIG. 40 shows an emission spectrum of the light-emitting element of Example 7.

FIG. 40 shows an emission spectrum of the light-emitting element 5, which was obtained by applying a current of 0.1 mA. In FIG. 40, the horizontal axis represents wavelength (nm) and the vertical axis represents emission intensity (arbitrary unit). As shown in FIG. 40 and Table 8, the CIE chromaticity coordinates of the light-emitting element 5 were (x, y)=(0.56, 0.44) at a luminance of 900 cd/m$^2$. The light-emitting element 5 was found to emit light originating from [Ir(dppm)$_2$(acac)].

FIG. 37 and Table 8 reveal that the light-emitting element 5 is driven at a low voltage. In the light-emitting element 5, mPnPDBq, which is the heterocyclic compound according to one embodiment of the present invention, is used as a host material in the light-emitting layer and as a material in the first electron-transport layer. Accordingly, the light-emitting element can be driven at a low voltage. Further, FIG. 36, FIG. 39, and Table 8 reveal that the light-emitting element 5 has high current efficiency, high external quantum efficiency, and high power efficiency. Since mPnPDBq is a heterocyclic compound in which a dibenzo[f,h]quinoxaline ring and a phenanthrene ring are bonded to each other via a meta-phenylene group, the light-emitting element can have high emission efficiency.

As shown in FIG. 38, the light-emitting element 5 shows a small change in current efficiency over a range from low luminance to high luminance. Further, FIG. 38 reveals that the light-emitting element 5 shows almost no change in color over a range from low luminance to high luminance. It can be said from this result that the light-emitting element 5 is an element having excellent carrier balance.

One of the reasons why the light-emitting element 5 has excellent carrier balance can be the following. In light-emitting layer of the light-emitting element 5, mPnPDBq with a high electron-transport property and PCBA1BP with a high hole-transport property are used. Therefore, electrons and holes can be efficiently injected into [Ir(dppm)$_2$(acac)], which is the light-emitting material, so that the light-emitting element has excellent carrier balance.

Figure 41:
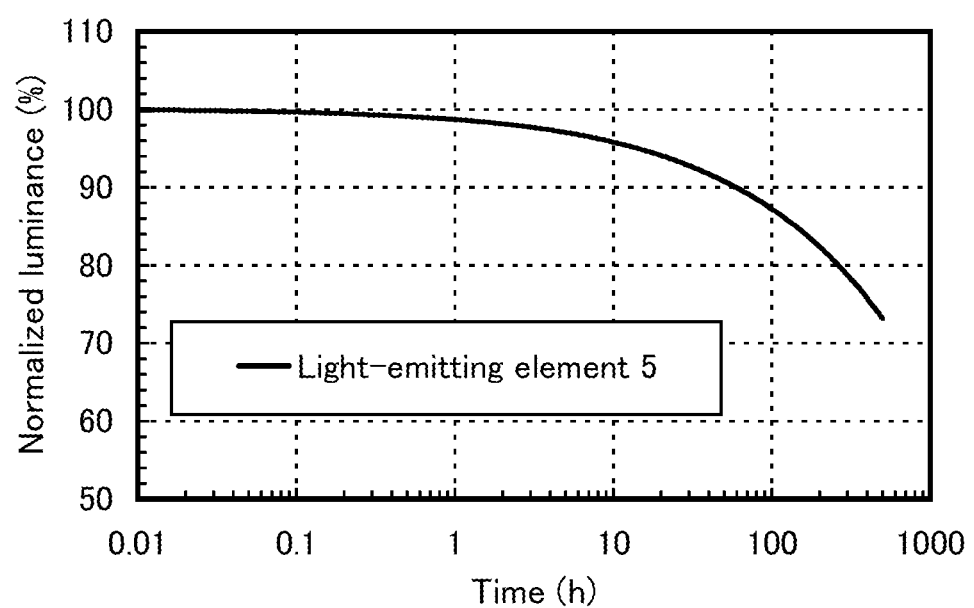
FIG. 41 shows results of reliability tests of the light-emitting element of Example 7.

Next, the light-emitting element 5 was subjected to reliability tests. The results of the reliability tests are shown in FIG. 41. In FIG. 41, the vertical axis represents normalized luminance (%) with an initial luminance of 100% and the horizontal axis represents driving time (h) of the element. In the reliability tests, the light-emitting element of this example was driven at room temperature under the conditions where the initial luminance was set to 5000 cd/m$^2$ and the current density was constant. FIG. 41 shows that the light-emitting element 5 kept 73% of the initial luminance after driving for 500 hours. These results of the reliability tests revealed that the light-emitting element 5 had a long lifetime.

As described above, by use of mPnPDBq synthesized in Example 2 as the host material in the light-emitting layer and the material in the electron-transport layer, the light-emitting element can have a low driving voltage, high emission efficiency, and a long lifetime.

Reference Example 1

This example specifically shows a method of synthesizing (acetylacetonato)bis(4,6-diphenylpyrimidinato)iridium(III) (abbreviation: [Ir(dppm)$_2$(acac)]) used in Examples 4 and 7. The structure of [Ir(dppm)$_2$(acac)] is shown below.

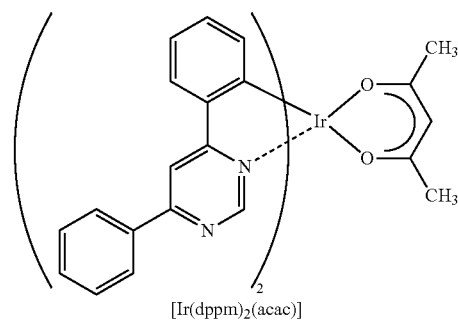

[Ir(dppm)$_2$(acac)]

Step 1: Synthesis of 4,6-diphenylpyrimidine (abbreviation: Hdppm)

First, into a recovery flask equipped with a reflux pipe, 5.02 g of 4,6-dichloropyrimidine, 8.29 g of phenylboronic acid, 7.19 g of sodium carbonate, 0.29 g of bis(triphenylphosphine)palladium(II)dichloride (abbreviation: Pd(PPh$_3$)$_2$Cl$_2$), 20 mL of water, and 20 mL of acetonitrile were put, and the air in the flask was replaced with argon. This reaction container was subjected to irradiation with microwaves (2.45 GHz, 100 W) for one hour to be heated. Here, into the flask, 2.08 g of phenylboronic acid, 1.79 g of sodium carbonate, 0.070 g of Pd(PPh$_3$)$_2$Cl$_2$, 5 mL of water, and 5 mL of acetonitrile were further put, and the reaction container was heated again by irradiation with microwaves (2.45 GHz, 100 W) for one hour. Then, water was added to this solution and an organic layer was extracted with dichloromethane. The obtained extract was washed with water and dried with magnesium sulfate. The solution which had been dried was filtered. The solvent of this solution was distilled off, and then the obtained residue was purified by silica gel column chromatography using dichloromethane as a developing solvent. As a result, a pyrimidine derivative Hdppm (yellow white powder, yield of 38%) was obtained. Note that the irradiation with microwaves was performed using a microwave synthesis system (Discover, produced by CEM Corporation). A synthesis scheme (a-1) of Step 1 is illustrated below.

(a-1)

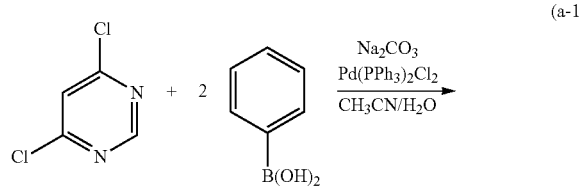

Step 2: Synthesis of di-μ-chloro-bis[bis(4,6-diphenylpyrimidinato)iridium(III)](abbreviation: [Ir(dppm)₂Cl]₂)

Next, into a recovery flask equipped with a reflux pipe, 15 mL of 2-ethoxyethanol, 5 mL of water, 1.10 g of Hdppm obtained in the above Step 1, and 0.69 g of iridium chloride hydrate (IrCl₃·H₂O) were put, and the air in the flask was replaced with argon. After that, irradiation with microwaves (2.45 GHz, 100 W) was performed for one hour to cause a reaction. After the solvent was distilled off, the obtained residue was filtered with ethanol and washed to give a dinuclear complex [Ir(dppm)₂Cl]₂ (reddish brown powder, yield of 88%). A synthesis scheme (a-2) of Step 2 is illustrated below.

(a-2)

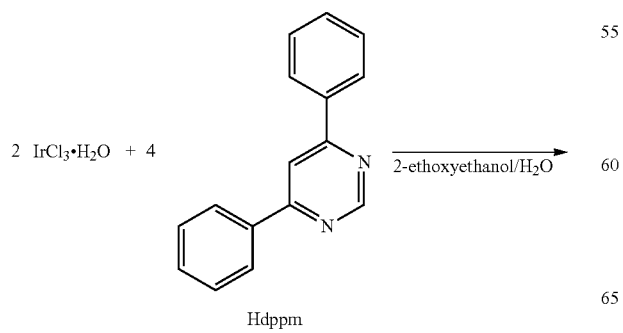

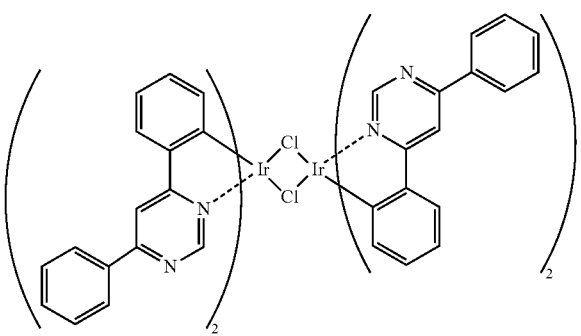

[Ir(dppm)₂Cl]₂

Step 3: Synthesis of (acetylacetonato)bis(4,6-diphenylpyrimidinato)iridium(III) (abbreviation: [Ir(dppm)₂(acac)])

Furthermore, into a recovery flask equipped with a reflux pipe, 40 mL of 2-ethoxyethanol, 1.44 g of [Ir(dppm)₂Cl]₂ obtained in the above Step 2, 0.30 g of acetylacetone, and 1.07 g of sodium carbonate were put, and the air in the flask was replaced with argon. After that, irradiation with microwaves (2.45 GHz, 120 W) was performed for one hour to cause a reaction. The solvent was distilled off, the obtained residue was dissolved in dichloromethane, and filtration was performed to remove insoluble part. The obtained filtrate was washed with water and then with saturated saline, and was dried with magnesium sulfate. The solution which had been dried was filtered. The solvent of this solution was distilled off, and then the obtained residue was purified by silica gel column chromatography using dichloromethane and ethyl acetate as a developing solvent in a volume ratio of 50:1. After that, recrystallization was carried out with a mixed solvent of dichloromethane and hexane to give orange powder that was the objective substance (yield of 32%). A synthesis scheme (a-3) of Step 3 is illustrated below.

(a-3)

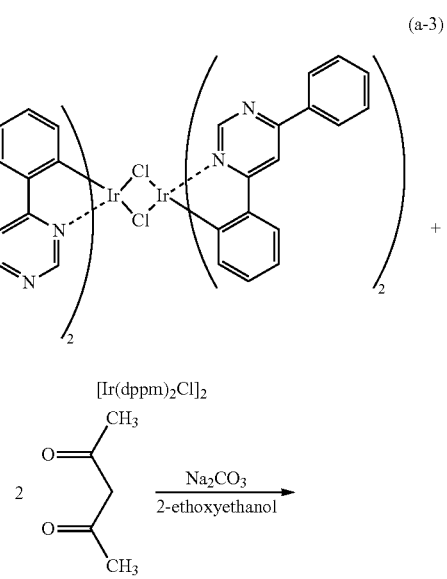

-continued

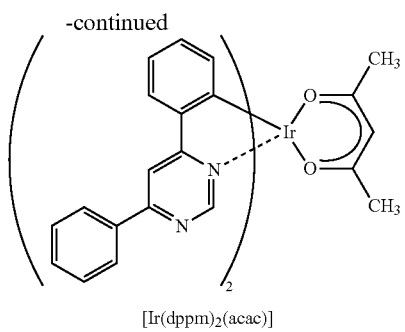

[Ir(dppm)₂(acac)]

Analysis results of the orange powder obtained in the above Step 3 by nuclear magnetic resonance spectrometry (¹H NMR) are shown below. The results show that [Ir(dppm)₂(acac)] was obtained in this synthesis example.

¹H NMR. δ(CDCl₃): 1.83 (s, 6H), 5.29 (s, 1H), 6.48 (d, 2H), 6.80 (t, 2H), 6.90 (t, 2H), 7.55-7.63 (m, 6H), 7.77 (d, 2H), 8.17 (s, 2H), 8.24 (d, 4H), 9.17 (s, 2H).

Reference Example 2

This example specifically shows a method of synthesizing (acetylacetonato)bis(6-methyl-4-phenylpyrimidinato)iridium(III) (abbreviation: [Ir(mppm)₂(acac)]) used in Example 5. The structure of [Ir(mppm)₂(acac)] is shown below.

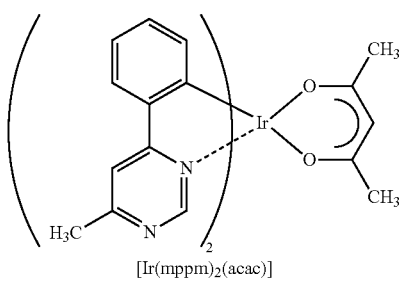

[Ir(mppm)₂(acac)]

Step 1: Synthesis of 4-methyl-6-phenylpyrimidine (abbreviation: Hmppm)

First, into a recovery flask equipped with a reflux pipe, 4.90 g of 4-chloro-6-methylpyrimidine, 4.80 g of phenylboronic acid, 4.03 g of sodium carbonate, 0.16 g of bis(triphenylphosphine)palladium(II)dichloride (abbreviation: Pd(PPh₃)₂Cl₂), mL of water, and 10 mL of acetonitrile were put, and the air in the flask was replaced with argon. This reaction container was subjected to irradiation with microwaves (2.45 GHz, 100 W) for one hour to be heated. Here, into the flask, 2.28 g of phenylboronic acid, 2.02 g of sodium carbonate, 0.082 g of Pd(PPh₃)₂Cl₂, 5 mL of water, and 10 mL of acetonitrile were further put, and the reaction container was heated again by irradiation with microwaves (2.45 GHz, 100 W) for one hour. After that, water was added to this solution and extraction with dichloromethane was carried out. The obtained solution of the extract was washed with a saturated aqueous solution of sodium carbonate, water, and then with saturated saline, and dried with magnesium sulfate. The solution which had been dried was filtered. The solvent of this solution was distilled off, and then the obtained residue was purified by silica gel column chromatography using dichloromethane and ethyl acetate as a developing solvent in a volume ratio of 9:1, so that a pyrimidine derivative Hmppm, which was the objective substance, was obtained (orange oily substance, yield of 46%). Note that the irradiation with microwaves was performed using a microwave synthesis system (Discover, produced by CEM Corporation). A synthesis scheme (b-1) of Step 1 is illustrated below.

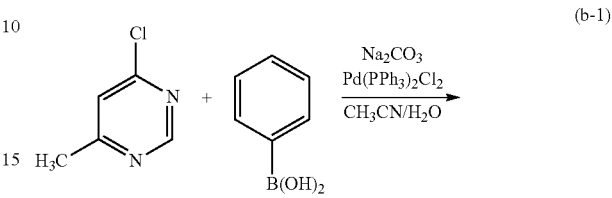

(b-1)

Hmppm

Step 2: Synthesis of di-μ-chloro-bis[bis(6-methyl-4-phenylpyrimidinato)iridium(III)] (abbreviation: [Ir(mppm)₂Cl]₂)

Next, into a recovery flask equipped with a reflux pipe, 15 mL of 2-ethoxyethanol, 5 mL of water, 1.51 g of Hmppm obtained in Step 1, and 1.26 g of iridium chloride hydrate (IrCl₃·H₂O) were put, and the air in the flask was replaced with argon. After that, irradiation with microwaves (2.45 GHz, 100 W) was performed for one hour to cause a reaction. The solvent was distilled off, and then the obtained residue was washed with ethanol and filtered to give a dinuclear complex [Ir(mppm)₂Cl]₂ (dark green powder, yield of 77%). A synthesis scheme (b-2) of Step 2 is illustrated below.

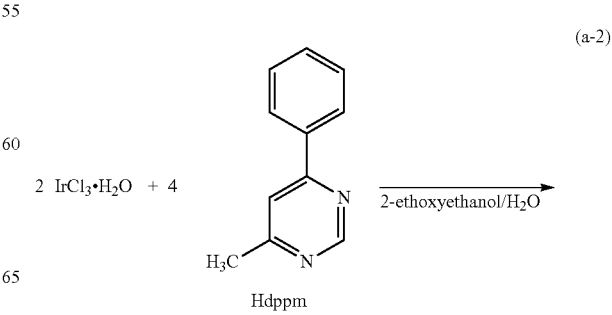

(a-2)

Hdppm

-continued

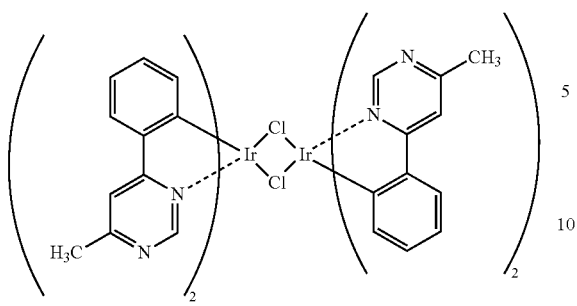

[Ir(dppm)₂Cl]₂

Step 3: Synthesis of (acetylacetonato)bis(6-methyl-4-phenylpyrimidinato)iridium(III) (abbreviation: [Ir(mppm)₂(acac)])

Furthermore, into a recovery flask equipped with a reflux pipe, 40 mL of 2-ethoxyethanol, 1.84 g of the dinuclear complex [Ir(mppm)₂Cl]₂ obtained in the above Step 2, 0.48 g of acetylacetone, and 1.73 g of sodium carbonate were put, and the air in the flask was replaced with argon. After that, irradiation with microwaves (2.45 GHz, 120 W) was performed for one hour to cause a reaction. The solvent was distilled off, the obtained residue was dissolved in dichloromethane, and filtration was performed to remove insoluble part. The obtained filtrate was washed with water and then with saturated saline, and was dried with magnesium sulfate. The solution which had been dried was filtered. The solvent of this solution was distilled off, and then the obtained residue was purified by silica gel column chromatography using dichloromethane and ethyl acetate as a developing solvent in a volume ratio of 4:1. After that, recrystallization was carried out with a mixed solvent of dichloromethane and hexane to give the objective substance as yellow powder (yield of 22%). A synthesis scheme (b-3) of Step 3 is illustrated below.

(b-3)

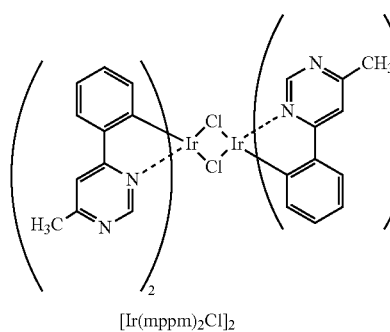

[Ir(mppm)₂Cl]₂

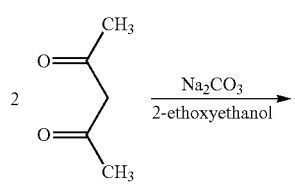

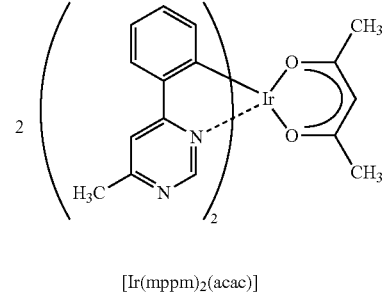

[Ir(mppm)₂(acac)]

Analysis results of the yellow powder obtained in the above Step 3 by nuclear magnetic resonance spectrometry (¹H NMR) are shown below. The results show that [Ir(mppm)₂(acac)] was obtained in this synthesis example.

¹H NMR. δ(CDCl₃): 1.78 (s, 6H), 2.81 (s, 6H), 5.24 (s, 1H), 6.37 (d, 2H), 6.77 (t, 2H), 6.85 (t, 2H), 7.61-7.63 (m, 4H), 8.97 (s, 2H).

Reference Example 3

This example specifically shows a method of synthesizing (acetylacetonato)bis(6-tert-butyl-4-phenylpyrimidinato)iridium(III) (abbreviation: [Ir(tBuppm)₂(acac)]) used in Example 6. The structure of [Ir(tBuppm)₂(acac)] is shown below.

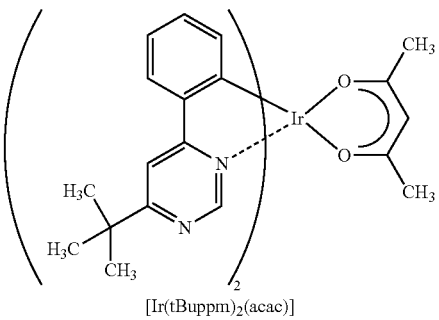

[Ir(tBuppm)₂(acac)]

Step 1: Synthesis of 4-tert-butyl-6-phenylpyrimidine (abbreviation: HtBuppm)

First, into a recovery flask equipped with a reflux pipe, 22.5 g of 4,4-dimethyl-1-phenylpentane-1,3-dione and 50 g of formamide were put, and the air in the flask was replaced with nitrogen. This reaction container was heated, so that the reacted solution was refluxed for five hours. After that, this solution was poured into an aqueous solution of sodium hydroxide, and an organic layer was extracted with dichloromethane. The obtained organic layer was washed with water and saturated saline, and dried with magnesium sulfate. The solution which had been dried was filtered. The solvent of this solution was distilled off, and then the obtained residue was purified by silica gel column chromatography using hexane and ethyl acetate as a developing solvent in a volume ratio of 10:1, so that a pyrimidine derivative HtBuppm (colorless oily substance, yield of 14%) was obtained. A synthesis scheme of Step 1 is illustrated in the following (c-1).

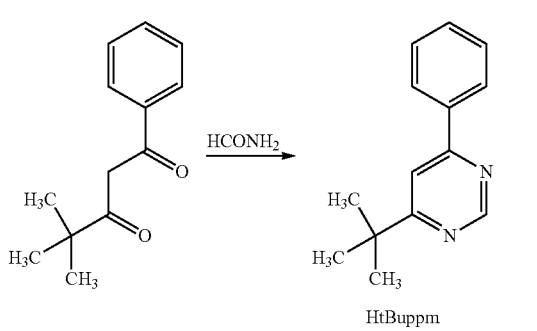

(c-1)

HtBuppm

Step 2: Synthesis of di-μ-chloro-bis[bis(6-tert-butyl-4-phenylpyrimidinato)iridium(III)] (abbreviation: [Ir(tBuppm)₂Cl]₂)

Next, into a recovery flask equipped with a reflux pipe, 15 mL of 2-ethoxyethanol, 5 mL of water, 1.49 g of HtBuppm obtained in the above Step 1, and 1.04 g of iridium chloride hydrate (IrCl₃·H₂O) were put, and the air in the flask was replaced with argon. After that, irradiation with microwaves (2.45 GHz, 100 W) was performed for one hour to cause a reaction. The solvent was distilled off, and then the obtained residue was suction-filtered and washed with ethanol to give a dinuclear complex [Ir(tBuppm)₂Cl]₂ (yellow green powder, yield of 73%). A synthesis scheme of Step 2 is illustrated in the following (c-2).

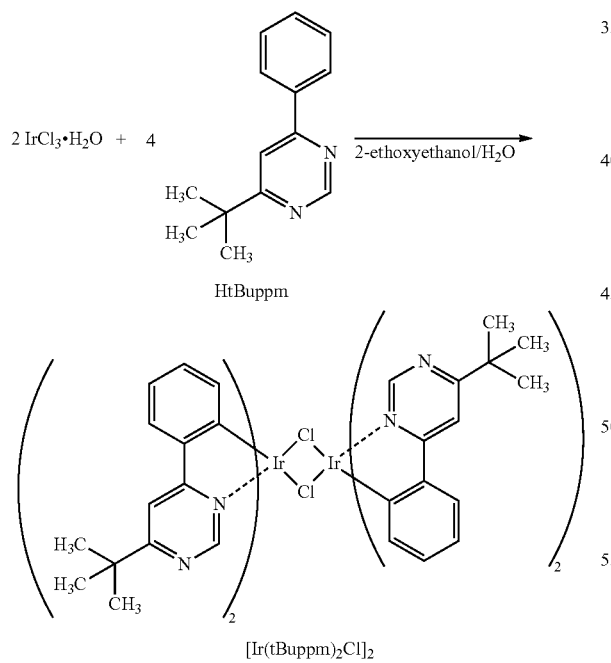

Step 3: Synthesis of (acetylacetonato)bis(6-tert-butyl-4-phenylpyrimidinato)iridium(III) (abbreviation: [Ir(tBuppm)₂(acac)])

Further, into a recovery flask equipped with a reflux pipe, 40 mL of 2-ethoxyethanol, 1.61 g of the dinuclear complex [Ir(tBuppm)₂Cl]₂ obtained in the above Step 2, 0.36 g of acetylacetone, and 1.27 g of sodium carbonate were put, and the air in the flask was replaced with argon. After that, irradiation with microwaves (2.45 GHz, 120 W) was performed for one hour to cause a reaction. The solvent was distilled off, and the obtained residue was suction-filtered with ethanol and washed with water and ethanol. This solid was dissolved in dichloromethane, and the mixture was filtered through a filter aid in which Celite (produced by Wako Pure Chemical Industries, Ltd., Catalog No. 531-16855), alumina, and Celite were stacked in this order. The solvent was distilled off, and the obtained solid was recrystallized with a mixed solvent of dichloromethane and hexane, so that the objective substance was obtained as yellow powder (yield of 68%). A synthesis scheme of Step 3 is illustrated in the following (c-3).

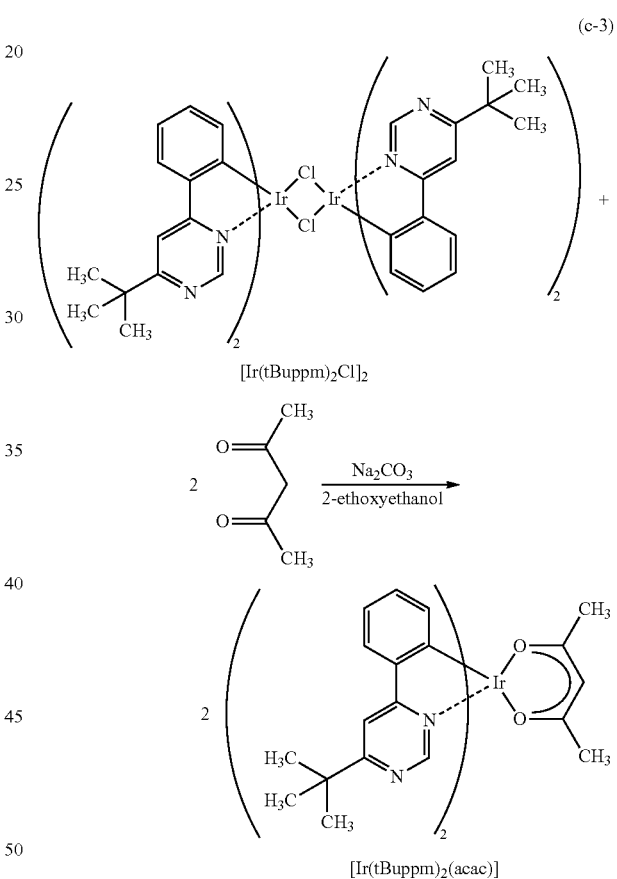

Analysis results of the yellow powder obtained in the above Step 3 by nuclear magnetic resonance spectrometry ($^1$H NMR) are shown below. The results show that [Ir(tBuppm)₂(acac)] was obtained in this synthesis example.

$^1$H NMR. δ (CDCl₃): 1.50 (s, 18H), 1.79 (s, 6H), 5.26 (s, 1H), 6.33 (d, 2H), 6.77 (t, 2H), 6.85 (t, 2H), 7.70 (d, 2H), 7.76 (s, 2H), 9.02 (s, 2H).

This application is based on Japanese Patent Application serial no. 2011-189086 filed with Japan Patent Office on Aug. 31, 2011, and Japanese Patent Application serial no. 2012-152280 filed with Japan Patent Office on Jul. 6, 2012, the entire contents of which are hereby incorporated by reference.

What is claimed is:

1. An organic compound represented by a formula (G1):

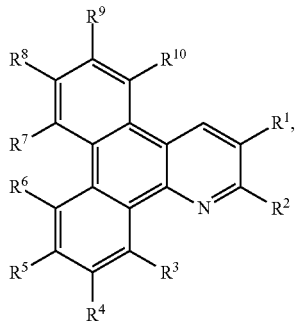
(G1)

wherein any one of $R^1$ to $R^{10}$ represents a substituent represented by a formula (G1-1), another one of $R^1$ to $R^{10}$ represents hydrogen, an alkyl group having 1 to 6 carbon atoms, a substituted or unsubstituted phenyl group, a substituted or unsubstituted biphenyl group, or a substituent represented by a formula (G1-2), and the others separately represent hydrogen, an alkyl group having 1 to 6 carbon atoms, a substituted or unsubstituted phenyl group, or a substituted or unsubstituted biphenyl group:

(G1-1)

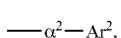
(G1-2)

wherein one of $R^1$ and $R^2$ represents hydrogen,
wherein $\alpha^1$ in the formula (G1-1) and $\alpha^2$ in the formula (G1-2) separately represent a substituted or unsubstituted phenylene group or a substituted or unsubstituted biphenyldiyl group, and
wherein $Ar^1$ in the formula (G1-1) and $Ar^2$ in the formula (G1-2) separately represent a substituted or unsubstituted naphthyl group, a substituted or unsubstituted phenanthryl group, or a substituted or unsubstituted triphenylenyl group.

2. The organic compound according to claim 1,
wherein the organic compound is represented by a formula (G2-1):

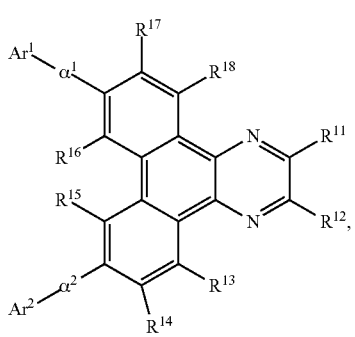
(G2-1)

wherein $R^{11}$ to $R^{18}$ separately represent hydrogen, an alkyl group having 1 to 6 carbon atoms, a substituted or unsubstituted phenyl group, or a substituted or unsubstituted biphenyl group, and
wherein one of $R^{11}$ and $R^{12}$ represents hydrogen.

3. The organic compound according to claim 1,
wherein the organic compound is represented by a formula (G2-2):

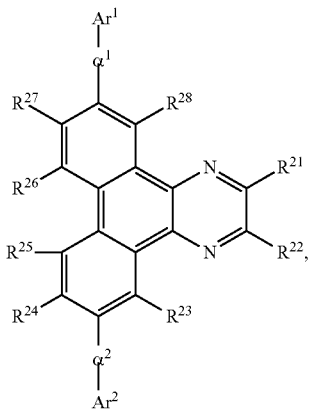
(G2-2)

wherein $R^{21}$ to $R^{28}$ separately represent hydrogen, an alkyl group having 1 to 6 carbon atoms, a substituted or unsubstituted phenyl group, or a substituted or unsubstituted biphenyl group, and
wherein one of $R^{21}$ and $R^{22}$ represents hydrogen.

4. The organic compound according to claim 1,
wherein $\alpha^1$ and $\alpha^2$ are separately represented by a formula ($\alpha$-1) or a formula ($\alpha$-2):

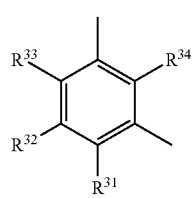
($\alpha$-1)

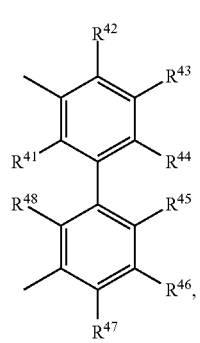
($\alpha$-2)

and
wherein $R^{31}$ to $R^{34}$ in the formula ($\alpha$-1) and $R^{41}$ to $R^{48}$ in the formula ($\alpha$-2) separately represent hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, or a substituted or unsubstituted triphenylenyl group.

5. The organic compound according to claim 1, wherein $Ar^1$ and $Ar^2$ are represented by a formula (Ar-1):

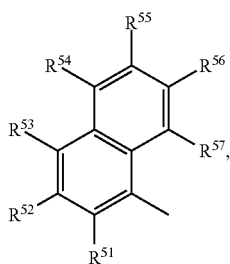

(Ar-1)

and wherein $R^{51}$ to $R^{57}$ separately represent hydrogen, an alkyl group having 1 to 6 carbon atoms, a substituted or unsubstituted phenyl group, or a substituted or unsubstituted biphenyl group.

6. The organic compound according to claim 1, wherein $Ar^1$ and $Ar^2$ are represented by a formula (Ar-2):

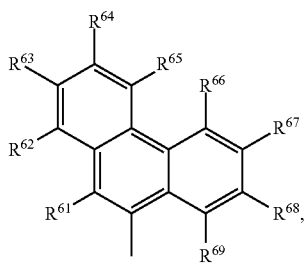

(Ar-2)

and wherein $R^{61}$ to $R^{69}$ separately represent hydrogen, an alkyl group having 1 to 6 carbon atoms, a substituted or unsubstituted phenyl group, or a substituted or unsubstituted biphenyl group.

7. The organic compound according to claim 1, wherein any one of $R^1$ to $R^{10}$ represents a substituent represented by the formula (G1-1), wherein the others separately represent hydrogen, an alkyl group having 1 to 6 carbon atoms, a substituted or unsubstituted phenyl group, or a substituted or unsubstituted biphenyl group, and wherein in the formula (G1-1), $\alpha^1$ represents a substituted or unsubstituted phenylene group or a substituted or unsubstituted biphenyldiyl group, and $Ar^1$ represents a substituted or unsubstituted naphthyl group, a substituted or unsubstituted phenanthryl group, or a substituted or unsubstituted triphenylenyl group.

8. The organic compound according to claim 1, wherein the organic compound is represented by a formula (G3):

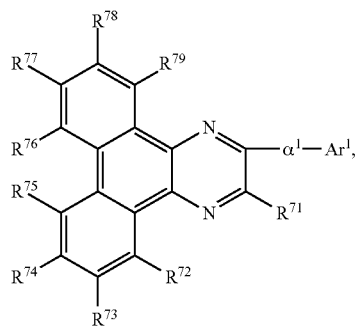

(G3)

wherein $R^{71}$ to $R^{79}$ separately represent hydrogen, an alkyl group having 1 to 6 carbon atoms, a substituted or unsubstituted phenyl group, or a substituted or unsubstituted biphenyl group, wherein $R^{71}$ represents hydrogen, wherein $\alpha^1$ represents a substituted or unsubstituted phenylene group or a substituted or unsubstituted biphenyldiyl group, and wherein $Ar^1$ represents a substituted or unsubstituted naphthyl group, a substituted or unsubstituted phenanthryl group, or a substituted or unsubstituted triphenylenyl group.

9. The organic compound according to claim 7, wherein $\alpha^1$ is represented by a formula ($\alpha$-1) or a formula ($\alpha$-2):

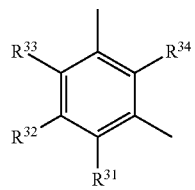

($\alpha$-1)

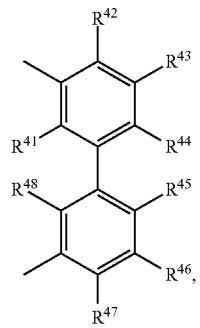

($\alpha$-2)

and wherein $R^{31}$ to $R^{34}$ in the formula ($\alpha$-1) and $R^{41}$ to $R^{48}$ in the formula ($\alpha$-2) separately represent hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, or a substituted or unsubstituted triphenylenyl group.

10. The organic compound according to claim 7, wherein $Ar^1$ is represented by a formula (Ar-1) or a formula (Ar-2):

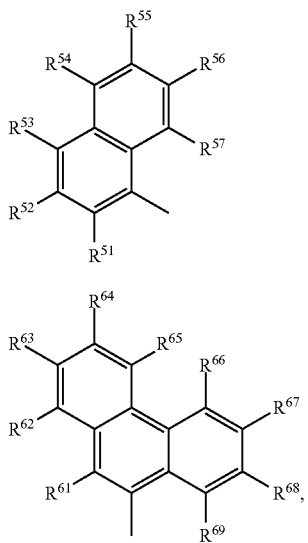

(Ar-1)

(Ar-2)

wherein $R^{51}$ to $R^{57}$ in the formula (Ar-1) and $R^{61}$ to $R^{69}$ in the formula (Ar-2) separately represent hydrogen, an alkyl group having 1 to 6 carbon atoms, a substituted or unsubstituted phenyl group, or a substituted or unsubstituted biphenyl group.

11. A light-emitting device comprising the organic compound according to claim 1, wherein the light-emitting device further comprising:
a pair of electrodes; and
a light-emitting layer containing the organic compound between the pair of electrodes.

12. The light-emitting device according to claim 11, wherein the light-emitting layer further comprises a light-emitting material.

13. The light-emitting device according to claim 12, wherein the light-emitting material is a phosphorescent compound.

14. The light-emitting device according to claim 11, further comprising an electron-transport layer between the light-emitting layer and one of the pair of electrodes, wherein the electron-transport layer comprises the organic compound.

15. The light-emitting device according to claim 14, wherein the electron-transport layer is in contact with the light-emitting layer.

16. The light-emitting device according to claim 14, further comprising a second electron-transport layer between the electron-transport layer and the one of the pair of electrodes.

17. An electronic device comprising the light-emitting device according to claim 11.

18. A lighting device comprising the light-emitting device according to claim 11.

19. The organic compound according to claim 8, wherein $R^{72}$ to $R^{79}$ separately represent hydrogen.

* * * * *

UNITED STATES PATENT AND TRADEMARK OFFICE
CERTIFICATE OF CORRECTION

PATENT NO. : 9,162,990 B2  
APPLICATION NO. : 13/596725  
DATED : October 20, 2015  
INVENTOR(S) : Takako Takasu et al.

It is certified that error appears in the above-identified patent and that said Letters Patent is hereby corrected as shown below:

IN THE SPECIFICATION

Column 47, line 44, after "poly{[" replace "9,9-d]hexyl" with --9,9-dihexyl--;

Column 47, line 45, after "($N,N$" replace "-diphenyl  amino)" with -- -diphenylamino)--;

Column 58, line 52, replace "96311a" with --9631a--;

Column 62, line 37, after "temperature (20 °C" insert --25--;

Column 63, line 30, replace "T of MS" with --Tof MS--;

Column 65, line 65, after "and" replace "mL" with --10mL--;

Column 76, line 27, after "(= NPDBq:NPB" insert --:--;

Column 76, line 56, after "(= NPDBq:NPB" insert --:--;

Column 80, line 24, after "(= DBqPPn:PCBA1BP" insert --:--;

Column 82, line 43, after "(=mPnPDBq:PCBA1BP" insert --:--;

Column 84, line 46, after "(=mPnPDBq:PCBA1BP" insert --:--;

Column 87, line 36, after "di-" replace "p" with --μ--;

Column 87, line 43, after "hydrate" replace "($IrCl_3.H_2O$)" with --($IrCl_3·H_2O$)--;

Column 89, line 51, before "mL of water," insert --20--;

Column 90, line 38, after "di-" replace "p" with --μ--;

Column 90, line 45, replace "($IrCl_3.H_2O$)" with --($IrCl_3·H_2O$)--;

Column 93, line 18, after "di-" replace "p" with --μ--; and

Column 93, line 25, replace "($IrCl_3.H_2O$)" with --($IrCl_3·H_2O$)--.

Signed and Sealed this  
Twenty-ninth Day of March, 2016

Michelle K. Lee  
*Director of the United States Patent and Trademark Office*